United States Patent
Kim et al.

(10) Patent No.: US 11,937,502 B2
(45) Date of Patent: Mar. 19, 2024

(54) CONDENSED CYCLIC COMPOUND AND ORGANIC LIGHT-EMITTING DEVICE COMPRISING THE SAME

(71) Applicants: Samsung Display Co., Ltd., Yongin-si (KR); Research & Business Foundation SUNGKYUNKWAN UNIVERSITY, Suwon-si (KR)

(72) Inventors: Sung-Wook Kim, Yongin-si (KR); Myeong-Suk Kim, Yongin-si (KR); Hwan-Hee Cho, Yongin-si (KR); Sam-Il Kho, Yongin-si (KR); Seung-Soo Yoon, Suwon-si (KR); Changwoong Chu, Yongin-si (KR)

(73) Assignees: Samsung Display Co., Ltd., Yongin-si (KR); Research & Business Foundation Sungkyunkwan University, Suwon-si (KR)

( * ) Notice: Subject to any disclaimer, the term of this patent is extended or adjusted under 35 U.S.C. 154(b) by 333 days.

(21) Appl. No.: 15/098,258

(22) Filed: Apr. 13, 2016

(65) Prior Publication Data
US 2016/0308140 A1 Oct. 20, 2016

(30) Foreign Application Priority Data
Apr. 14, 2015 (KR) .................... 10-2015-0052453

(51) Int. Cl.
| | | |
|---|---|---|
| H01L 51/54 | (2006.01) | |
| H10K 85/60 | (2023.01) | |
| C09K 11/06 | (2006.01) | |
| C09K 11/02 | (2006.01) | |
| C07D 495/10 | (2006.01) | |
| C07D 491/107 | (2006.01) | |
| H10K 50/11 | (2023.01) | |

(52) U.S. Cl.
CPC ....... *H10K 85/657* (2023.02); *C07D 491/107* (2013.01); *C07D 495/10* (2013.01); *C09K 11/025* (2013.01); *C09K 11/06* (2013.01); *H10K 85/626* (2023.02); *H10K 85/6574* (2023.02); *H10K 85/6576* (2023.02); *C09K 2211/1007* (2013.01); *C09K 2211/1014* (2013.01); *H10K 50/11* (2023.02)

(58) Field of Classification Search
CPC .......................................... H01L 51/0512–5044
See application file for complete search history.

(56) References Cited

U.S. PATENT DOCUMENTS

| | | | |
|---|---|---|---|
| 6,251,531 B1 | 6/2001 | Enokida et al. | |
| 7,635,526 B2 | 12/2009 | Stossel et al. | |
| 8,269,317 B2 | 9/2012 | Alleyne | |
| 8,901,298 B2 | 12/2014 | Parham et al. | |
| 8,987,462 B2* | 3/2015 | Kim .............. | H01L 51/006 546/276.7 |
| 9,126,970 B2 | 9/2015 | Pflumm et al. | |
| 9,288,869 B2 | 3/2016 | Han et al. | |

(Continued)

FOREIGN PATENT DOCUMENTS

| | | |
|---|---|---|
| CN | 100481574 C | 4/2009 |
| CN | 103087068 A | 5/2013 |

(Continued)

OTHER PUBLICATIONS

Gong, et al. "Highly efficient blue OLED based on 9-anthracene-spirobenzofluorene derivatives as host materials." Journal of Materials Chemistry 20.47 (2010): 10735-10746.*

(Continued)

*Primary Examiner* — Andrew K Bohaty
(74) *Attorney, Agent, or Firm* — Lewis Roca Rothgerber Christie LLP

(57) ABSTRACT

A condensed cyclic compound and an organic light-emitting device including the condensed cyclic compound are provided. The condensed cyclic compound is represented by Formula 1. The $A_3$ ring of Formula 1 is a group represented by Formula 2A or a group represented by Formula 2B. The organic light-emitting device includes: a first electrode; a second electrode; and an organic layer between the first electrode and the second electrode and including an emission layer, the organic layer including at least one of the condensed cyclic compound represented by Formula 1.

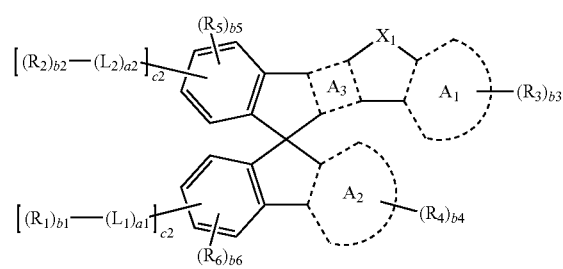

Formula 1

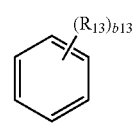

Formula 2A

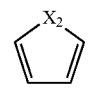

Formula 2B

13 Claims, 4 Drawing Sheets

(56) References Cited

U.S. PATENT DOCUMENTS

| | | | |
|---|---|---|---|
| 9,722,191 B2* | 8/2017 | Kim | H01L 51/0052 |
| 9,818,948 B2 | 11/2017 | Jatsch et al. | |
| 9,837,617 B2 | 12/2017 | Pfister et al. | |
| 10,134,997 B2* | 11/2018 | Kim | H01L 51/0067 |
| 10,186,666 B2 | 1/2019 | Kim et al. | |
| 10,411,195 B2* | 9/2019 | Kim | H01L 51/0073 |
| 10,693,076 B2* | 6/2020 | Hwang | C07D 307/77 |
| 2003/0072966 A1 | 4/2003 | Hosokawa et al. | |
| 2004/0137270 A1 | 7/2004 | Seo et al. | |
| 2004/0197600 A1 | 10/2004 | Thompson et al. | |
| 2006/0024522 A1 | 2/2006 | Thompson | |
| 2007/0009758 A1 | 1/2007 | Funahashi | |
| 2008/0154040 A1 | 6/2008 | Kosuge et al. | |
| 2008/0242871 A1 | 10/2008 | Kawakami et al. | |
| 2009/0108737 A1 | 4/2009 | Kwong et al. | |
| 2009/0124805 A1 | 5/2009 | Alleyne | |
| 2009/0230857 A1 | 9/2009 | Choi et al. | |
| 2009/0278118 A1 | 11/2009 | Ohrui et al. | |
| 2010/0327270 A1 | 12/2010 | Buesing et al. | |
| 2011/0037062 A1 | 2/2011 | Fukumatsu et al. | |
| 2011/0112275 A1 | 5/2011 | Parham et al. | |
| 2012/0018717 A1 | 1/2012 | Kim et al. | |
| 2012/0080670 A1 | 4/2012 | Park et al. | |
| 2012/0091885 A1 | 4/2012 | Kim et al. | |
| 2012/0097899 A1 | 4/2012 | Parham et al. | |
| 2012/0097924 A1 | 4/2012 | Kim et al. | |
| 2012/0104379 A1 | 5/2012 | Kawakami et al. | |
| 2012/0112174 A1 | 5/2012 | Lee et al. | |
| 2012/0138914 A1 | 6/2012 | Kawamura et al. | |
| 2012/0175561 A1 | 7/2012 | Franz et al. | |
| 2012/0181922 A1 | 7/2012 | Kawamura et al. | |
| 2012/0235123 A1 | 9/2012 | Lee et al. | |
| 2013/0092913 A1 | 4/2013 | Nishimura et al. | |
| 2013/0105769 A1 | 5/2013 | Lim et al. | |
| 2013/0200350 A1 | 8/2013 | Sawada et al. | |
| 2013/0240796 A1 | 9/2013 | Parham et al. | |
| 2013/0256645 A1 | 10/2013 | Min et al. | |
| 2013/0341599 A1 | 12/2013 | Xia et al. | |
| 2014/0131664 A1 | 5/2014 | Yen et al. | |
| 2014/0151647 A1 | 6/2014 | Mizuki et al. | |
| 2014/0225040 A1 | 8/2014 | Parham et al. | |
| 2014/0225046 A1 | 8/2014 | Jatsch et al. | |
| 2014/0306197 A1* | 10/2014 | Kim | H01L 51/006 257/40 |
| 2014/0367647 A1 | 12/2014 | Kim et al. | |
| 2015/0021563 A1* | 1/2015 | Kim | H01L 51/0052 257/40 |
| 2015/0021585 A1 | 1/2015 | Yu et al. | |
| 2015/0060785 A1* | 3/2015 | Kim | H01L 51/0074 257/40 |
| 2015/0060808 A1* | 3/2015 | Kim | H01L 51/0052 257/40 |
| 2015/0311450 A1 | 10/2015 | Park et al. | |
| 2015/0318478 A1 | 11/2015 | Pflumm et al. | |
| 2016/0043330 A1 | 2/2016 | Kim et al. | |
| 2016/0126475 A1 | 5/2016 | Lee et al. | |
| 2016/0126479 A1 | 5/2016 | Hwang et al. | |
| 2016/0190466 A1* | 6/2016 | Pfister | H01L 51/0056 252/500 |
| 2016/0214942 A1 | 7/2016 | Parham et al. | |
| 2016/0218300 A1 | 7/2016 | Xia et al. | |
| 2016/0293848 A1* | 10/2016 | Kim | H01L 51/0067 |
| 2016/0308147 A1* | 10/2016 | Parham | C07F 15/0033 |
| 2017/0062729 A1 | 3/2017 | Cha et al. | |
| 2017/0162801 A1* | 6/2017 | Cho | H01L 51/0074 |
| 2017/0179404 A1* | 6/2017 | Kim | H01L 51/006 |
| 2017/0346009 A1* | 11/2017 | Yokoyama | H01L 51/006 |
| 2017/0346015 A1* | 11/2017 | Hayashi | H01L 51/0059 |
| 2017/0352813 A1* | 12/2017 | Duan | H01L 51/0067 |
| 2018/0006245 A1* | 1/2018 | Pfister | |
| 2018/0208836 A1 | 7/2018 | Kuma et al. | |

FOREIGN PATENT DOCUMENTS

| | | | |
|---|---|---|---|
| CN | 103718316 A | 4/2014 | |
| CN | 103842339 A | 6/2014 | |
| JP | 2010114180 A | 5/2010 | |
| KR | 10-2008-0096733 A | 11/2008 | |
| KR | 20090011487 A * | 2/2009 | |
| KR | 10-2009-0098646 A | 9/2009 | |
| KR | 20090117326 A * | 11/2009 | |
| KR | 10-2010-0106026 | 10/2010 | |
| KR | 10-2010-0110895 A | 10/2010 | |
| KR | 10-2010-0121378 A | 11/2010 | |
| KR | 10-2010-0130197 A | 12/2010 | |
| KR | 10-2011-0002156 A | 1/2011 | |
| KR | 10-2011-0007124 A | 1/2011 | |
| KR | 10-2011-0021487 A | 3/2011 | |
| KR | 10-2011-0032373 A | 3/2011 | |
| KR | 10-2011-0068330 A | 6/2011 | |
| KR | 10-2011-0088378 A | 8/2011 | |
| KR | 10-2012-0006000 A | 1/2012 | |
| KR | 10-2012-0034140 | 4/2012 | |
| KR | 10-2012-0038402 | 4/2012 | |
| KR | 10-2012-0043623 A | 5/2012 | |
| KR | 10-2012-0060611 A | 6/2012 | |
| KR | 10-2012-0078301 | 7/2012 | |
| KR | 10-2012-0089223 A | 8/2012 | |
| KR | 10-2012-0117622 | 10/2012 | |
| KR | 20120135837 A | 12/2012 | |
| KR | 10-2013-0011405 A | 1/2013 | |
| KR | 10-2013-0042865 A | 4/2013 | |
| KR | 10-2013-0051807 A | 5/2013 | |
| KR | 10-2013-0077470 A | 7/2013 | |
| KR | 10-2013-0122602 | 11/2013 | |
| KR | 10-1381505 B1 | 3/2014 | |
| KR | 10-2014-0054132 A | 5/2014 | |
| KR | 10-2014-0069199 A | 6/2014 | |
| KR | 10-2014-0088003 A | 7/2014 | |
| KR | 10-2014-0104895 | 8/2014 | |
| KR | 10-2014-0105913 A | 9/2014 | |
| KR | 10-2015-0006802 A | 1/2015 | |
| KR | 10-2015-0025529 A | 3/2015 | |
| KR | 10-2015-0113642 A | 10/2015 | |
| KR | 10-2015-0128583 A | 11/2015 | |
| KR | 10-2015-0132660 A | 11/2015 | |
| KR | 10-2016-0053423 A | 5/2016 | |
| KR | 10-2016-0119904 A | 10/2016 | |
| WO | WO 2010/110554 A2 | 9/2010 | |
| WO | WO 2010/136109 A1 | 12/2010 | |
| WO | WO 2011/025282 A2 | 3/2011 | |
| WO | WO 2011/037380 A2 | 10/2011 | |
| WO | WO-2013100464 A1 * | 7/2013 | C09K 11/06 |
| WO | WO 2014/007564 A1 | 1/2014 | |
| WO | WO-2014104600 A1 * | 7/2014 | C07D 209/86 |
| WO | WO-2014129846 A1 * | 8/2014 | C07B 59/002 |
| WO | 2014/185751 A1 | 11/2014 | |
| WO | WO-2015012618 A1 * | 1/2015 | C07C 211/61 |
| WO | 2015/022051 A1 | 2/2015 | |
| WO | WO 2015/053463 A1 | 4/2015 | |
| WO | WO 2015/090504 A2 | 6/2015 | |
| WO | WO 2016/017919 A2 | 2/2016 | |

OTHER PUBLICATIONS

Machine Translation of KR 2013/0122602 A.*
Machine Translation of WO-2014104600-A1.*
Machine Translation of WO-2014129846-A1.*
Machine Translation WO-2013100464-A1.*
Machine translation for KR 10-2012-0078301 A (publication date Jul. 2012).
Cheuk-Lam Ho, et al., ""Small-Molecular blue phosphorescent dyes for organic light-emitting devices""", New J. Chem., 2013,37, 1665-1683 (Only abstract enclosed).
U.S. Final Office action dated Mar. 19, 2021, issued in U.S. Appl. No. 15/377,732 (20 pages).
Advisory Action for U.S. Appl. No. 14/457,533 dated Jan. 30, 2017, 3 pages.
Advisory Action for U.S. Appl. No. 14/457,533 dated Nov. 15, 2017, 3 pages.

(56) References Cited

OTHER PUBLICATIONS

Advisory Action for U.S. Appl. No. 15/377,732 dated Jun. 8, 2021, 3 pages.
Advisory Action for U.S. Appl. No. 15/377,732 dated Mar. 4, 2020, 3 pages.
Final Office Action for U.S. Appl. No. 14/253,830 dated Jul. 30, 2018, 12 pages.
Final Office Action for U.S. Appl. No. 14/253,830 dated Sep. 15, 2017, 10 pages.
Final Office Action for U.S. Appl. No. 14/457,533 dated Jul. 24, 2017, 10 pages.
Final Office Action for U.S. Appl. No. 14/457,533 dated Nov. 15, 2016, 14 pages,.
Final Office Action for U.S. Appl. No. 15/377,732 dated Dec. 12, 2019, 8 pages.
Final Office Action for U.S. Appl. No. 15/703,770 dated Dec. 2, 2019, 10 pages.
Notice of Allowance for U.S. Appl. No. 14/036,574 dated Nov. 7, 2014, 8 pages.
Notice of Allowance for U.S. Appl. No. 14/253,830 dated May 2, 2019, 8 pages.
Notice of Allowance for U.S. Appl. No. 14/457,533 dated Jul. 5, 2018, 8 pages.
Notice of Allowance for U.S. Appl. No. 14/661,427 dated Mar. 30, 2017, 8 pages.
Notice of Allowance for U.S. Appl. No. 14/963,274 dated Aug. 29, 2018, 10 pages.
Notice of Allowance for U.S. Appl. No. 15/703,770 dated Feb. 10, 2020, 6 pages.
Office Action for U.S. Appl. No. 14/253,830 dated Feb. 7, 2018, 12 pages.
Office Action for U.S. Appl. No. 14/253,830 dated Mar. 7, 2017, 9 pages.
Office Action for U.S. Appl. No. 14/253,830 dated Nov. 26, 2018, 12 pages.
Office Action for U.S. Appl. No. 14/457,533 dated Feb. 9, 2018, 11 pages.
Office Action for U.S. Appl. No. 14/457,533 dated Jun. 22, 2016, 10 pages.
Office Action for U.S. Appl. No. 14/457,533 dated Mar. 9, 2017, 9 pages.
Office Action for U.S. Appl. No. 14/963,274 dated Mar. 16, 2018, 11 pages.
Office Action for U.S. Appl. No. 15/377,732 dated Dec. 17, 2021, 15 pages.
Office Action for U.S. Appl. No. 15/377,732 dated Jun. 24, 2019, 9 pages.
Office Action for U.S. Appl. No. 15/377,732 dated May 17, 2022, 32 pages.
Office Action for U.S. Appl. No. 15/377,732 dated Sep. 8, 2020, 15 pages.
Office Action for U.S. Appl. No. 15/703,770 dated Jun. 3, 2019, 10 pages.
Restriction Requirement for U.S. Appl. No. 14/963,274 dated Sep. 27, 2017, 6 pages.
Final Office Action for U.S. Appl. No. Oct. 31, 2022, 9 pages.
Korean Notice of Allowance for KR Patent Application No. 10-2015-0048326 dated Oct. 5, 2022, 3 pages.
Advisory Action for U.S. Appl. No. 15/377,732 dated Jan. 23, 2023, 22 pages.
Office Action for U.S. Appl. No. 15/377,732 dated Mar. 31, 2023, 8 pages.
U.S. Notice of Allowance dated Aug. 28, 2023, issued in U.S. Appl. No. 15/377,732 (8 pages).

* cited by examiner

| 190 |
|-----|
| 150 |
| 110 |

| 190 |
|-----|
| 150 |
| 110 |
| 210 |

| 220 |
|-----|
| 190 |
| 150 |
| 110 |

| |
|---|
| 220 |
| 190 |
| 150 |
| 110 |
| 210 |

CONDENSED CYCLIC COMPOUND AND ORGANIC LIGHT-EMITTING DEVICE COMPRISING THE SAME

CROSS-REFERENCE TO RELATED APPLICATION

This application claims priority to and the benefit of Korean Patent Application No. 10-2015-0052453, filed on Apr. 14, 2015, in the Korean Intellectual Property Office, the entire content of which is incorporated herein by reference.

BACKGROUND

1. Field

One or more embodiments of the present disclosure relate to a condensed cyclic compound and an organic light-emitting device including the same.

2. Description of the Related Art

Organic light-emitting devices (OLEDs) are self-emitting devices that have features such as wide viewing angles, excellent contrast, quick response, high brightness, excellent driving voltage characteristics, and can provide multicolored images.

An organic light-emitting device may have a structure in which a first electrode, a hole transport region, an emission layer, an electron transport region, and a second electrode are sequentially disposed in the stated order on a substrate. Holes injected from the first electrode move to the emission layer via the hole transport region, while electrons injected from the second electrode move to the emission layer via the electron transport region. Carriers such as the holes and electrons recombine in the emission layer to generate excitons. When the excitons drop from an excited state to a ground state, light is emitted.

SUMMARY

One or more embodiments of the present disclosure include a novel condensed cyclic compound and an organic light-emitting device including the same.

Additional aspects of embodiments will be set forth in part in the description which follows and, in part, will be apparent from the description, or may be learned by practice of the described embodiments.

According to one or more embodiments of the present disclosure, there is provided a condensed cyclic compound represented by Formula 1:

Formula 1

Formula 2A

Formula 2B wherein, in Formulae 1, 2A, and 2B, $A_1$ ring and $A_2$ ring are each independently selected from a benzene, a naphthalene, a pyridine, a pyrimidine, a pyrazine, a quinoline, an isoquinoline, a quinoxaline, a quinazoline, and a cinnoline;

$A_3$ ring is a group represented by Formula 2A or a group represented by Formula 2B;

$X_1$ is $N-[(L_{11})_{a11}-(R_{11})_{b11}]$, O, or S;

$X_2$ is $N-[(L_{12})_{a12}-(R_{12})_{b12}]$, O, or S;

$L_1$ and $L_2$ are each independently selected from a substituted or unsubstituted condensed polycyclic group including at least three carbocyclic groups condensed together;

a1 and a2 are each independently an integer selected from 1 to 5, wherein, when a1 is 2 or greater, at least two $L_1$s are the same or different, and when a2 is 2 or greater, at least two $L_2$s are the same or different;

$L_{11}$ and $L_{12}$ are each independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group;

a11 and a12 are each independently an integer selected from 0 to 5, wherein, when a11 is 2 or greater, at least two $L_{11}$s are the same or different, and when a12 is 2 or greater, at least two $L_{12}$s are the same or different;

$R_1$ to $R_6$ and $R_{11}$ to $R_{13}$ are each independently selected from a hydrogen, a deuterium, —F, —Cl, —Br, —I, a hydroxyl group, a cyano group, a nitro group, an amino group, an am idino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, $-N(Q_1)(Q_2)$, $-Si(Q_3)(Q_4)(Q_5)$, and $-B(Q_6)(Q_7)$;

b1, b2, b5, b6, b11, and b12 are each independently an integer selected from 0 to 4;

b3 and b4 are each independently an integer selected from 0 to 6;

b13 is 0, 1, or 2;

c1 and c2 are each independently an integer selected from 0 to 4, wherein c1+c2 is 1 or greater;

at least one substituent of the substituted condensed polycyclic group including at least three carbocyclic groups condensed together, the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group is selected from:

a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group, a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{16}$), and —B($Q_{16}$)($Q_{17}$), a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$), and —N($Q_{31}$)($Q_{32}$), —Si($Q_{33}$)($Q_{34}$)($Q_{35}$), and —B($Q_{36}$)($Q_{37}$), wherein $Q_1$ to $Q_7$, $Q_{11}$ to $Q_{17}$, $Q_{21}$ to $Q_{27}$, and $Q_{31}$ to $Q_{37}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

According to one or more embodiments of the present disclosure, an organic light-emitting device includes: a first electrode; a second electrode facing the first electrode; and an organic layer between the first electrode and the second electrode and including an emission layer, wherein the organic layer includes at least one of the above-described condensed cyclic compound represented by Formula 1.

BRIEF DESCRIPTION OF THE DRAWINGS

These and/or other aspects of embodiments will become apparent and more readily appreciated from the following description of certain embodiments, when considered together with the accompanying drawings in which:

FIGS. 1-4 are schematic views of structures of organic light-emitting devices according to embodiments of the present disclosure.

DETAILED DESCRIPTION

Reference will now be made in more detail to certain embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of embodiments of the present description. As used herein, the term "and/or" includes any and all combinations of one or more of the associated listed items. Expressions such as "at least one of," when preceding a list of elements, modify the entire list of elements and do not modify the individual elements of the list. Also, in the context of the present disclosure, when a first element is referred to as being "on" a second element, it can be directly on the second element or be indirectly on the second element with one or more intervening elements interposed therebetween.

According to an embodiment of the present disclosure, there is provided a condensed cyclic compound represented by Formula 1.

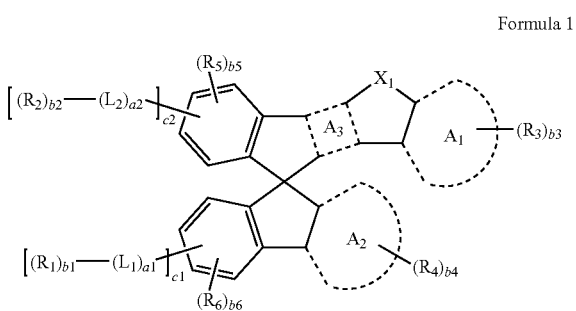

Formula 1

In Formula 1, $A_1$ ring and $A_2$ ring are each fused to an adjacent 5-membered ring, sharing a carbon. For example, the $A_1$ ring is fused to, and shares at least one carbon atom with, a 5-membered ring adjacent to the $A_1$ ring, and the $A_2$ ring is fused to, and shares at least one carbon atom with, a 5-membered ring adjacent to the $A_2$ ring. In Formula 1, the $A_1$ ring and the $A_2$ ring may be each independently selected from a benzene, a naphthalene, a pyridine, a pyrimidine, a pyrazine, a quinoline, an isoquinoline, a quinoxaline, a quinazoline, and a cinnoline.

For example, in Formula 1, the $A_1$ ring and the $A_2$ ring may be each independently selected from a benzene, a naphthalene, a pyridine, a quinoline, and an isoquinoline.

In some embodiments, in Formula 1, the $A_1$ ring may be a benzene or a pyridine, and the $A_2$ ring may be selected from a benzene, a naphthalene, a pyridine, a quinoline, and an isoquinoline; or the $A_1$ ring may be selected from a naphthalene, a quinoline, and an isoquinoline, and the $A_2$ ring may be a benzene or a pyridine. However, embodiments of the condensed cyclic compound are not limited thereto.

In Formula 1, $A_3$ ring may be fused to two adjacent 5-membered rings, sharing a carbon. For example, the $A_3$ ring may be fused to, and share at least one carbon atom with, the 5-membered ring adjacent to the $A_1$ ring, the 5-membered ring being adjacent to the $A_3$ ring, and the $A_3$ ring may be fused to, and share at least one carbon atom with, another 5-membered ring adjacent to the $A_3$ ring. In Formula 1, the $A_3$ ring may be a group represented by Formula 2A or a group represented by Formula 2B.

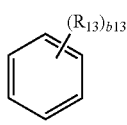

Formula 2A

Formula 2B $R_{13}$ and $b_{13}$ in Formula 2A, and $X_2$ in Formula 2B are described in more detail below.

In some embodiments, in Formula 1, the $A_3$ ring may be a group represented by Formula 2A. However, embodiments of the condensed cyclic compound are not limited thereto.

In Formula 1, $X_1$ may be N-$[(L_{11})_{a11}$-$(R_{11})_{b11}]$, O, or S. In Formula 2B, $X_2$ may be N-$[(L_{12})_{a12}$-$(R_{12})_{b12}]$, O, or S.

For example, in Formula 1, $X_1$ may be O or S.

In Formula 1, $L_1$ and $L_2$ may be each independently a substituted or unsubstituted condensed polycyclic group including at least three carbocyclic groups condensed together (e.g., combined or fused together). $L_1$ and $L_2$ in Formula 1 may include a carbon as a ring-member atom, but not a heteroatom (for example, N, O, S, P, or the like; e.g., in some embodiments, $L_1$ and $L_2$ in Formula 1 do not include a heteroatom as a ring-member (ring-forming atom)). For example, according to the immediately foregoing description, a naphthylene group is not encompassed by $L_1$ and $L_2$ since the naphthylene group is a condensed polycyclic group including two carbocyclic groups condensed together (instead of at least three carbocyclic groups condensed together) and a pyridinylene group is not encompassed by $L_1$ and $L_2$ since the pyridinylene group includes a heteroatom (nitrogen) as a ring-member atom.

In some embodiments, in Formula 1, $L_1$ and $L_2$ may be each independently selected from:

an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, and an ovalenylene group, and an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, and an ovalenylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, and —Si($Q_{33}$)($Q_{34}$)($Q_{35}$), wherein $Q_{33}$ to $Q_{35}$ may be each independently selected from a $C_1$-$C_{10}$ alkyl group, a $C_1$-$C_{10}$ alkoxy group, a phenyl group, and a naphthyl group.

In some embodiments, in Formula 1, $L_1$ and $L_2$ may be each independently selected from:

a phenalenylene group, a phenanthrenylene group, an anthracenylene group, a fluoranthenylene group, a triphenylenylene group, a pyrenylene group, a chrysenylene group, and a perylenylene group, and a phenalenylene group, a phenanthrenylene group, an anthracenylene group, a fluoranthenylene group, a triphenylenylene group, a pyrenylene group, a chrysenylene group, and a perylenylene group, each substituted with at least one selected from a deuterium, —F, —Cl, —Br, —I, a hydroxyl group, a cyano group, a nitro group, an amino group, an am idino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, and —Si($Q_{33}$)($Q_{34}$)($Q_{35}$), wherein $Q_{33}$ to $Q_{35}$ may be each independently selected from a $C_1$-$C_{10}$ alkyl group, a $C_1$-$C_{10}$ alkoxy group, a phenyl group, and a naphthyl group.

In Formula 1, a1 and a2 may be each independently an integer selected from 1 to 5, wherein, when a1 is 2 or greater, at least two $L_1$s may be the same or different, and when a2 is 2 or greater, at least two $L_2$s may be the same or different. In some embodiments, the group represented by *-[($L_1$)$_{a1}$-($R_1$)$_{b1}$] in Formula 1 has at least one of "$L_1$" and the group represented by *-[($L_2$)$_{a2}$-($R_2$)$_{b2}$] in Formula 1 has at least one of "$L_2$".

In some embodiments, in Formula 1, a1 and a2 may be each independently 1 or 2. For example, a1 and a2 may be both 1. However, embodiments of the condensed cyclic compound are not limited thereto.

In Formulae 1, 2A, and 2B, $L_{11}$ and $L_{12}$ may be each independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group.

In some embodiments, $L_{11}$ and $L_{12}$ may be each independently selected from:

a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, and an imidazopyrimidinylene group, and a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, and an imidazopyrimidinylene group, each substituted with at least one selected from a deuterium, —F, —Cl, —Br, —I, a hydroxyl group, a cyano group, a nitro group, an amino group, an am idino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, and —Si($Q_{33}$)($Q_{34}$)($Q_{35}$), wherein $Q_{33}$ to $Q_{35}$ may be each independently selected from a $C_1$-$C_{10}$ alkyl group, a $C_1$-$C_{10}$ alkoxy group, a phenyl group, and a naphthyl group.

In some embodiments, $L_1$ and $L_2$ may be each independently selected from groups respectively represented by Formulae 3-8, 3-9, 3-25, and 3-35 to 3-41; and $L_{11}$ and $L_{12}$ may be each independently selected from groups respectively represented by Formulae 3-1 to 3-41.

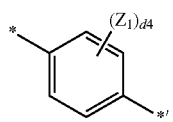

Formula 3-1

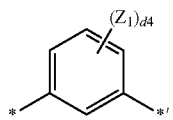

Formula 3-2

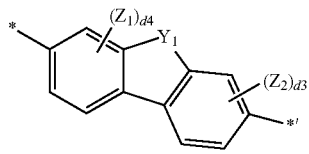

Formula 3-3

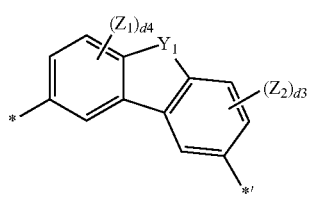

Formula 3-4

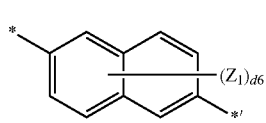

Formula 3-5

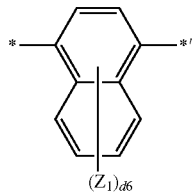

Formula 3-6

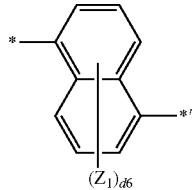

Formula 3-7

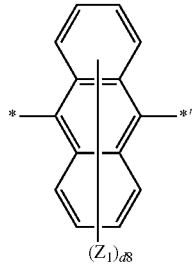

Formula 3-8

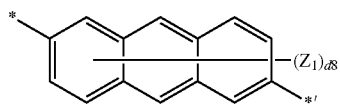

Formula 3-9

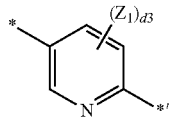

Formula 3-10

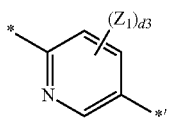
Formula 3-11
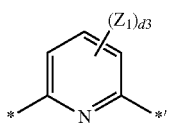
Formula 3-12
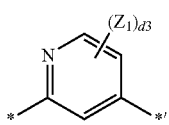
Formula 3-13
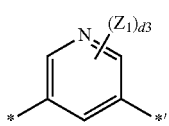
Formula 3-14
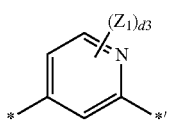
Formula 3-15
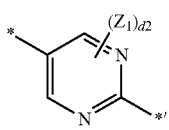
Formula 3-16
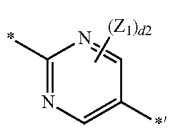
Formula 3-17
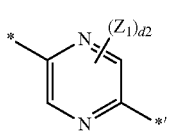
Formula 3-18
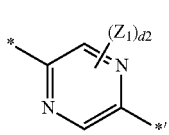
Formula 3-19
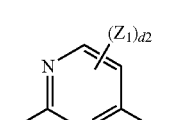
Formula 3-20
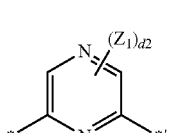
Formula 3-21
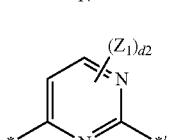
Formula 3-22
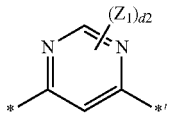
Formula 3-23
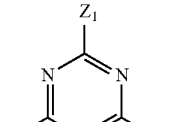
Formula 3-24
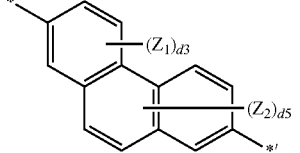
Formula 3-25
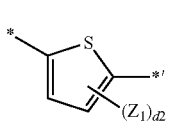
Formula 3-26
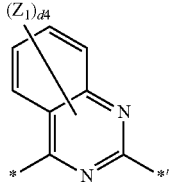
Formula 3-27
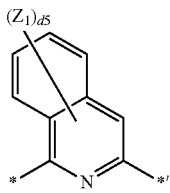
Formula 3-28
Formula 3-29
Formula 3-30
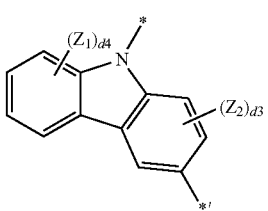
Formula 3-31

-continued

Formula 3-32
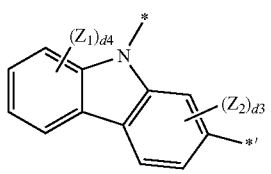

Formula 3-33
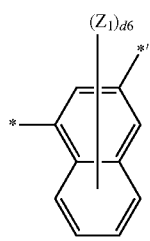

Formula 3-34
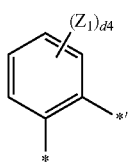

Formula 3-35
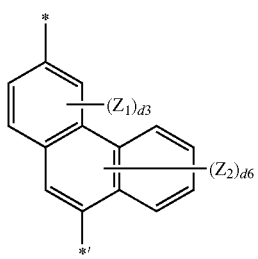

Formula 3-36
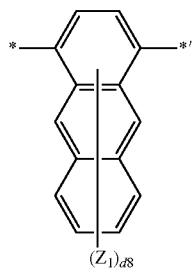

Formula 3-37
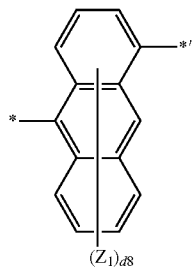

Formula 3-38
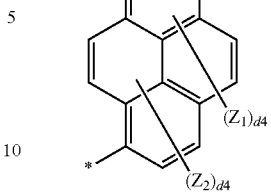

Formula 3-39
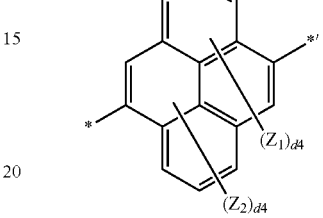

Formula 3-40
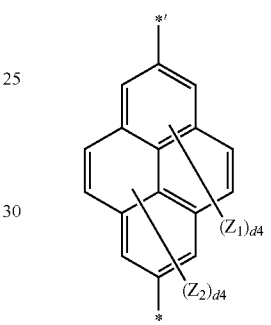

Formula 3-41
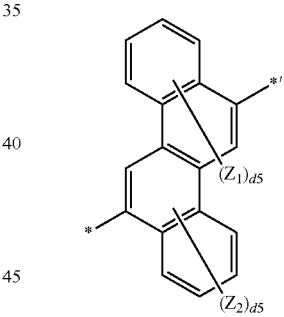

In Formulae 3-1 to 3-41, $Y_1$ may be O, S, $C(Z_3)(Z_4)$, $N(Z_5)$, or $Si(Z_6)(Z_7)$;

$Z_1$ to $Z_7$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, and —Si($Q_{33}$)($Q_{34}$)($Q_{35}$), wherein $Q_{33}$ to $Q_{35}$ may be each independently selected from a $C_1$-$C_{10}$ alkyl group, a $C_1$-$C_{10}$ alkoxy group, a phenyl group, and a naphthyl group;

d2 may be 1 or 2;
d3 may be an integer selected from 1 to 3;
d4 may be an integer selected from 1 to 4;
d5 may be an integer selected from 1 to 5;
d6 may be an integer selected from 1 to 6;
d8 may be an integer selected from 1 to 8; and
\* and \*' may be binding sites with an adjacent atom.

In some other embodiments, $L_1$ and $L_2$ may be each independently selected from groups respectively represented by Formulae 4-11, 4-13, 4-27, and 4-29 to 4-35; and $L_{11}$ and $L_{12}$ may be each independently selected from groups respectively represented by Formulae 4-1 to 4-35. However, embodiments of the condensed cyclic compound are not limited thereto.

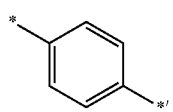

Formula 4-1

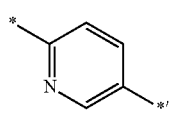

Formula 4-2

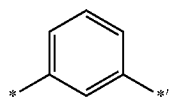

Formula 4-3

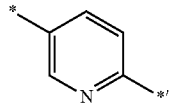

Formula 4-4

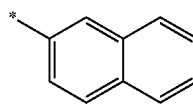

Formula 4-5

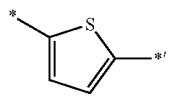

Formula 4-6

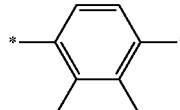

Formula 4-7

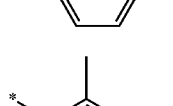

Formula 4-8

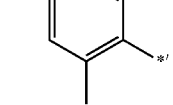

Formula 4-9

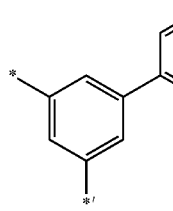

Formula 4-10

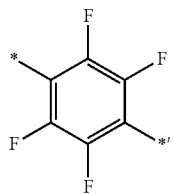

Formula 4-11

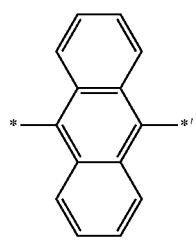

Formula 4-12

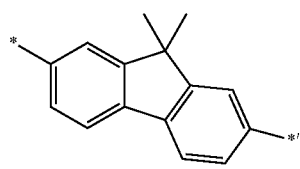

Formula 4-13

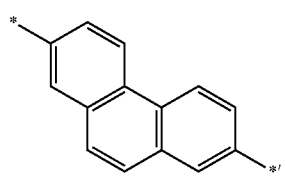

Formula 4-14

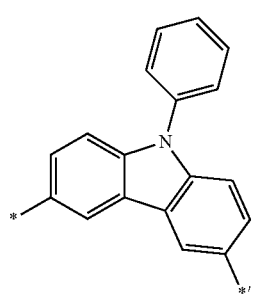

Formula 4-15

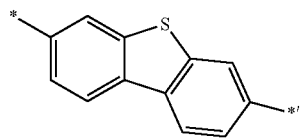

Formula 4-16

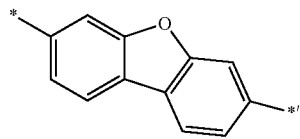

Formula 4-17

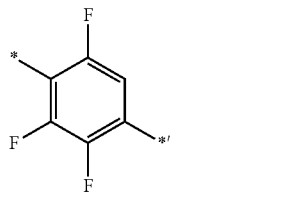

-continued

Formula 4-18

Formula 4-19

Formula 4-20

Formula 4-21

Formula 4-22

Formula 4-23

Formula 4-24

Formula 4-25

Formula 4-26

-continued

Formula 4-27

Formula 4-27

Formula 4-28

Formula 4-29

Formula 4-30

Formula 4-31

Formula 4-32

-continued

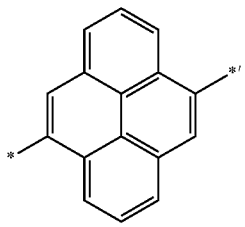
Formula 4-33

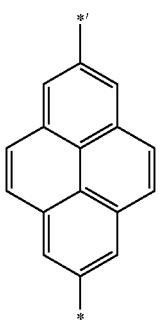
Formula 4-34

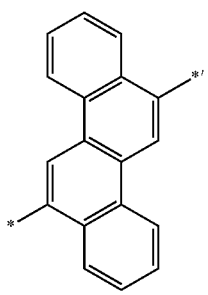
Formula 4-35

In Formulae 4-1 to 4-35, * and *' are binding sites with an adjacent atom.

In Formulae 1 and 2B, a11 and a12 may be each independently an integer selected from 0 to 5, wherein, when a11 is 2 or greater, at least two $L_{11}$s may be the same or different, and when a12 is 2 or greater, at least two $L_{12}$s may be the same or different.

In some embodiments, in Formulae 1 and 2B, a11 and a12 may be each independently 0, 1, or 2. For example, a11 and a12 may be each independently 0 or 1. However, embodiments of the condensed cyclic compound are not limited thereto.

In Formulae 1, 2A, and 2B, $R_1$ to $R_6$ and $R_{11}$ to $R_{13}$ may be each independently selected from a hydrogen, a deuterium, —F, —Cl, —Br, —I, a hydroxyl group, a cyano group, a nitro group, an amino group, an am idino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), and —B($Q_6$)($Q_7$).

For example, in Formulae 1, 2A, and 2B, $R_1$ to $R_6$ and $R_{11}$ to $R_{13}$ may be each independently selected from:
a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group,
a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof,
a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a dibenzosilolyl group, a thiadiazolyl group, an imidazopyridinyl group, and an imidazopyrimidinyl group,
a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a dibenzosilolyl group, a thiadiazolyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group and —Si($Q_{33}$)($Q_{34}$)($Q_{35}$), and —Si($Q_3$)($Q_4$)($Q_5$), wherein $Q_3$ to $Q_5$ and $Q_{33}$ to $Q_{35}$ may be each independently selected from a $C_1$-$C_{10}$ alkyl group, a $C_1$-$C_{10}$ alkoxy group, a phenyl group, and a naphthyl group.

In some embodiments, in Formulae 1, 2A, and 2B, $R_1$ to $R_6$ and $R_{11}$ to $R_{13}$ may be each independently selected from:

a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, an imidazopyridinyl group, and an imidazopyrimidinyl group, a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, an imidazopyridinyl group, an imidazopyrimidinyl group, and —Si($Q_{33}$)($Q_{34}$)($Q_{35}$), and —Si($Q_3$)($Q_4$)($Q_5$), wherein $Q_3$ to $Q_5$ and $Q_{33}$ to $Q_{35}$ may be each independently selected from a $C_1$-$C_{10}$ alkyl group, a $C_1$-$C_{10}$ alkoxy group, a phenyl group, and a naphthyl group.

In some embodiments, in Formulae 1, 2A, and 2B, $R_1$ to $R_6$ and $R_{11}$ to $R_{13}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, groups respectively represented by Formulae 5-1 to 5-75, and —Si($Q_3$)($Q_4$)($Q_5$), wherein $Q_3$ to $Q_5$ may be each independently selected from a $C_1$-$C_{10}$ alkyl group, a $C_1$-$C_{10}$ alkoxy group, a phenyl group, and a naphthyl group.

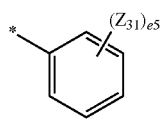

Formula 5-1

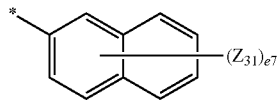

Formula 5-2

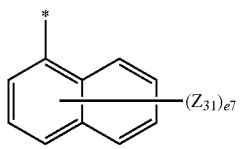

Formula 5-3

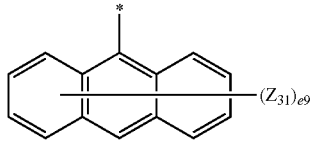

Formula 5-4

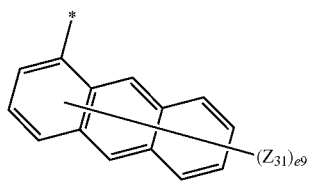

Formula 5-5

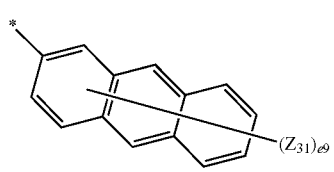

Formula 5-6

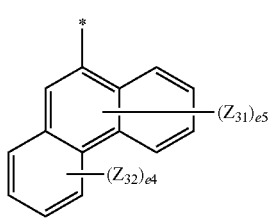

Formula 5-7

-continued

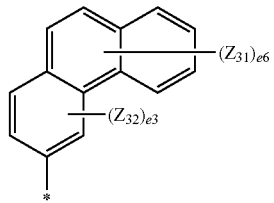

Formula 5-8

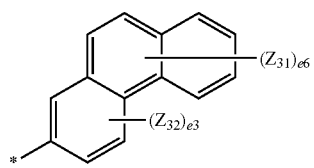

Formula 5-9

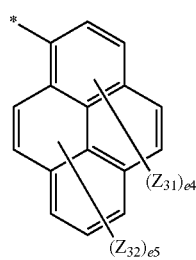

Formula 5-10

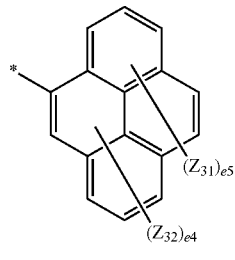

Formula 5-11

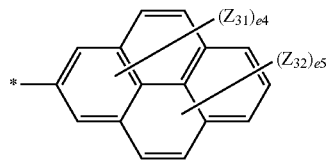

Formula 5-12

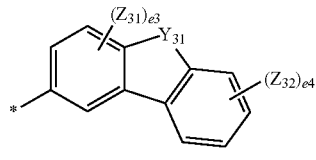

Formula 5-13

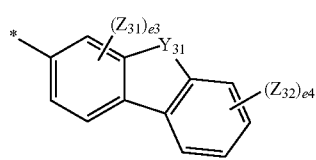

Formula 5-14

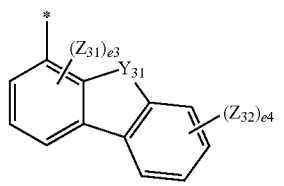

Formula 5-15

-continued
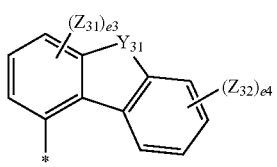
Formula 5-16
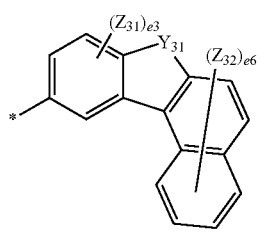
Formula 5-17
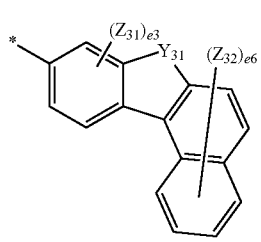
Formula 5-18
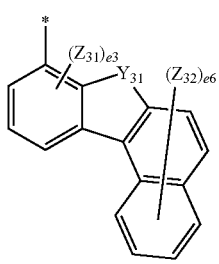
Formula 5-19
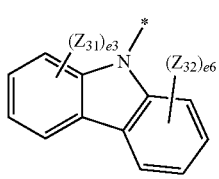
Formula 5-20
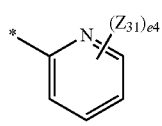
Formula 5-21
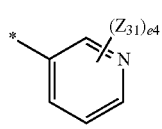
Formula 5-22
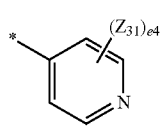
Formula 5-23
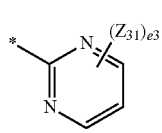
Formula 5-24
-continued
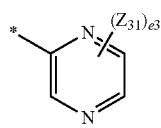
Formula 5-25
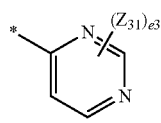
Formula 5-26
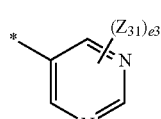
Formula 5-27
Formula 5-28
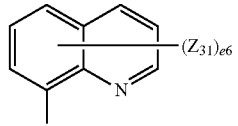
Formula 5-29
Formula 5-30
Formula 5-31
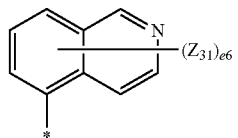
Formula 5-32
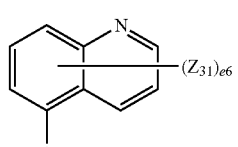
Formula 5-33
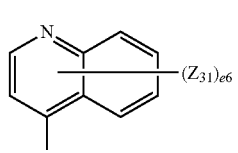
Formula 5-34
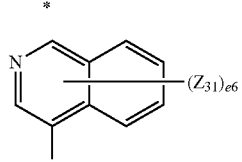
Formula 5-35
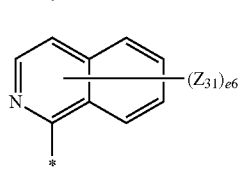

-continued
Formula 5-36
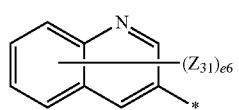
Formula 5-37
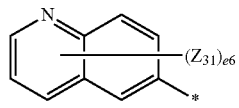
Formula 5-38
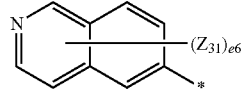
Formula 5-39
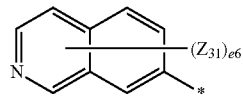
Formula 5-40
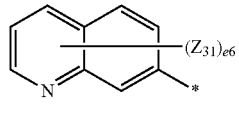
Formula 5-41
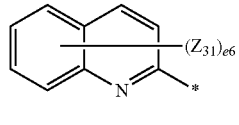
Formula 5-42
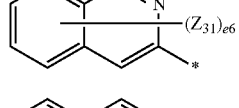
Formula 5-43
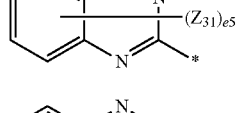
Formula 5-44
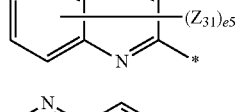
Formula 5-45
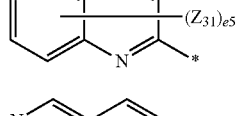
Formula 5-46
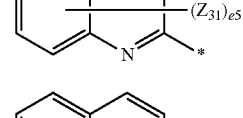
Formula 5-47
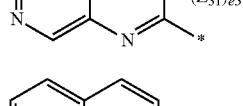
Formula 5-48
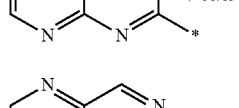
Formula 5-49
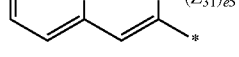
Formula 5-50
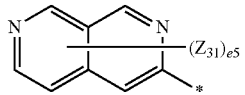
Formula 5-51
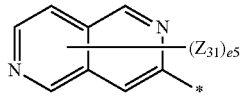
Formula 5-52
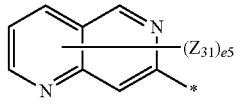
Formula 5-53
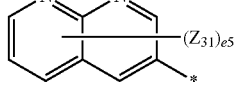
Formula 5-54
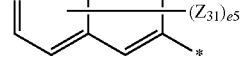
Formula 5-55
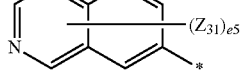
Formula 5-56
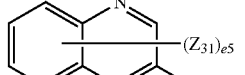
Formula 5-57
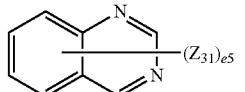
Formula 5-58
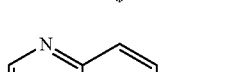
Formula 5-59
Formula 5-60
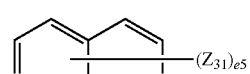
Formula 5-61
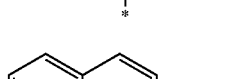
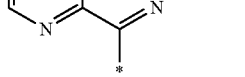

-continued

Formula 5-62
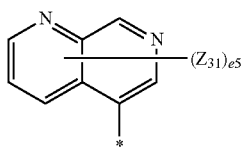

Formula 5-63
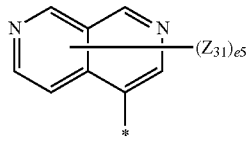

Formula 5-64
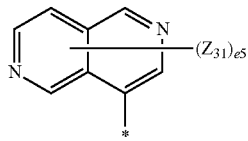

Formula 5-65
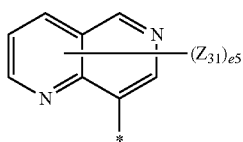

Formula 5-66
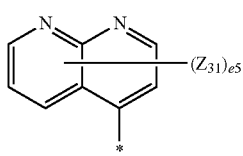

Formula 5-67
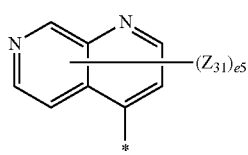

Formula 5-68
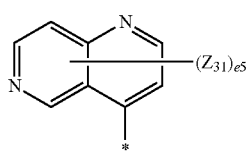

Formula 5-69
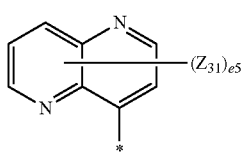

Formula 5-70
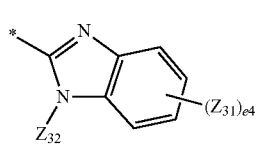

Formula 5-71
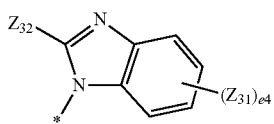

Formula 5-72
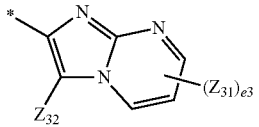

Formula 5-73
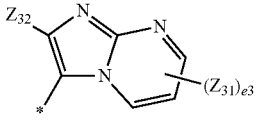

Formula 5-74
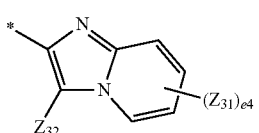

Formula 5-75
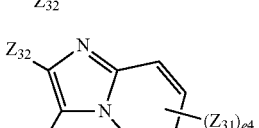

In Formulae 5-1 to 5-75, $Y_{31}$ is O, S, $C(Z_{33})(Z_{34})$, $N(Z_{35})$, or $Si(Z_{36})(Z_{37})$;

$Z_{31}$ to $Z_{37}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a biphenyl group, a terphenyl group, and —$Si(Q_{33})(Q_{34})(Q_{35})$, wherein $Q_{33}$ to $Q_{35}$ are each independently selected from a $C_1$-$C_{10}$ alkyl group, a $C_1$-$C_{10}$ alkoxy group, a phenyl group, and a naphthyl group;

e2 may be 1 or 2;
e3 is an integer selected from 1 to 3;
e4 is an integer selected from 1 to 4;
e5 is an integer selected from 1 to 5;
e6 is an integer selected from 1 to 6;
e7 is an integer selected from 1 to 7;
e8 is an integer selected from 1 to 8;
e9 is an integer selected from 1 to 9; and
* is a binding site with an adjacent atom.

In some other embodiments, in Formulae 1, 2A, and 2B, $R_1$ to $R_6$ and $R_{11}$ to $R_{13}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, groups respectively represented by Formulae 6-1 to 6-43, groups respectively represented by Formulae 10-1 to 10-117, and —$Si(Q_3)(Q_4)(Q_5)$, wherein $Q_3$ to $Q_5$ may be each independently selected from a $C_1$-$C_{10}$ alkyl group, a $C_1$-$C_{10}$ alkoxy group, a phenyl group, and a naphthyl group. However, embodiments of the condensed cyclic compound are not limited thereto.
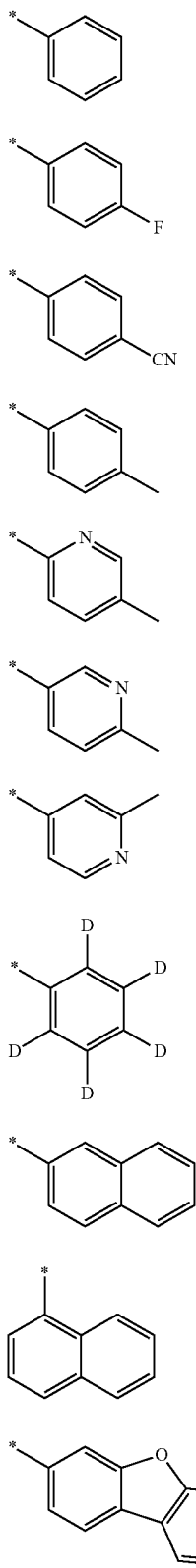
Formula 6-1
Formula 6-2
Formula 6-3
Formula 6-4
Formula 6-5
Formula 6-6
Formula 6-7
Formula 6-8
Formula 6-9
Formula 6-10
Formula 6-11
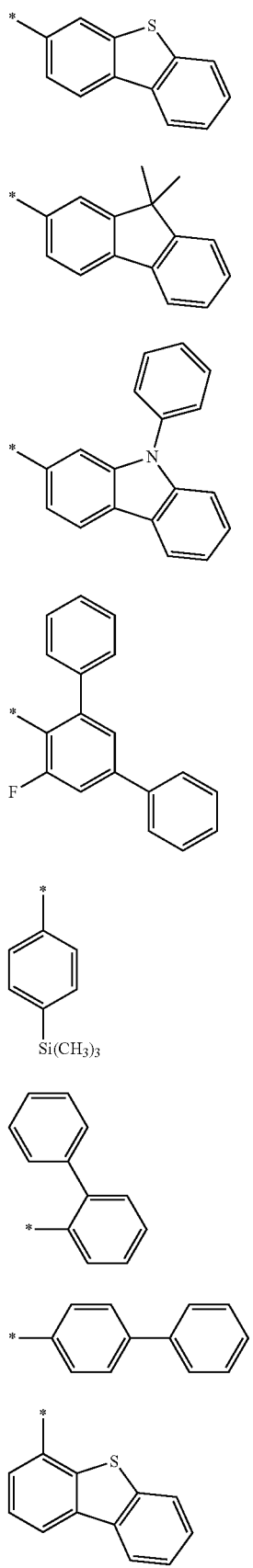
Formula 6-12
Formula 6-13
Formula 6-14
Formula 6-15
Formula 6-16
Formula 6-17
Formula 6-18
Formula 6-19

-continued

Formula 6-20

Formula 6-21

Formula 6-22

Formula 6-23

Formula 6-24

Formula 6-25

Formula 6-26

Formula 6-27

Formula 6-28

Formula 6-29

Formula 6-30

Formula 6-31

Formuka 6-32

Formula 6-33

Formula 6-34

Formula 6-35

Formula 6-36

Formula 6-37

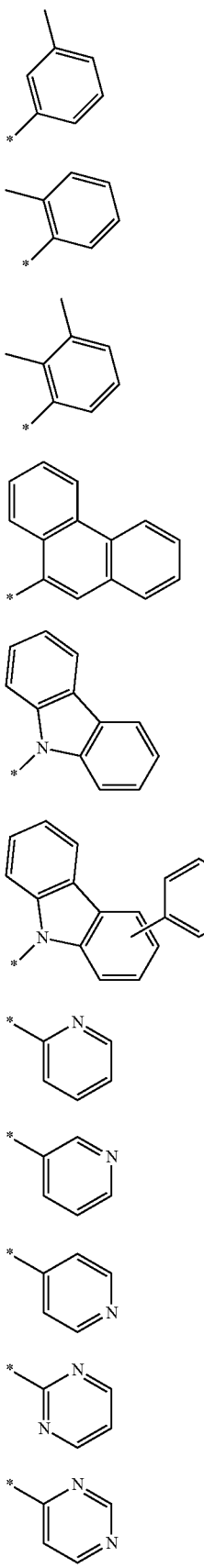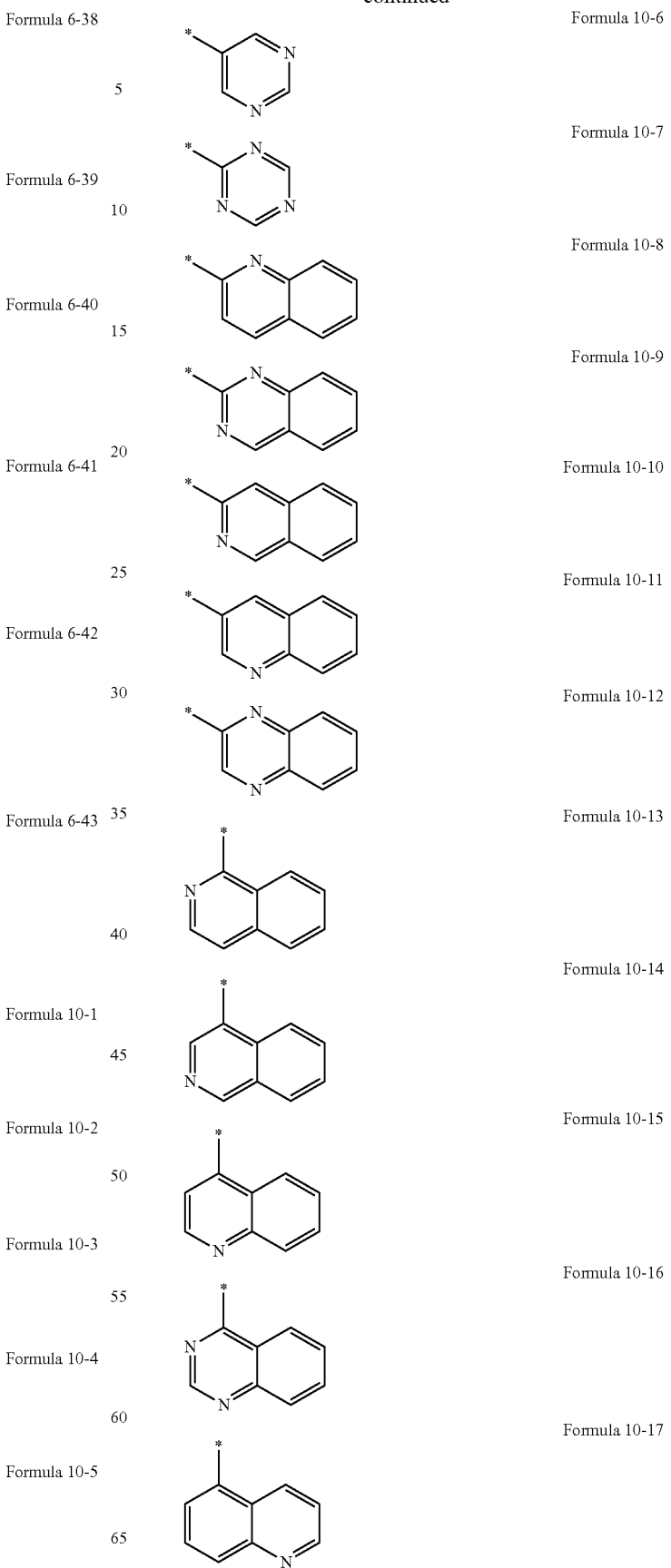

Formula 10-18
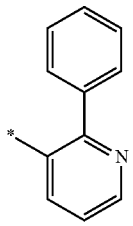
Formula 10-19
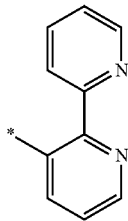
Formula 10-20
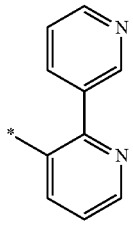
Formula 10-21
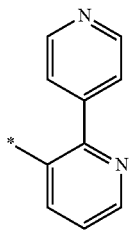
Formula 10-22
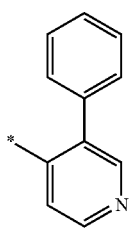
Formula 10-23
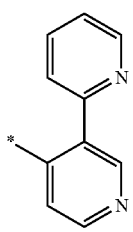
Formula 10-24
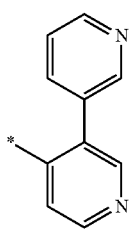
Formula 10-25
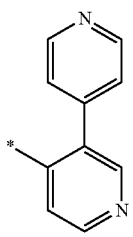
Formula 1-26
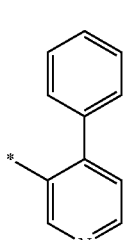
Formula 10-27
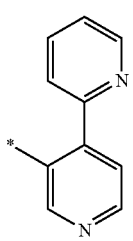
Formula 10-28
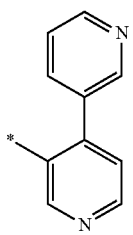
Formula 10-29
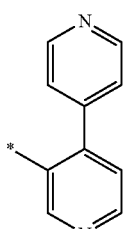
Formula 10-30
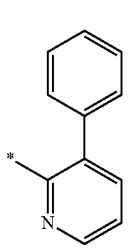

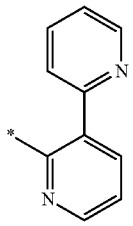
Formula 10-31
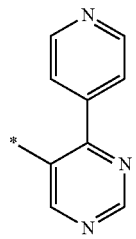
Formula 10-37
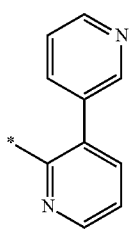
Formula 10-32
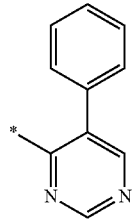
Formula 10-38
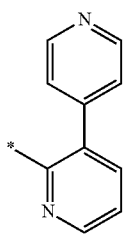
Formula 10-33
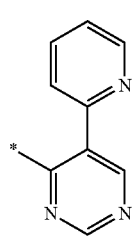
Formula 10-39
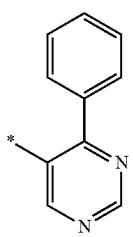
Formula 10-34
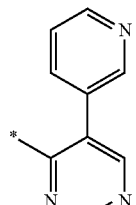
Formula 10-40
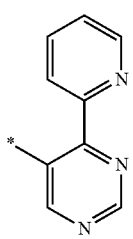
Formula 10-35
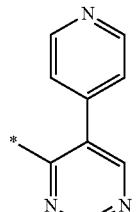
Formula 10-41
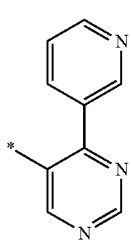
Formula 10-36
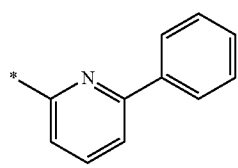
Formula 10-42
Formula 10-43

Formula 10-44
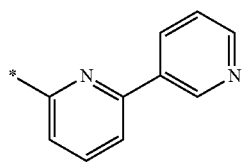
Formula 10-45
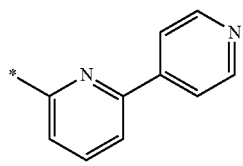
Formula 10-46
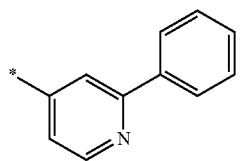
Formula 10-47
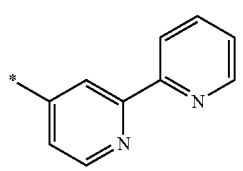
Formula 10-48
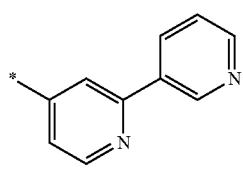
Formula 10-49
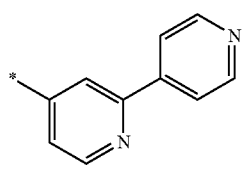
Formula 10-50
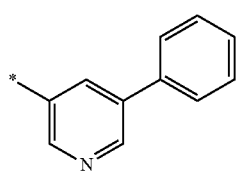
Formula 10-51
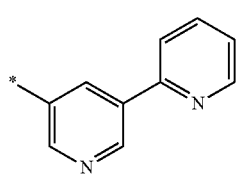
Formula 10-52
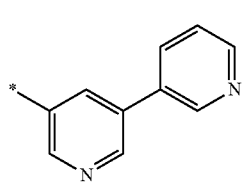
Formula 10-53
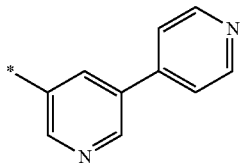
Formula 10-54
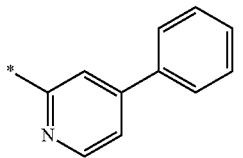
Formula 10-55
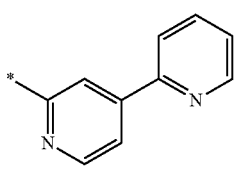
Formula 10-56
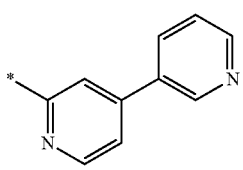
Formula 10-57
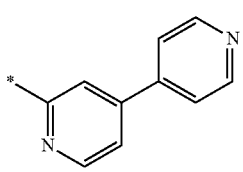
Formula 10-58
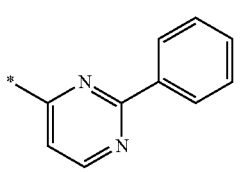
Formula 10-59
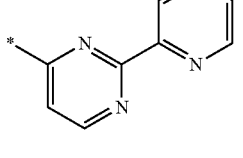
Formula 10-60
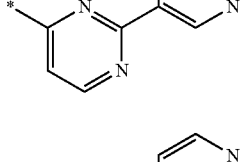
Formula 10-61
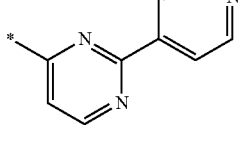

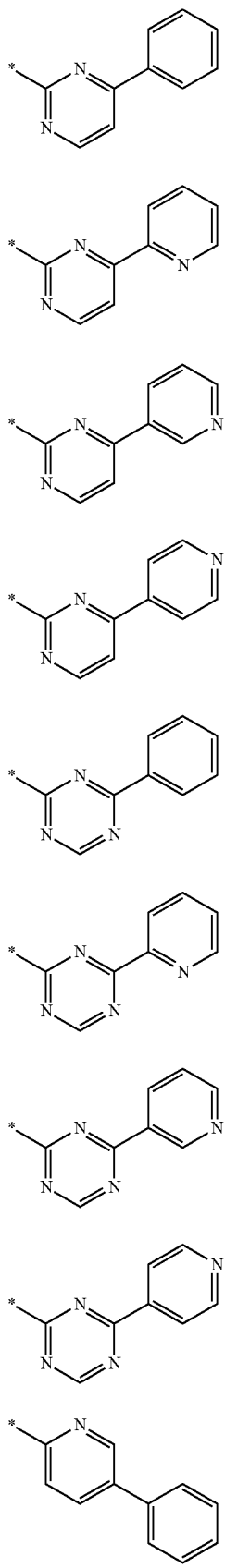
Formula 10-62
Formula 10-63
Formula 10-64
Formula 10-65
Formula 10-66
Formula 10-67
Formula 10-68
Formula 10-69
Formula 10-70
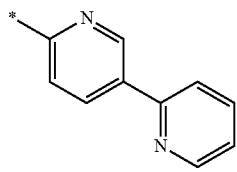
Formula 10-71
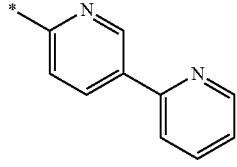
Formula 10-72
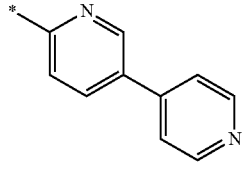
Formula 10-73
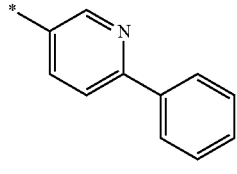
Formula 10-74
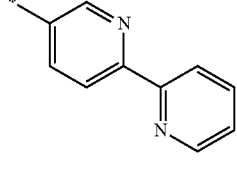
Formula 10-75
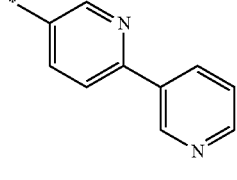
Formula 10-76
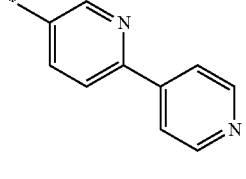
Formula 10-77
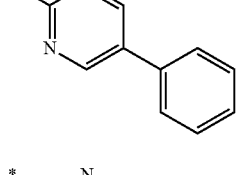
Formula 10-78
Formula 10-79

Formula 10-80
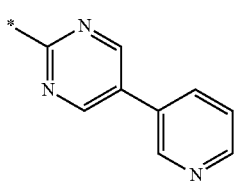
Formula 10-87
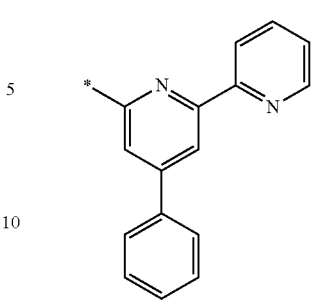
Formula 10-81
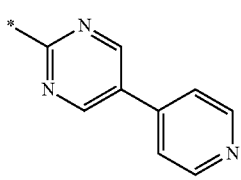
Formula 10-82
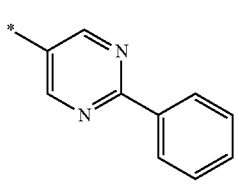
Formula 10-88
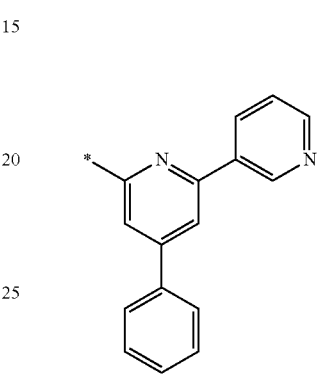
Formula 10-83
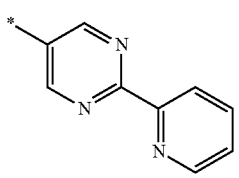
Formula 10-89
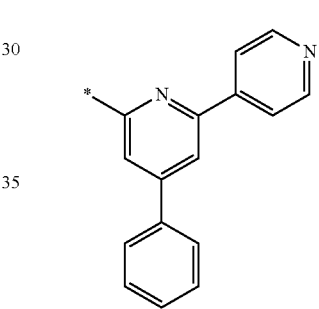
Formula 10-84
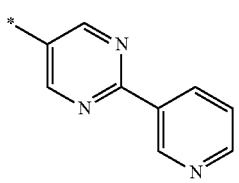
Formula 10-85
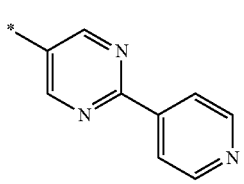
Formula 10-90
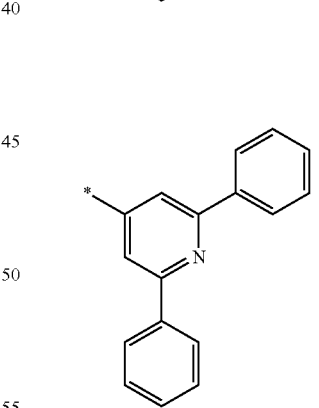
Formula 10-86
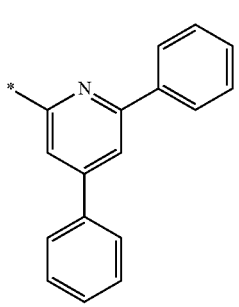
Formula 10-91
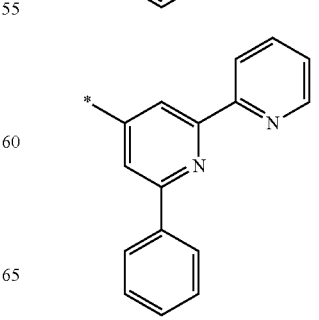

Formula 10-92
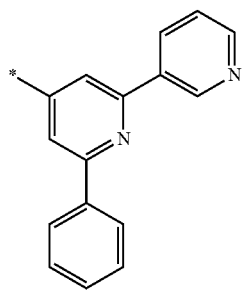
Formula 10-93
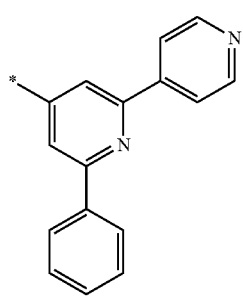
Formula 10-94
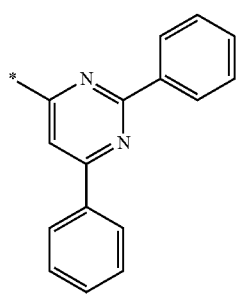
Formula 10-95
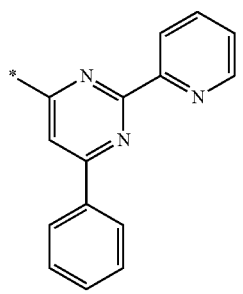
Formula 10-96
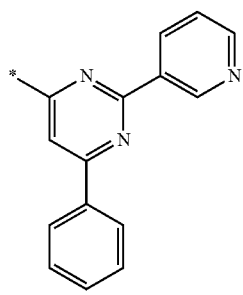
Formula 10-97
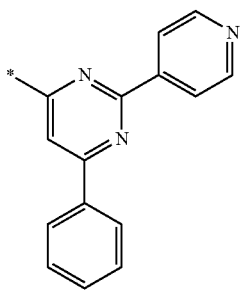
Formula 10-98
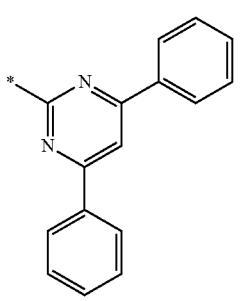
Formula 10-99
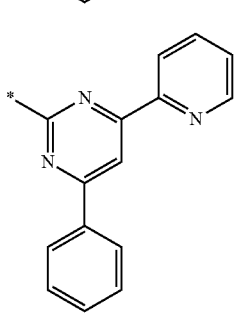
Formula 10-100
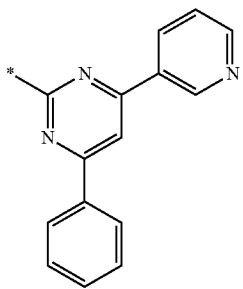
Formula 10-101
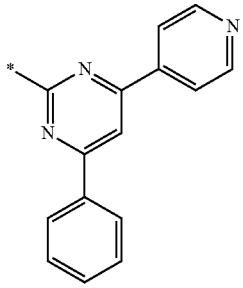

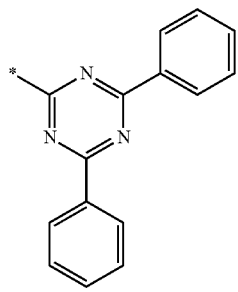
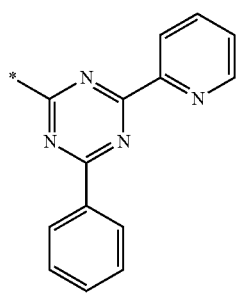
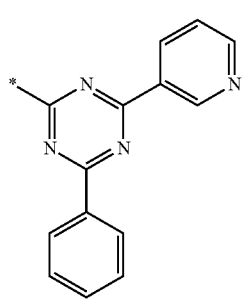
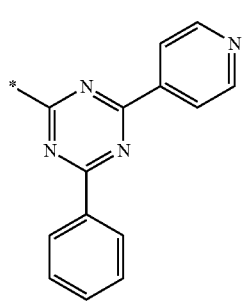
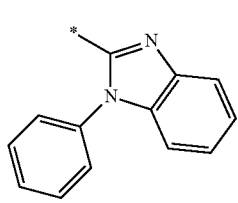
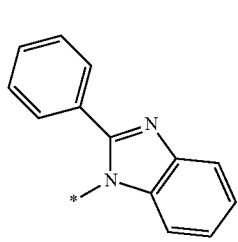
Formula 10-102
Formula 10-103
Formula 10-104
Formula 10-105
Formula 10-106
Formula 10-107
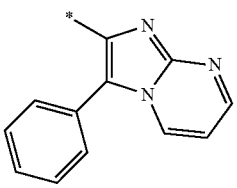
Formula 10-108
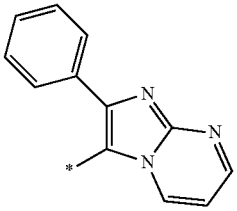
Formula 10-109
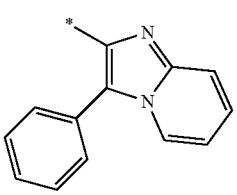
Formula 10-110
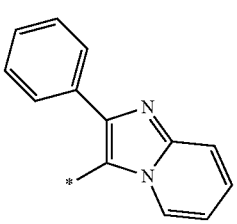
Formula 10-111
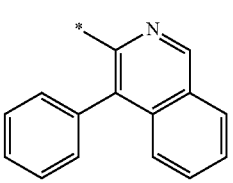
Formula 10-112
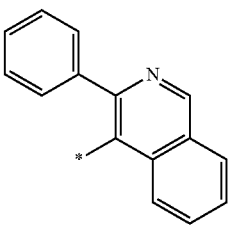
Formula 10-113
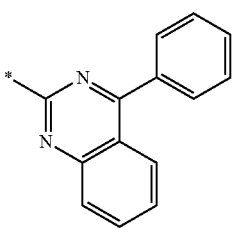
Formula 10-114

-continued

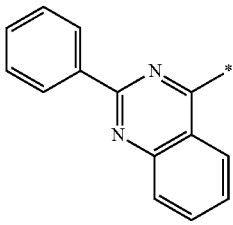

Formula 10-115

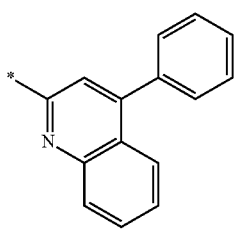

Formula 10-116

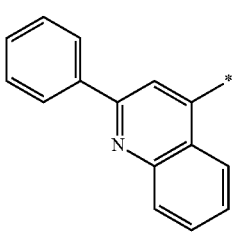

Formula 10-117

In Formulae 6-1 to 6-43 and Formulae 10-1 to 10-117, * is a binding site with an adjacent atom.

In some embodiments, in Formulae 1, 2A, and 2B, $R_3$ to $R_6$, and $R_{13}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, and —Si($Q_3$)($Q_4$)($Q_5$); and $R_1$, $R_2$, $R_{11}$ and $R_{12}$ may be each independently selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group (for example, groups respectively represented by Formulae 5-1 to 5-75, and in some embodiments, groups respectively represented by Formulae 6-1 to 6-43 and Formulae 10-1 to 10-117).

In some embodiments, in Formulae 1, 2A, and 2B, $R_3$ to $R_6$, and $R_{13}$ may be a hydrogen; and $R_1$, $R_2$, $R_{11}$, and $R_{12}$ may be each independently selected from groups respectively represented by Formulae 5-1 to 5-75 (for example, the groups respectively represented by Formulae 6-1 to 6-43 and the groups respectively represented by Formulae 10-1 to 10-117). However, embodiments of the condensed cyclic compound are not limited thereto.

In Formulae 1, 2A, and 2B, b1, b2, b5, b6, b11, and b12 may be each independently an integer selected from 0 to 4; b3 and b4 may be each independently an integer selected from 0 to 6; and b13 may be 0, 1, or 2.

For example, in Formulae 1, 2A, and 2B, b1, b2, b11, and b12 may be each independently 0, 1, or 2, and in some embodiments, 1 or 2.

In some other embodiments, in Formulae 1, 2A, and 2B, b1, b2, b11, and b12 may each be 1. However, embodiments of the condensed cyclic compound are not limited thereto.

In Formulae 1, 2A, and 2B, b3 to b6, and b13 may be each independently 0, 1, or 2, and in some embodiments, 0 or 1. However, embodiments of the condensed cyclic compound are not limited thereto.

In Formula 1, c1 and c2 may be each independently an integer selected from 0 to 4, wherein c1+c2 may be 1 or greater. In some embodiments, Formula 1 has at least one selected from the group represented by *-[($L_1$)$_{a1}$-($R_1$)$_{b1}$] and the group represented by *-[($L_2$)$_{a2}$-($R_2$)$_{b2}$].

In some embodiments, in Formula 1, c1+c2 may be 1 or 2.

In some embodiments, in Formula 1, c1 may be 1, and c2 may be 0; c1 may be 1, and c2 may be 1; or c1 may be 0, and c2 may be 1. However, embodiments of the condensed cyclic compound are not limited thereto.

In some embodiments, the condensed cyclic compound represented by Formula 1 may be a compound represented by any one of Formulae 1A to 1E.

Formula 1A

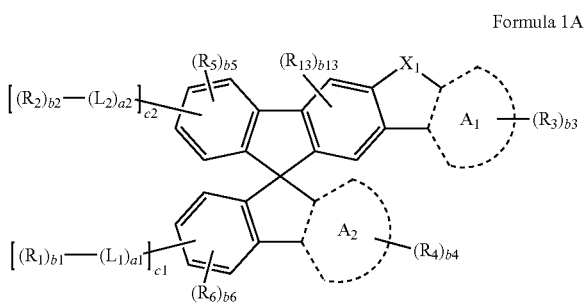

Formula 1B

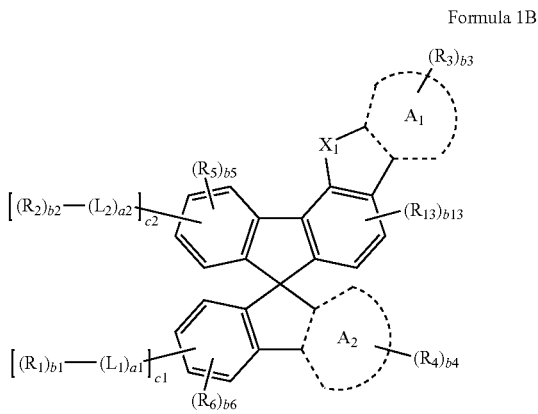

-continued

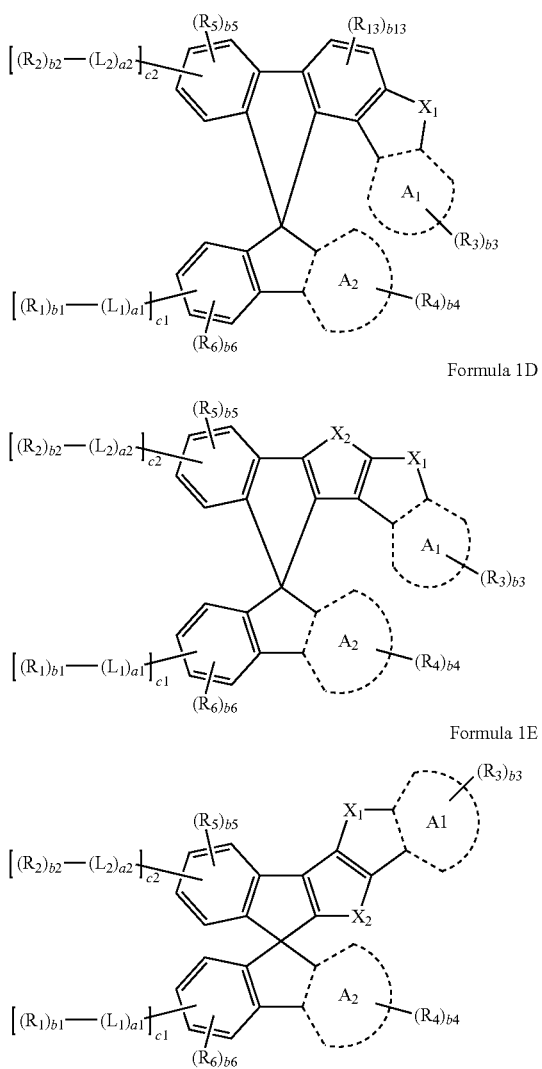

Formula 1C

Formula 1D

Formula 1E

In Formulae 1A to 1E, $A_1$ ring, $A_2$ ring, $X_1$, $X_2$, $L_1$, $L_2$, a1, a2, $R_1$ to $R_6$, $R_{13}$, b1 to b6, b13, c1, and c2 may be defined the same as those defined herein.

For example, in Formulae 1A to 1E, $A_1$ ring may be a benzene or a pyridine, and $A_2$ ring may be selected from a benzene, a naphthalene, a pyridine, a quinoline, and an isoquinoline; or $A_1$ ring may be selected from a naphthalene, a quinoline, and an isoquinoline, and $A_2$ ring may be a benzene or a pyridine;

$X_1$ and $X_2$ may be each independently O or S;

$L_1$ and $L_2$ may be each independently selected from the groups respectively represented by Formulae 3-8, 3-9, 3-25, and 3-35 to 3-41 (for example, the groups respectively represented by Formulae 4-11, 4-13, 4-27, and 4-29 to 4-35);

a1 and a2 may be each independently 1 or 2;

$R_1$ and $R_2$ may be each independently selected from the groups respectively represented by Formulae 5-1 to 5-75 (for example, the groups respectively represented by Formulae 6-1 to 6-43 and the groups respectively represented by Formulae 10-1 to 10-117);

b1 and b2 may be each independently 1 or 2;

$R_3$ to $R_6$, and $R_{13}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, and —Si($Q_3$)($Q_4$)($Q_5$), wherein $Q_3$ to $Q_5$ may be each independently selected from a $C_1$-$C_{10}$ alkyl group, a $C_1$-$C_{10}$ alkoxy group, a phenyl group, and a naphthyl group;

b3 to b6, and b13 may be each independently 0, 1, or 2;

c1 may be 1 and c2 may be 0; c1 may be 1 and c2 may be 1; or c1 may be 0 and c2 may be 1.

In some embodiments, the condensed cyclic compound represented by Formula 1 may be a compound represented by any one of Formulae 1-1 to 1-7.

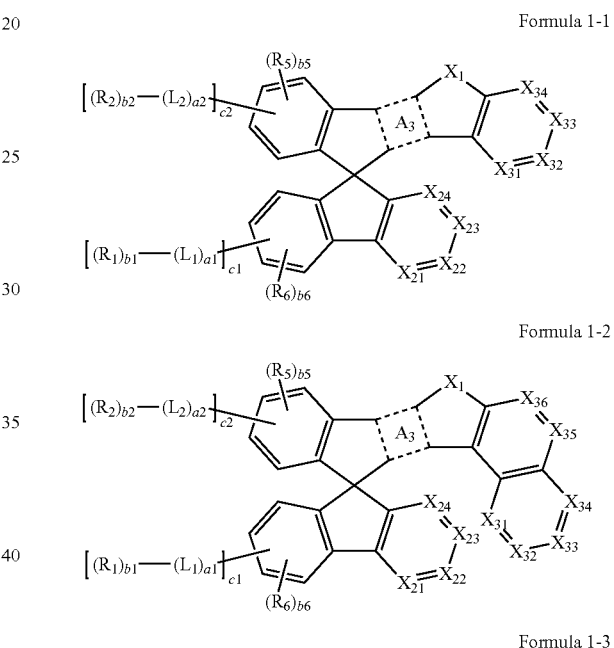

Formula 1-1

Formula 1-2

Formula 1-3

Formula 1-4

Formula 1-5

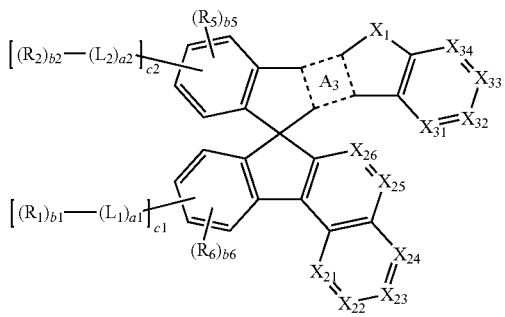

Formula 1-6

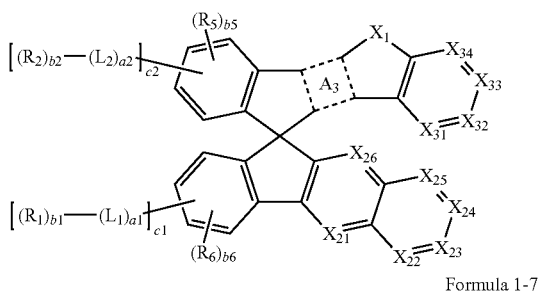

Formula 1-7

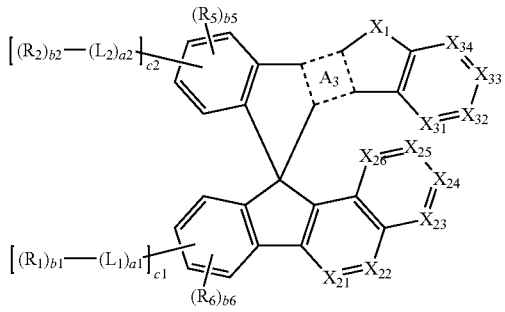

In Formulae 1-1 to 1-7, $A_3$ ring, $X_1$, $L_1$, $L_2$, a1, a2, $R_1$, $R_2$, $R_5$, $R_6$, b1, b2, b5, b6, c1, and c2 may be defined the same as those described herein;

$X_{21}$ may be N or $C(R_{21})$; $X_{22}$ may be N or $C(R_{22})$; $X_{23}$ may be N or $C(R_{23})$; $X_{24}$ may be N or $C(R_{24})$; $X_{25}$ may be N or $C(R_{25})$; $X_{26}$ may be N or $C(R_{26})$; $X_{31}$ may be N or $C(R_{31})$; $X_{32}$ may be N or $C(R_{32})$; $X_{33}$ may be N or $C(R_{33})$; $X_{34}$ may be N or $C(R_{34})$; $X_{35}$ may be N or $C(R_{35})$; $X_{36}$ may be N or $C(R_{36})$;

$R_{21}$ to $R_{26}$ may be defined the same as $R_3$ described in connection with Formula 1; and $R_{31}$ to $R_{36}$ may be defined the same as $R_4$ described in connection with Formula 1.

In some embodiments, none, one, or two selected from $X_{21}$ to $X_{24}$ and $X_{31}$ to $X_{34}$ in Formula 1-1 may be N; none, one, or two selected from $X_{21}$ to $X_{24}$ and $X_{31}$ to $X_{36}$ in Formulae 1-2 to 1-4 may be N; and none, one, or two selected from $X_{21}$ to $X_{26}$ and $X_{31}$ to $X_{34}$ in Formulae 1-5 to 1-7 may be N.

In some embodiments, none or one of $X_{21}$ to $X_{24}$ in Formulae 1-1 to 1-4 may be N; none or one of $X_{31}$ to $X_{34}$ in Formulae 1-1 and 1-5 to 1-7 may be N; none or one of $X_{21}$ to $X_{26}$ in Formulae 1-5 to 1-7 may be N; and none or one of $X_{31}$ to $X_{36}$ in Formulae 1-2 to 1-4 may be N.

For example, the $A_3$ ring in Formulae 1-1 to 1-7 may be a group represented by Formula 2A.

In some embodiments, in Formulae 1-1 to 1-7, $X_1$ and $X_2$ may be each independently O or S;

$L_1$ and $L_2$ may be each independently selected from the groups respectively represented by Formulae 3-8, 3-9, 3-25, and Formulae 3-35 to 3-41 (for example, the groups respectively represented by Formulae 4-11, 4-13, 4-27, and 4-29 to 4-35);

a1 and a2 may be each independently 1 or 2;

$R_1$ and $R_2$ may be each independently selected from the groups respectively represented by Formulae 5-1 to 5-75 (for example, the groups respectively represented by Formulae 6-1 to 6-43 and the groups respectively represented by Formulae 10-1 to 10-117);

b1 and b2 may be each independently 1 or 2;

$R_{21}$ to $R_{26}$, $R_{31}$ to $R_{36}$, $R_5$, and $R_6$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, and —Si$(Q_3)(Q_4)(Q_5)$, wherein $Q_3$ to $Q_5$ may be each independently selected from a $C_1$-$C_{10}$ alkyl group, a $C_1$-$C_{10}$ alkoxy group, a phenyl group, and a naphthyl group;

b5 and b6 may be each independently 0, 1, or 2;

c1 may be 1 and c2 may be 0, c1 may 1 and c2 may be 1, or c1 may b20 and c2 may be 1.

In some embodiments, the condensed cyclic compound represented by Formula 1 may be a compound represented by one of Formulae 1(1) to 1(24). However, embodiments of the condensed cyclic compound are not limited thereto.

Formula 1(1)

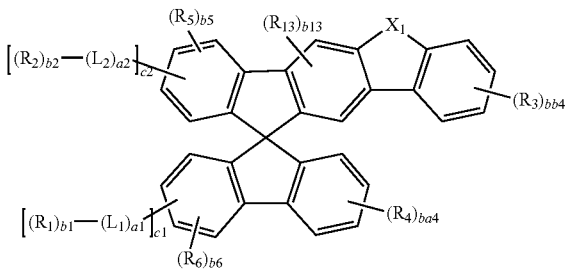

Formula 1(2)

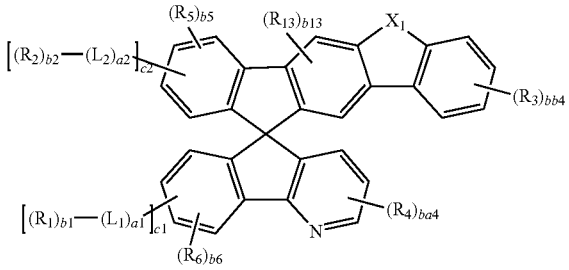

Formula 1(3)
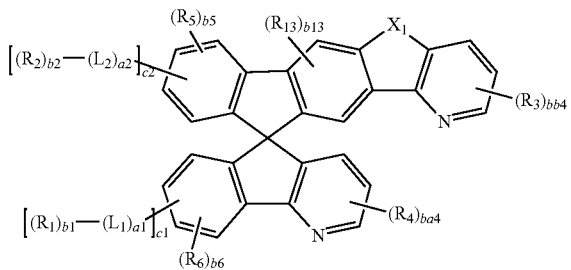
Formula 1(8)
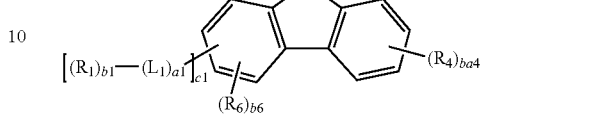
Formula 1(4)
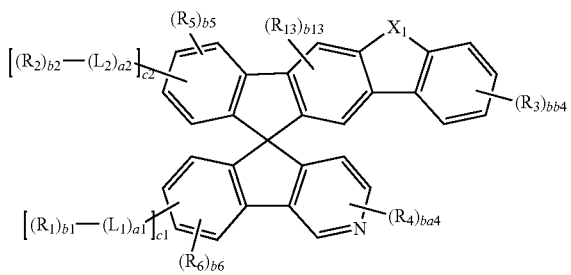
Formula 1(9)
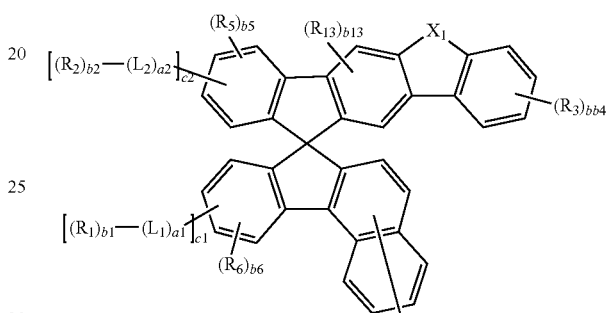
Formula 1(5)
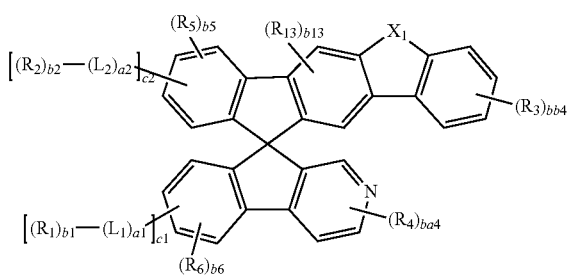
Formula 1(10)
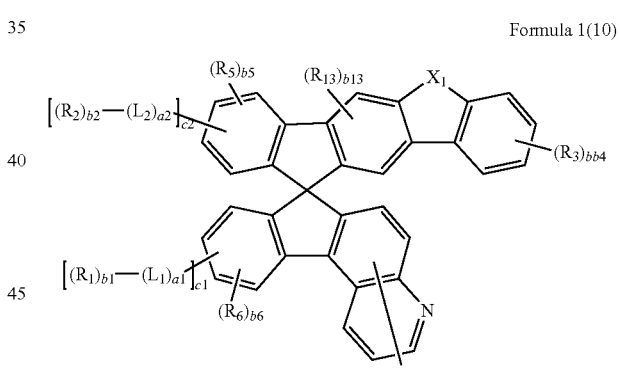
Formula 1(6)
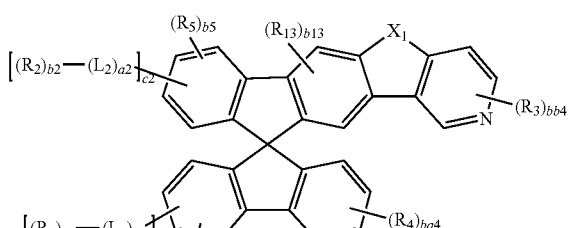
Formula 1(7)
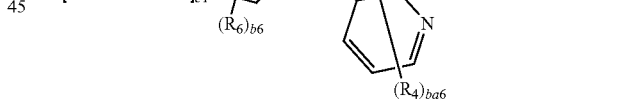
Formula 1(11)
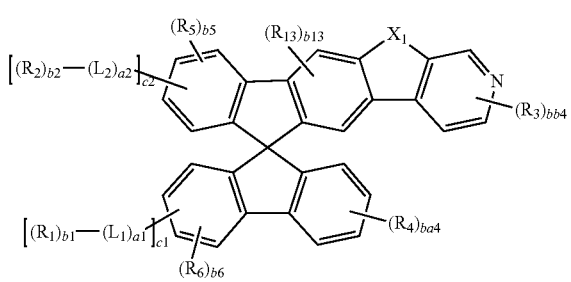
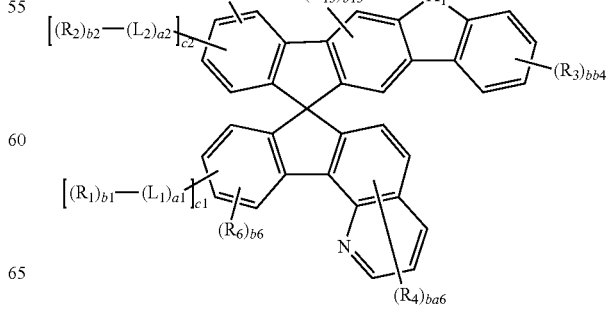

-continued
Formula 1(12)
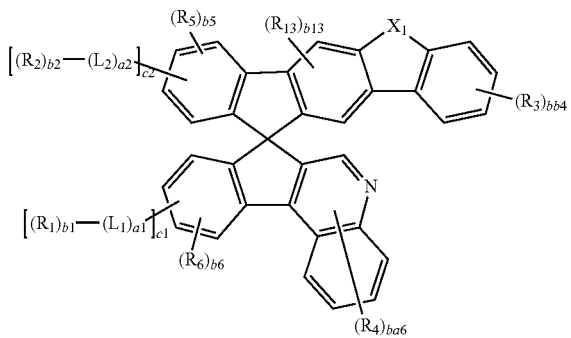
Formula 1(13)
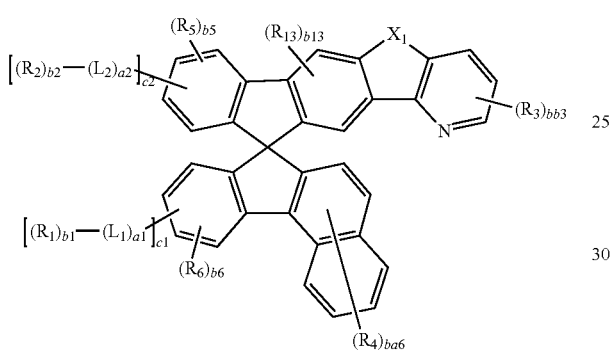
Formula 1(14)
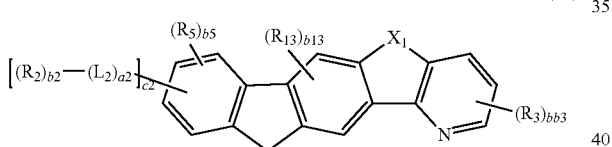
Formula 1(15)
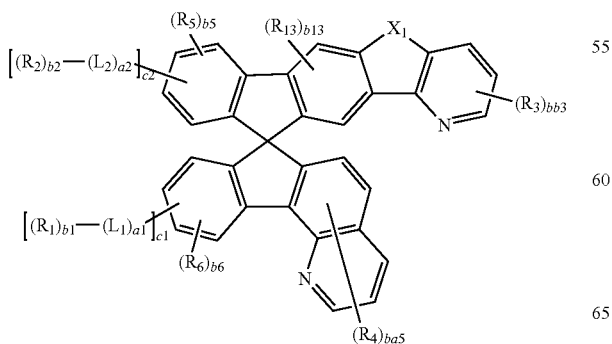
Formula 1(16)
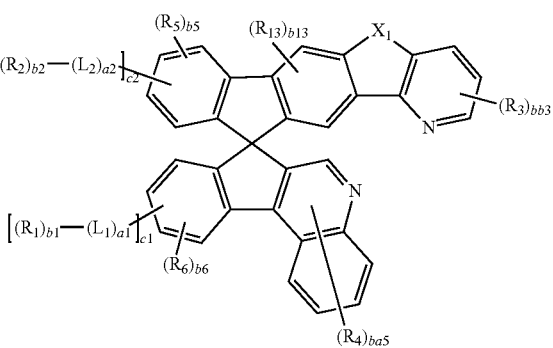
Formula 1(17)
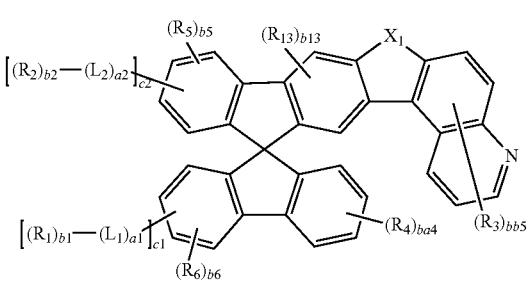
Formula 1(18)
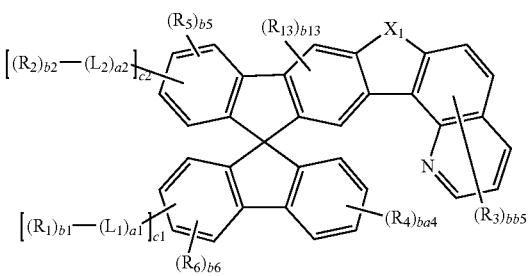
Formula 1(19)
Formula 1(20)
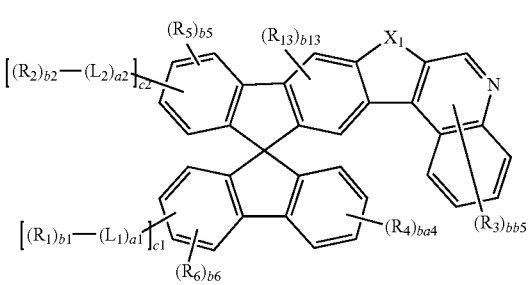

-continued

Formula 1(21)

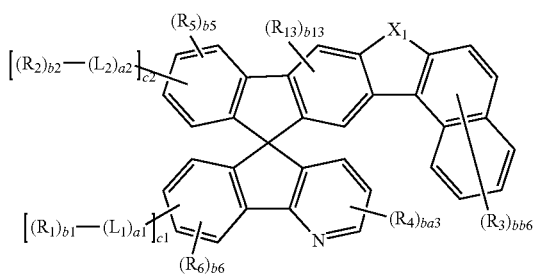

Formula 1(22)

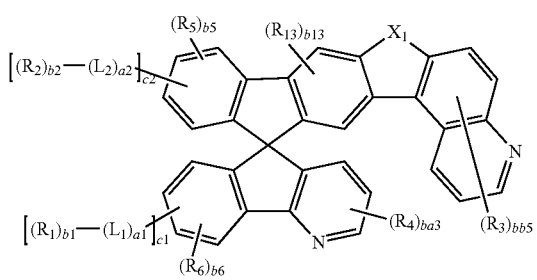

Formula 1(23)

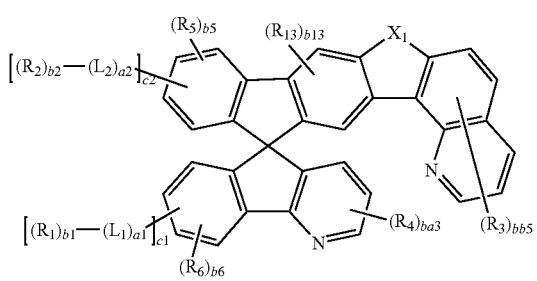

Formula 1(24)

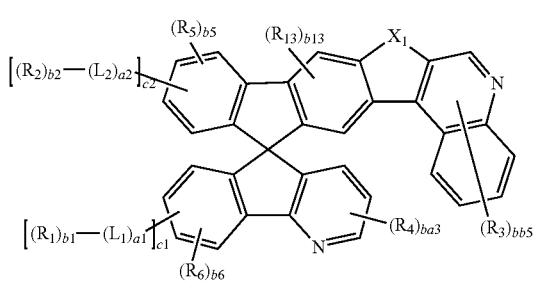

In Formulae 1(1) to 1(24), $X_1$, $L_1$, $L_2$, a1, a2, $R_1$ to $R_6$, $R_{13}$, b1 to b6, b13, c1, and c2 may be defined the same as those described herein;

ba3 and bb3 may be each independently an integer selected from 0 to 3;

ba4 and bb4 may be each independently an integer selected from 0 to 4;

ba5 and bb5 may be each independently an integer selected from 0 to 5; and ba6 and bb6 may be each independently an integer selected from 0 to 6.

In some embodiments, in Formulae 1(1) to 1(24), $X_1$ and $X_2$ may be each independently O or S;

$L_1$ and $L_2$ may be each independently selected from the groups respectively represented by Formulae 3-8, 3-9, and 3-25 and Formulae 3-35 to 3-41 (for example, the groups respectively represented by Formula 4-11, 4-13, and 4-27, and Formulae 4-29 to 4-35);

a1 and a2 may be each independently 1 or 2;

$R_1$ and $R_2$ may be each independently selected from the groups respectively represented by Formulae 5-1 to 5-75 (for example, the groups respectively represented by Formulae 6-1 to 6-43 and Formulae 10-1 to 10-117);

b1 and b2 may be each independently 1 or 2;

$R_3$ to $R_6$, and $R_{13}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, and —Si($Q_3$)($Q_4$)($Q_5$), wherein $Q_3$ to $Q_5$ may be each independently selected from a $C_1$-$C_{10}$ alkyl group, a $C_1$-$C_{10}$ alkoxy group, a phenyl group, and a naphthyl group;

ba3, bb3, ba4, bb4, ba5, bb5, ba6, bb6, b5, and b6 may be each independently 0, 1, or 2;

c1 may be 1 and c2 may be 0, c1 may be 1 and c2 may be 1, or c1 may be 0 and c2 may be 1.

In some embodiments, the condensed cyclic compound represented by Formula 1 may be a compound represented by one of Formulae 1A-1 to 1A-3. However, embodiments of the condensed cyclic compound are not limited thereto.

Formula 1A-1

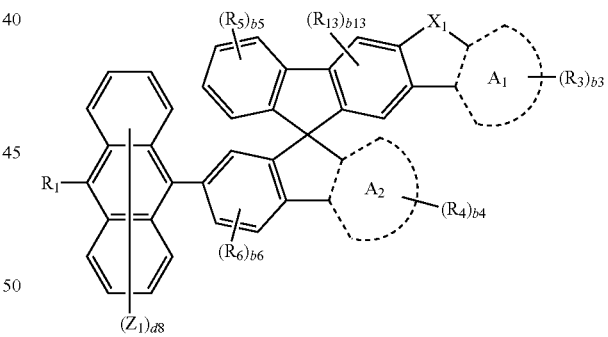

Formula 1A-2

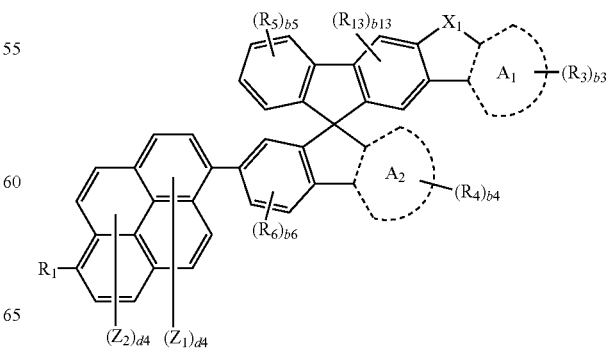

Formula 1A-3

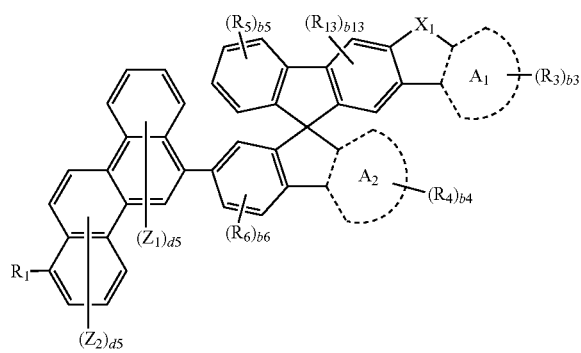

In Formulae 1A-1 to 1A-3, the $A_1$ ring, the $A_2$ ring, $X_1$, $L_{11}$, $L_{12}$, a11, a12, $R_1$, $R_3$ to $R_6$, $R_{11}$ to $R_{13}$, b3 to b6, b11 to b13, $Z_1$, $Z_2$, d4, d5, d8, c1, and c2 may be defined the same as those described herein.

For example, in Formulae 1A-1 to 1A-3,

The $A_1$ ring and the $A_2$ ring may be each independently selected from a benzene, a naphthalene, a pyridine, a quinoline, and an isoquinoline;

$X_1$ may be O or S;

$R_1$ may be selected from the groups represented by Formulae 5-1 to 5-75 (for example, the groups respectively represented by Formulae 6-1 to 6-43 and Formulae 10-1 to 10-117);

$R_3$ to $R_6$, $R_{13}$, $Z_1$, and $Z_2$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, and a naphthyl group; and b3 to b6, b13, d4, and d5 may be each independently 0, 1, or 2. However, embodiments of the condensed cyclic compound are not limited thereto.

In some embodiments, the condensed cyclic compound represented by Formula 1 may be one of Compounds 1 to 60. However, embodiments of the condensed cyclic compound are not limited thereto.

2

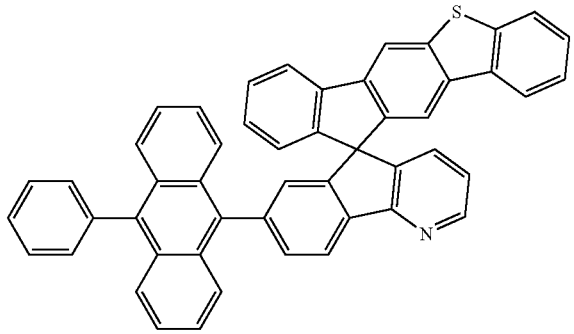

3

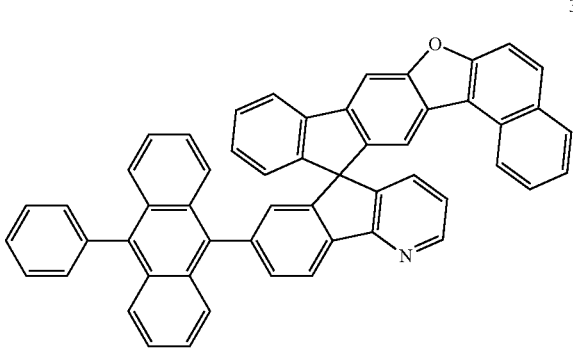

4

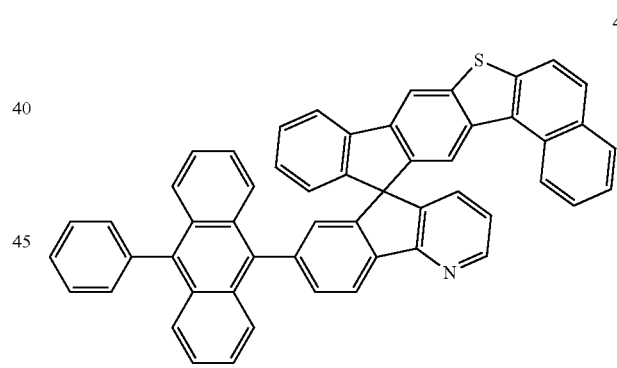

1

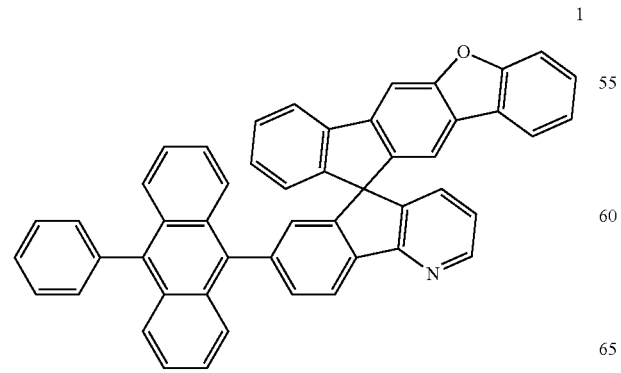

5

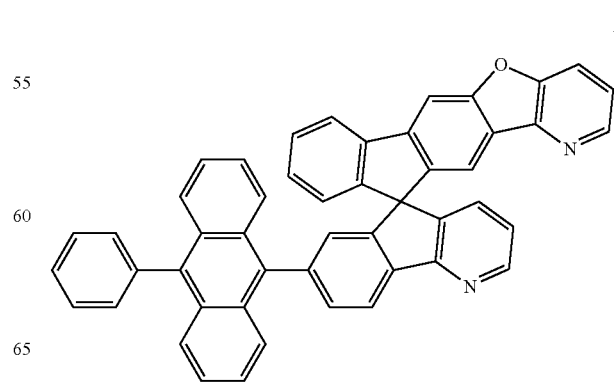

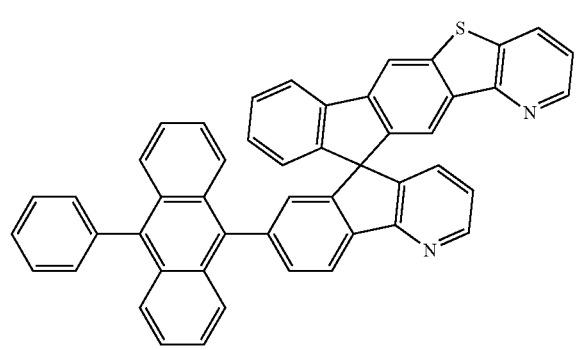
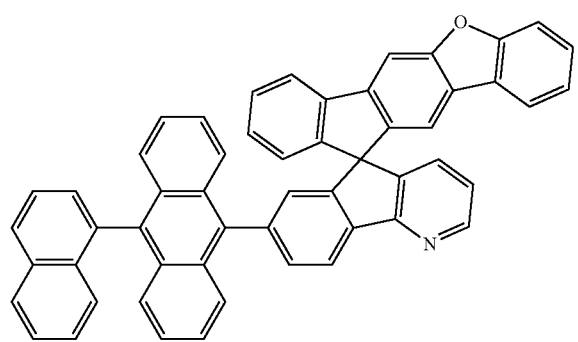
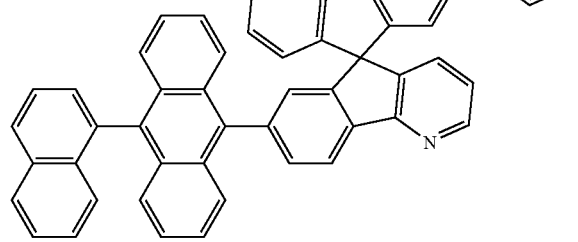
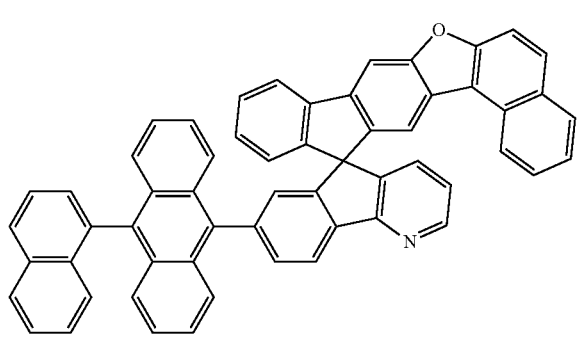
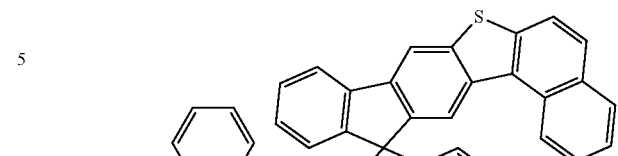

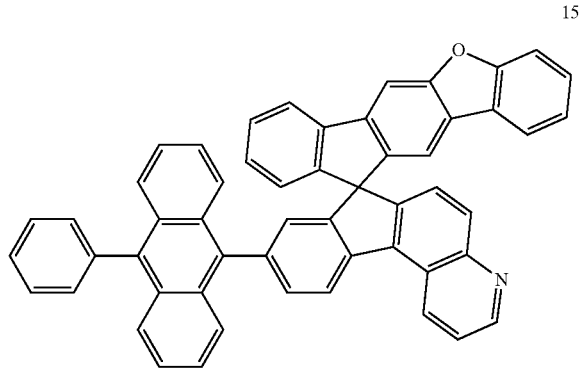
15
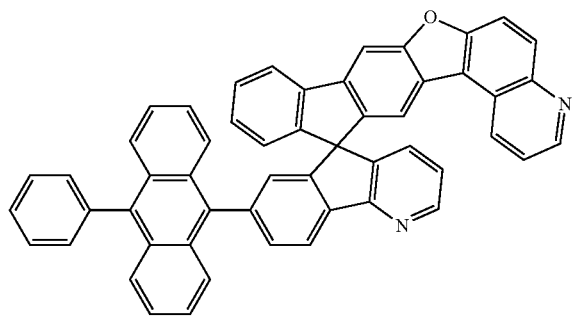
16
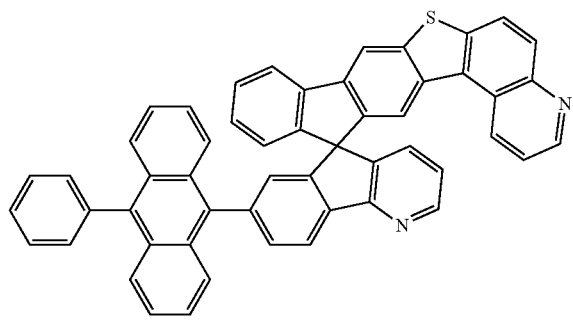
17
18
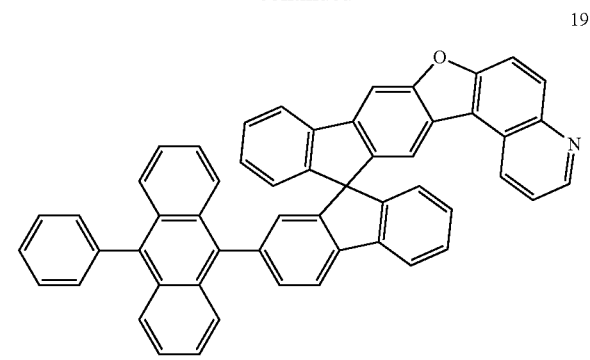
19
20
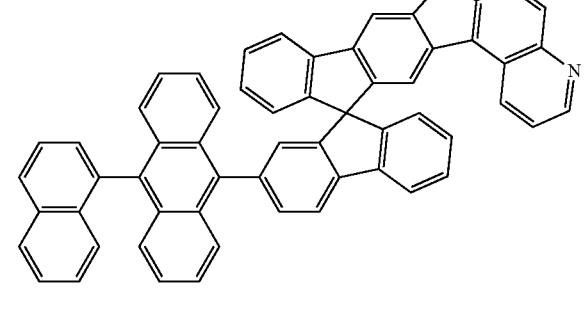
21
22

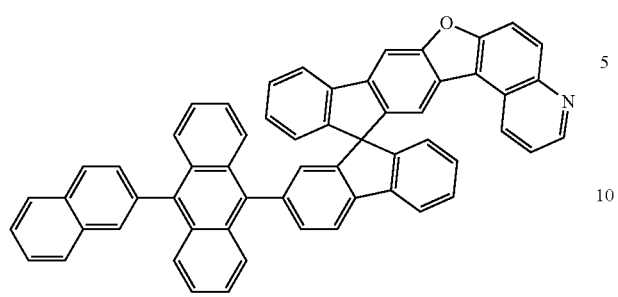
23
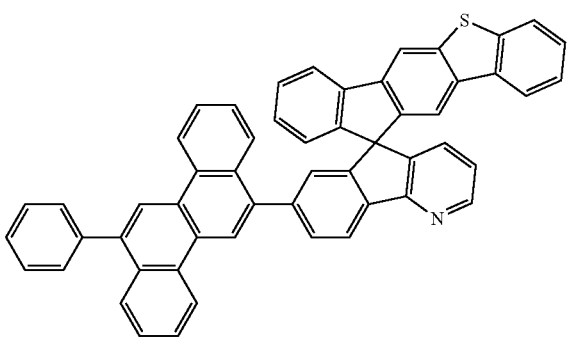
28
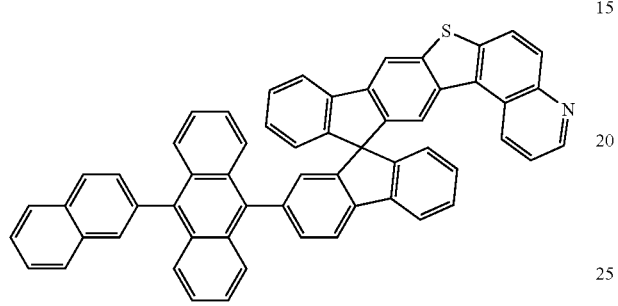
24
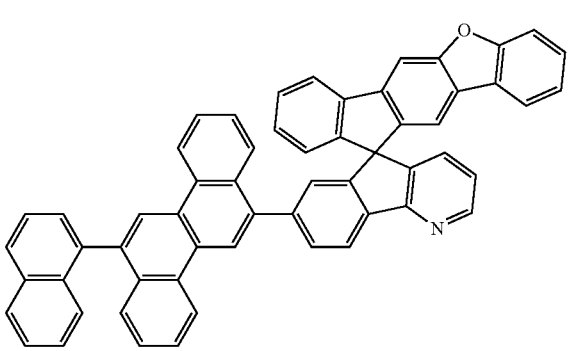
29
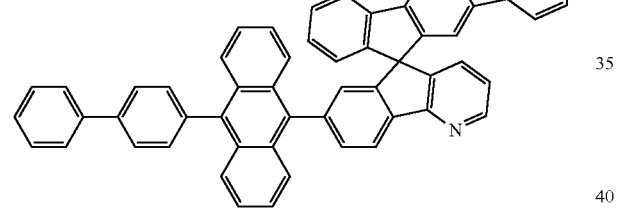
25
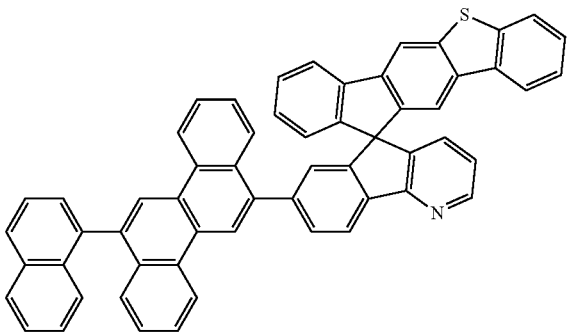
30
26
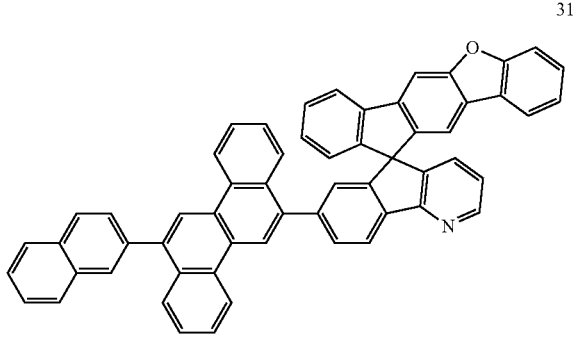
31
27

-continued
32
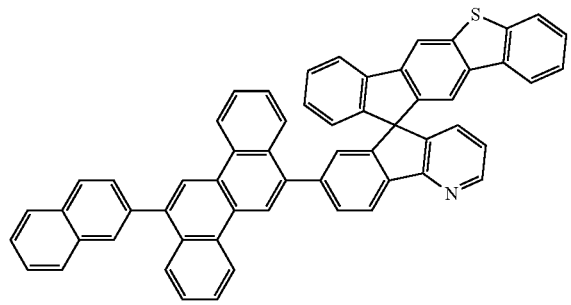
33
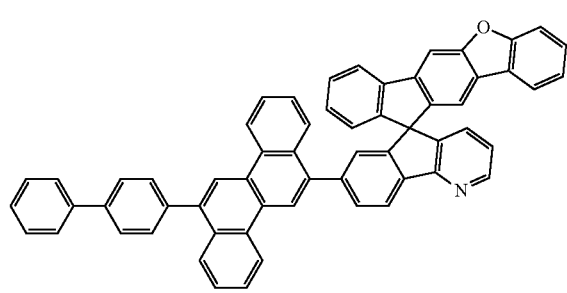
34
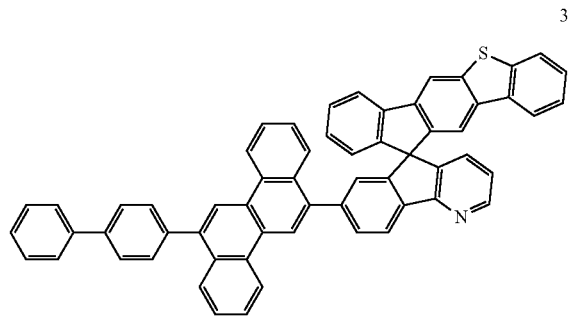
35
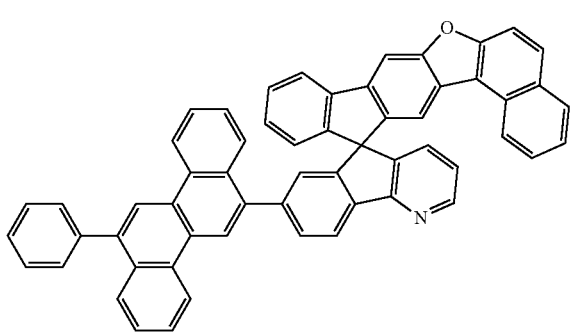
36
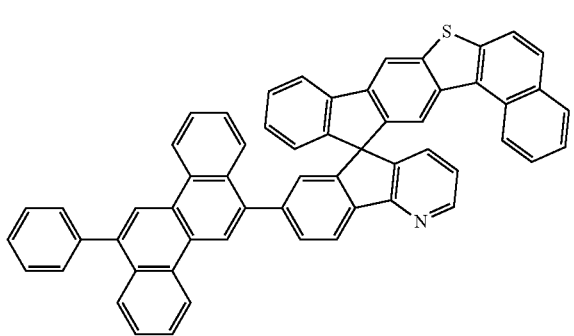
-continued
37
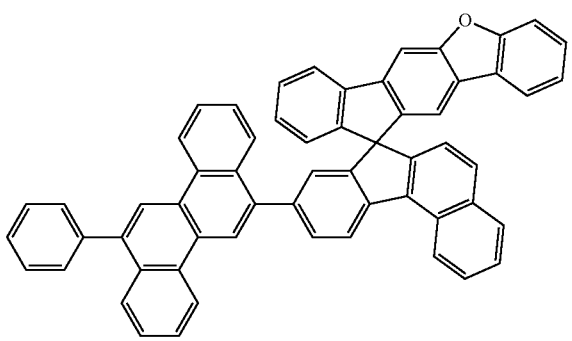
38
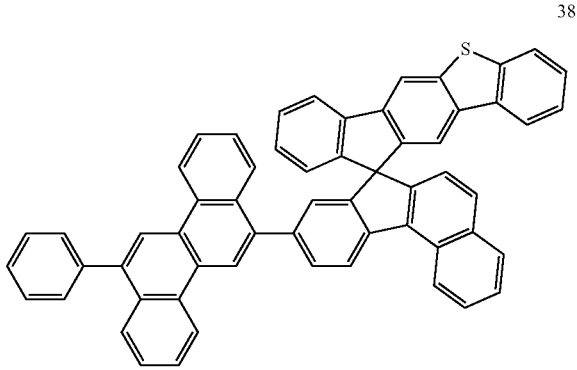
39
40
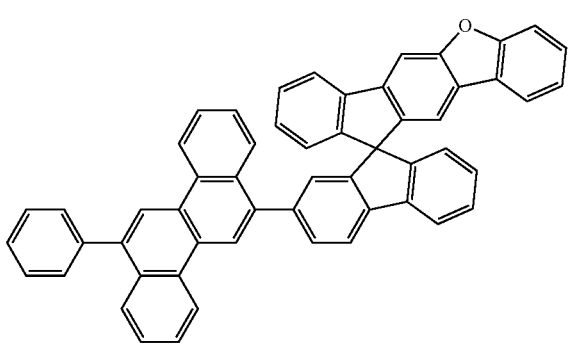

41
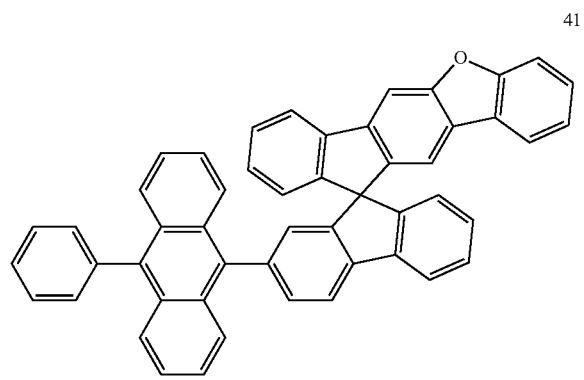
45
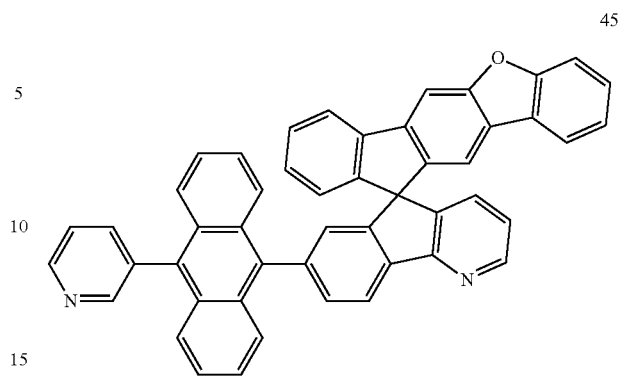
42
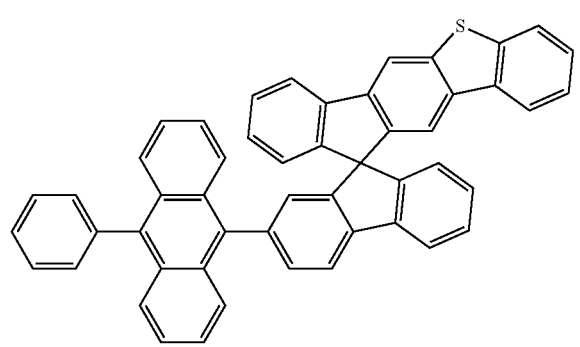
46
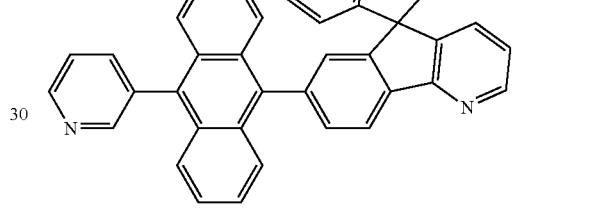
43
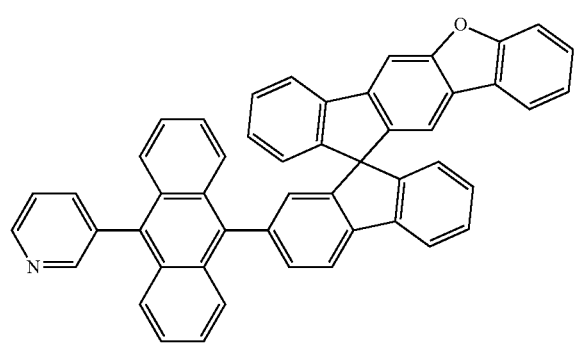
47
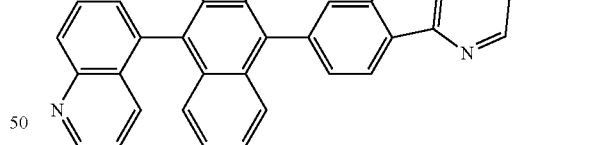
44
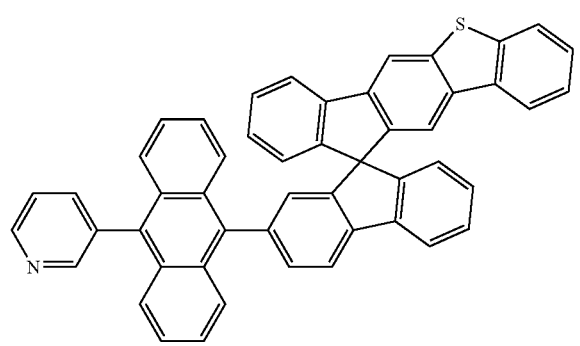
48
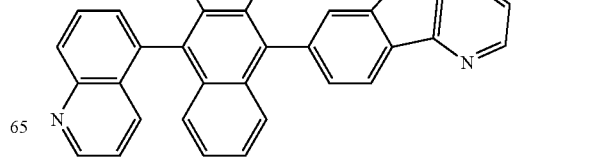

-continued
49
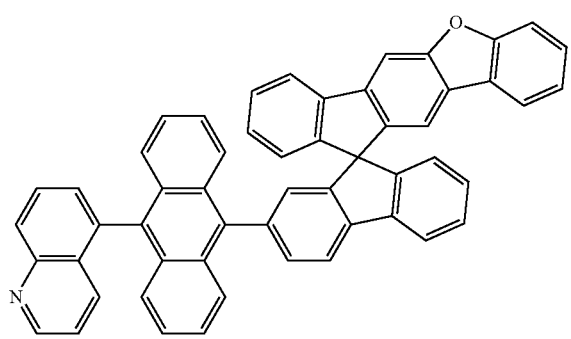
50
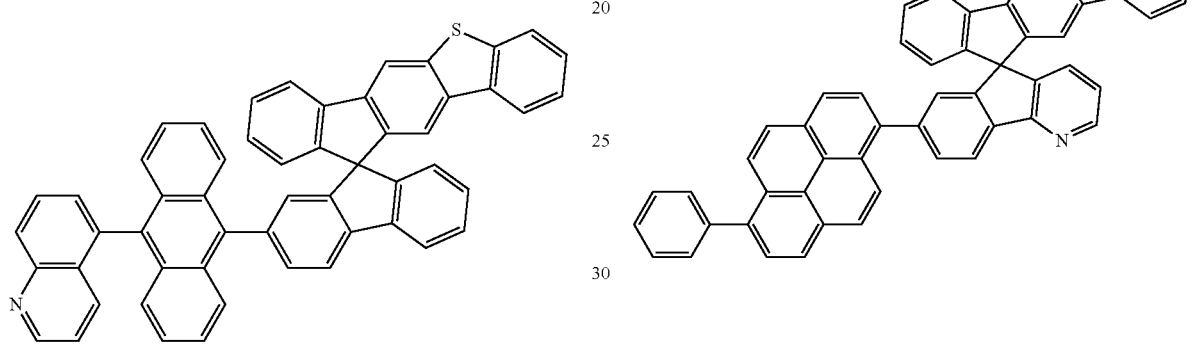
51
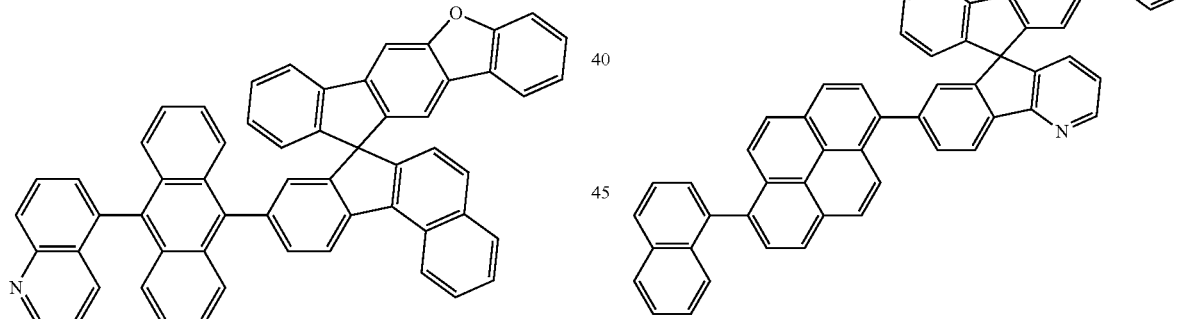
52
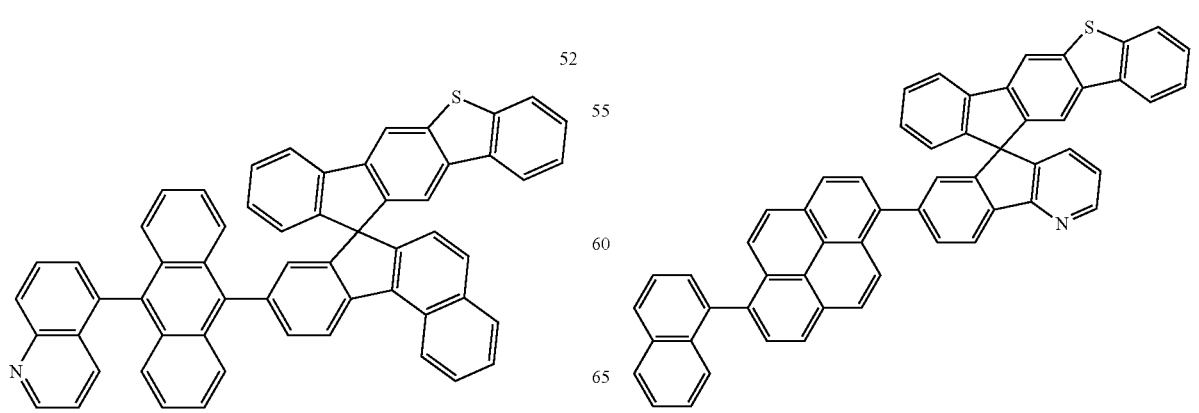
-continued
53
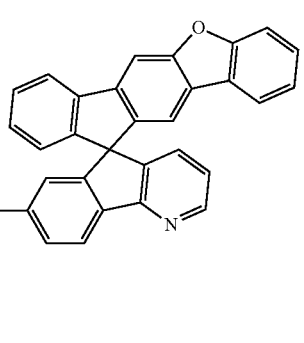
54
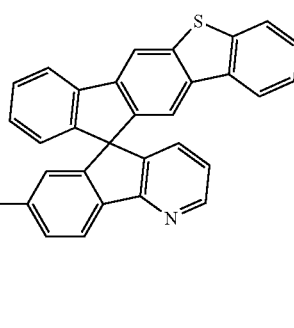
55
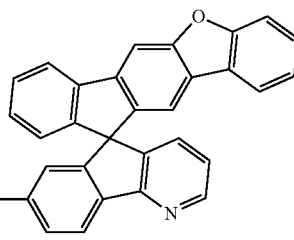
56
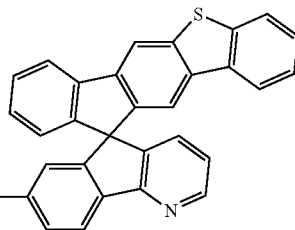

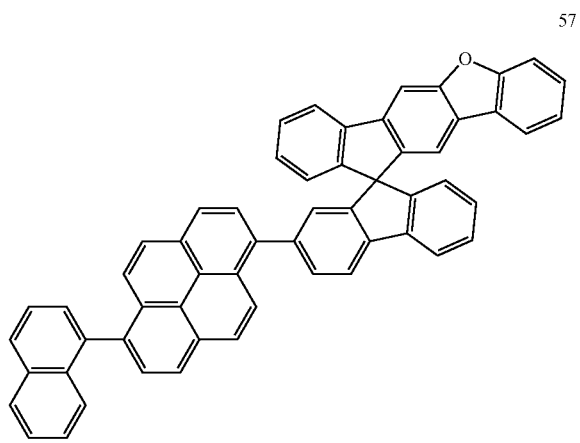

57

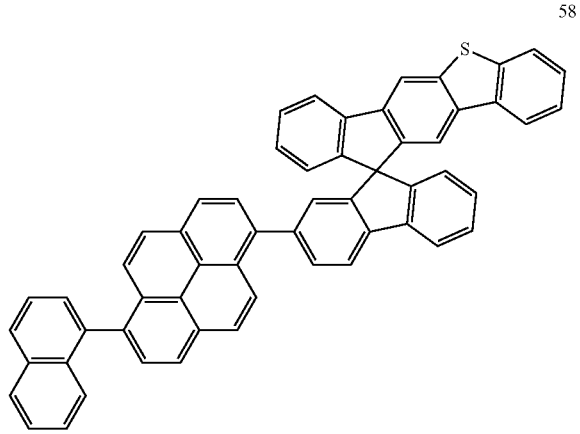

58

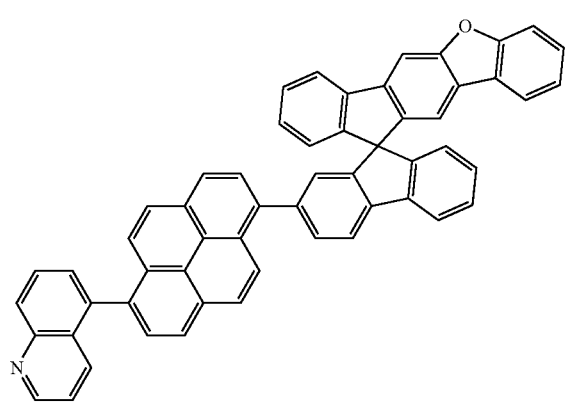

59

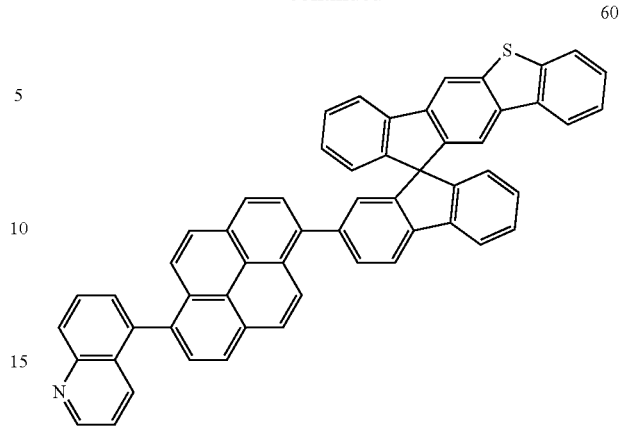

60

The condensed cyclic compound represented by Formula 1 may include a core of a spiro-bifluorene-based condensed ring, and thus deterioration caused by electrons may be prevented or reduced. Accordingly, an electronic device, for example, an organic light-emitting device, including the condensed cyclic compound represented by Formula 1, may have long lifespan. The condensed cyclic compound represented by Formula 1 may have a relatively high triplet (Ti) energy level, annihilation of triplet excitons may more likely occur in an EML including the condensed cyclic compound represented by Formula 1 so that the triplet-triplet annihilation (TTA) effect may be increased. Therefore, an electronic device, for example, an organic light-emitting device, including the condensed cyclic compound represented by Formula 1, may have high efficiency.

In the condensed cyclic compound represented by Formula 1, $L_1$ and $L_2$ may be each independently selected from a substituted or unsubstituted condensed polycyclic group including "at least three carbocyclic groups" condensed together, but not including a heteroatom as a ring-member atom; a1 and a2, which indicate the numbers of $L_1$s and $L_2$s, respectively, may be both not 0 (e.g., a1 and a2 are not both equal to 0, or are both greater than 0). In some embodiments, the group represented by $*-[(L_1)_{a1}-(R_1)_{b1}]$ in Formula 1 has at least one of "$L_1$" and the group represented by $*-[(L_2)_{a2}-(R_2)_{b2}]$ has at least one of "$L_2$". Furthermore, in Formula 1, c1+c2 may be equal to 1 or greater. In some embodiments, Formula 1 has at least one selected from the groups represented by $*-[(L_1)_{a1}-(R_1)_{b1}]$ and the groups represented by $*-[(L_2)_{a2}-(R_2)_{b2}]$. Therefore, when the condensed cyclic compound represented by Formula 1 is used, for example, as a host in an EML of an organic light emitting device, appropriate or suitable adjustment of host and dopant energy levels may be efficiently or suitably achieved to enable efficient host-dopant energy transfer. Accordingly, an electronic device, for example, an organic light-emitting device, including the condensed cyclic compound represented by Formula 1 may have high efficiency.

The condensed cyclic compound represented by Formula 1 may be synthesized using any suitable organic synthesis method available in the art. Synthesis methods of the condensed cyclic compound represented by Formula 1 may be understood by one of ordinary skill in the art based on the examples that are described below.

At least one of the condensed cyclic compound represented by Formula 1 may be used between a pair of electrodes of an organic light-emitting device. For example, the condensed cyclic compound represented by Formula 1 may be included in an emission layer of an organic light-emitting device. In some embodiments, the condensed cyclic compound represented by Formula 1 may be used as a material for capping layers disposed outwards of a pair of electrodes of an organic light-emitting device.

According to another embodiment of the present disclosure, an organic light-emitting device includes: a first electrode; a second electrode disposed opposite to the first electrode (e.g., a second electrode facing the first electrode); and an organic layer disposed between the first electrode and the second electrode and comprising an emission layer (EML), wherein the organic layer includes at least one of the condensed cyclic compound represented by Formula 1.

As used herein, the expression that "(for example, an organic layer may include) at least one of the condensed cyclic compound represented by Formula 1" means that "(the referenced organic layer may include) one of the condensed cyclic compound represented by Formula 1 or at least two different types or kinds of the condensed cyclic compound represented by Formula 1."

For example, the organic layer may include only Compound 1 as the at least one of the condensed cyclic compound represented by Formula 1. In some embodiments, Compound 1 may be in the EML of the organic light-emitting device. In some embodiments, the organic layer may include Compounds 1 and 2 as the at least one of the condensed cyclic compound represented by Formula 1. For example, Compounds 1 and 2 may be in the same layer (for example, both in the EML) or in different layers (for example, Compound 1 may be in the hole transport layer, and Compound 2 may be in the EML).

In some embodiments, the organic layer may include i) a hole transport region disposed between the first electrode (anode) and the emission layer and including at least one selected from a hole injection layer, a hole transport layer, a buffer layer, and an electron blocking layer, and ii) an electron transport region disposed between the emission layer and the second electrode (cathode) and including at least one selected from a hole blocking layer, an electron transport layer, and an electron injection layer. At least one selected from the hole transport region and the EML may include the at least one of the condensed cyclic compound represented by Formula 1. For example, the EML of the organic light-emitting device may include the at least one of the condensed cyclic compound represented by Formula 1. In some embodiments, the emission layer of the organic light-emitting device may include the at least one of the condensed cyclic compound represented by Formula 1. The at least one of the condensed cyclic compound represented by Formula 1 in the EML may serve as a host, wherein the EML may further include a dopant. In some embodiments, the dopant may be a phosphorescent dopant and/or a fluorescent dopant. For example, the dopant may be a fluorescent dopant.

In some embodiments, the organic light-emitting device may further include at least one selected from a first capping layer and a second capping layer, the first capping layer disposed on an optical path along which light generated in the EML passes outwards through the first electrode, and the second capping layer disposed on an optical path along which light generated in the EML passes outwards through the second electrode, wherein at least one selected from the first and second capping layers may include the at least one of the condensed cyclic compound represented by Formula 1.

For example, the organic light-emitting device may have i) a stack structure in which the first electrode, the organic layer, the second electrode, and the second capping layer are sequentially stacked upon one another in the stated order, ii) a stack structure in which the first capping layer, the first electrode, the organic layer, and the second electrode are sequentially stacked upon one another in the stated order, or iii) a stack structure in which the first capping layer, the first electrode, the organic layer, the second electrode, and the second capping layer are sequentially stacked upon one another in the stated order, wherein at least one selected from the first and second capping layers may include the at least one of the condensed cyclic compound represented by Formula 1.

As used herein, the term "organic layer" refers to a single layer and/or a plurality of layers disposed between the first and second electrodes of the organic light-emitting device. A material in the "organic layer" is not limited to an organic material. For example, in some embodiments, the organic layer may include an inorganic material.

Figure 1:
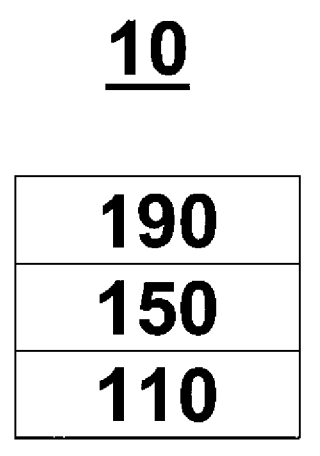

Hereinafter, a structure of an organic light-emitting device according to an embodiment of the present disclosure and a method of manufacturing the same will now be described with reference to FIG. 1.

FIG. 1 is a schematic cross-sectional view of an organic light-emitting device 10 according to an embodiment of the present disclosure. Referring to FIG. 1, the organic light-emitting device 10 includes a first electrode 110, an organic layer 150, and a second electrode 190.

A substrate may be disposed under the first electrode 110 or on the second electrode 190 in FIG. 1. The substrate may be a glass or transparent plastic substrate having good mechanical strength, thermal stability, transparency, surface smoothness, ease of handling, and water resistance.

For example, the first electrode 110 may be formed by depositing or sputtering a first electrode-forming material on the substrate. When the first electrode 110 is an anode, a material having a high work function may be used as the first electrode-forming material to facilitate hole injection. The first electrode 110 may be a reflective electrode, a semi-transmissive electrode, or a transmissive electrode.

Transparent and conductive materials such as ITO, IZO, $SnO_2$, and ZnO may be used to form the first electrode. The first electrode 110 as a semi-transmissive electrode or a reflective electrode may be formed of at least one material selected from magnesium (Mg), aluminum (Al), aluminum-lithium (Al—Li), calcium (Ca), magnesium-indium (Mg—In), and magnesium-silver (Mg—Ag).

The first electrode 110 may have a single-layer structure or a multi-layer structure including a plurality of layers. For example, the first electrode 110 may have a three-layered structure of ITO/Ag/ITO, but the first electrode is not limited thereto.

The organic layer 150 may be disposed on the first electrode 110. The organic layer 150 may include an emission layer (EML).

The organic layer 150 may include a hole transport region disposed between the first electrode and the EML, and an electron transport region between the EML and the second electrode.

For example, the hole transport region may include at least one selected from a hole injection layer (HIL), a hole transport layer (HTL), a buffer layer, and an electron blocking layer (EBL). For example, the electron transport layer may include at least one selected from a hole blocking layer (HBL), an electron transport layer (ETL), and an electron injection layer (EIL). However, embodiments of the present disclosure are not limited thereto.

The hole transport region may have a single-layered structure including a single material, a single-layered structure including a plurality of materials, or a multi-layered structure including a plurality of layers including different materials.

In some embodiments, the electron transport region may have a single-layered structure including a plurality of materials, or a multi-layered structure of HIL/HTL, HIL/HTL/buffer layer, HIL/buffer layer, HTL/buffer layer, or HIL/HTL/EBL, wherein these layers forming a multi-layered structure are sequentially disposed on the first electrode 110 in the order stated above. However, embodiments of the present disclosure are not limited thereto.

When the hole transport region includes a HIL, the HIL may be formed on the first electrode 110 by using any of a variety of suitable methods, for example, by using vacuum deposition, spin coating, casting, Langmuir-Blodgett (LB) deposition, inkjet printing, laser printing, laser induced thermal imaging (LITI), or the like.

When the HIL is formed using vacuum deposition, the deposition conditions may vary depending on the material that is used to form the HIL and the structure of the HIL. For example, the deposition conditions may be selected from the following conditions: a deposition temperature of about 100° C. to about 500° C., a degree of vacuum of about $10^{-8}$ to about $10^{-3}$ torr, and a deposition rate of about 0.01 to 100 Å/sec.

When the HIL is formed using spin coating, the coating conditions may vary depending on the material that is used to form the HIL and the structure of the HIL. For example, the coating conditions may be selected from the following conditions: a coating rate of about 2,000 rpm to about 5,000 rpm and a heat treatment temperature of about 800° C. to about 200° C.

When the hole transport region includes an HTL, the HTL may be formed on the first electrode 110 or the HIL by using any of a variety of suitable methods, for example, by using vacuum deposition, spin coating, casting, Langmuir-Blodgett (LB) deposition, inkjet printing, laser printing, laser induced thermal imaging (LITI), or the like. When the HTL is formed using vacuum deposition or spin coating, the conditions for deposition and coating may be similar to the above-described deposition and coating conditions for forming the HIL, and accordingly further description thereof is not necessary.

For example, the hole transport region may include the at least one of the condensed cyclic compound represented by Formula 1. For example, the hole transport region may include an HTL, and the HTL may include the at least one of the condensed cyclic compound represented by Formula 1.

In some embodiments, the hole transport region may include at least one selected from m-MTDATA, TDATA, 2-TNATA, NPB, β-NPB, TPD, Spiro-TPD, Spiro-NPB, methylated-NPB, TAPC, HMTPD, 4,4',4''-tris(N-carbazolyl)triphenylamine (TCTA), polyaniline/dodecylbenzene sulfonic acid (Pani/DBSA), poly(3,4-ethylenedioxythiophene)/poly(4-styrenesulfonate)(PEDOT/PSS), polyaniline/camphor sulfonic acid (Pani/CSA), polyaniline/poly(4-styrenesulfonate) (PANI/PSS), a compound represented by Formula 201, and a compound represented by Formula 202.

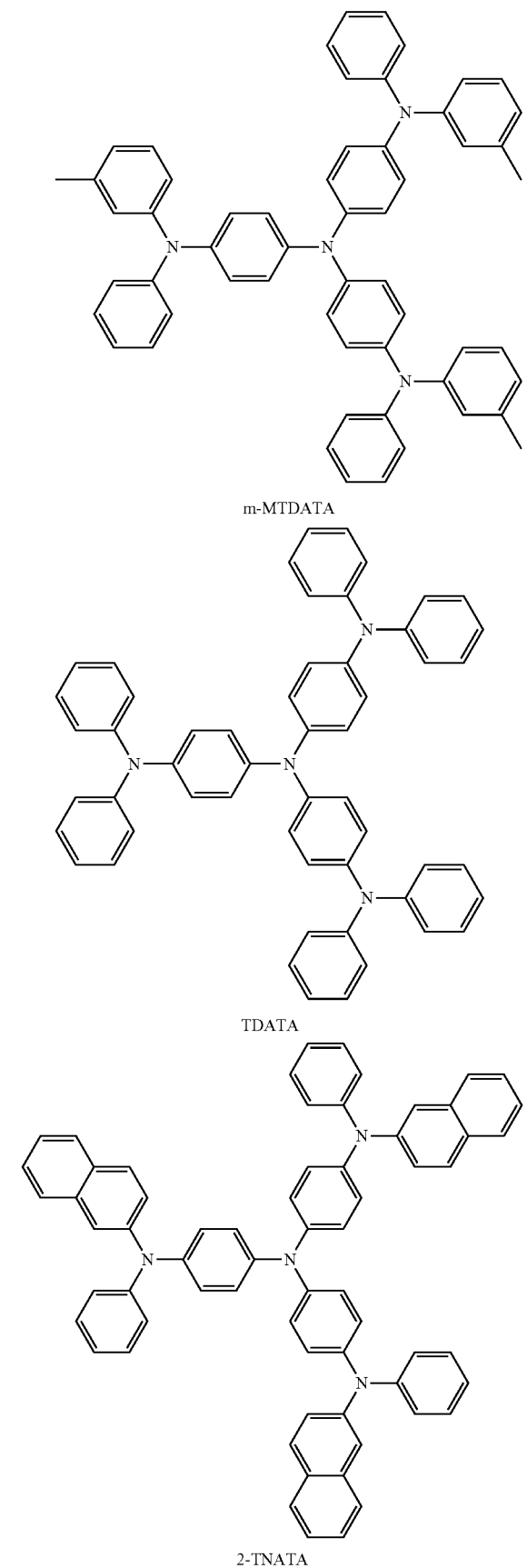

m-MTDATA

TDATA

2-TNATA

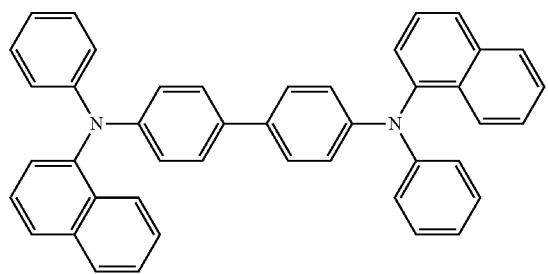

NPB

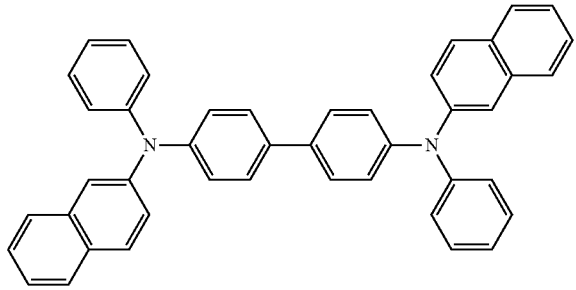

β-NPB

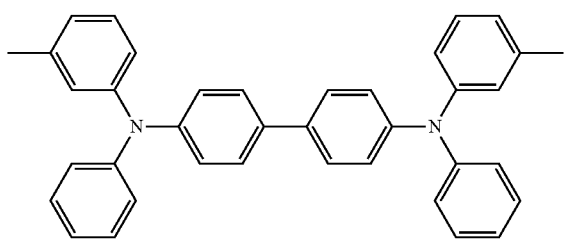

TPD

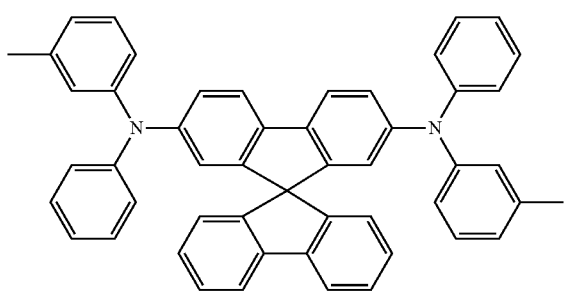

Spiro-TPD

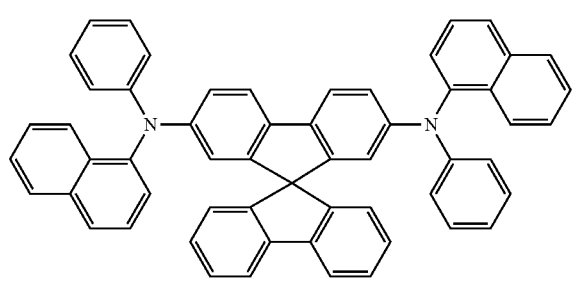

Spiro-NPB

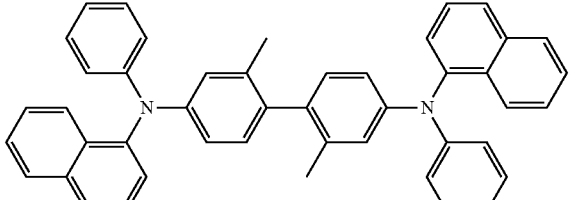

methylated NPB

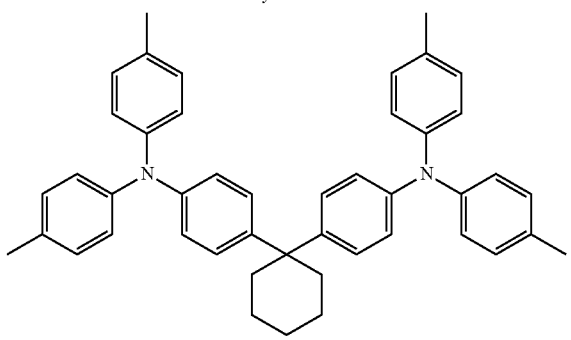

TAPC

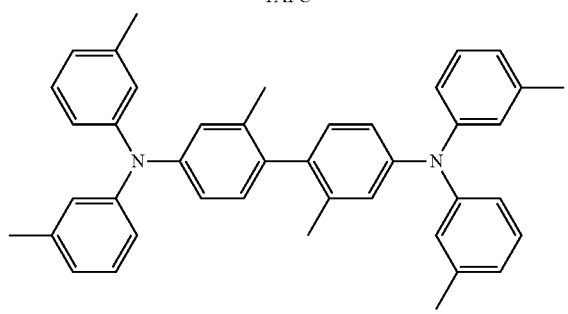

HMTPD

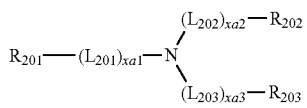

Formula 201

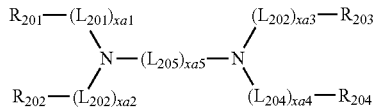

Formula 202

In Formulae 201 and 202, $L_{201}$ to $L_{205}$ may be each independently defined the same as $L_{11}$ described in connection with Formula 1;

xa1 to xa4 are each independently selected from 0, 1, 2, and 3;

xa5 may be selected from 1, 2, 3, 4, and 5;

$R_{201}$ to $R_{204}$ may be each independently selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

For example, in Formulae 201 and 202,

L$_{201}$ to L$_{205}$ may be each independently selected from:

a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene, and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, an isoindolyl group, a quinolinyl group, an isoquinolinyl group, a quinoxalinyl group, a quinazolinyl group, a carbazolyl group, and a triazinyl group;

xa1 to xa4 may be each independently 0, 1, or 2;

xa5 may be 1, 2, or 3;

R$_{201}$ to R$_{204}$ may be each independently selected from:

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an azulenyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group. However, embodiments of the present disclosure are not limited thereto.

The compound represented by Formula 201 may be represented by Formula 201A, but the compound is not limited thereto.

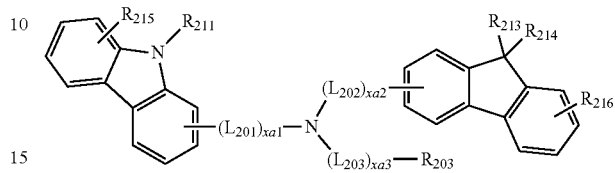

Formula 201A

For example, the compound represented by Formula 201 may be represented by Formula 201A-1, but the compound is not limited thereto.

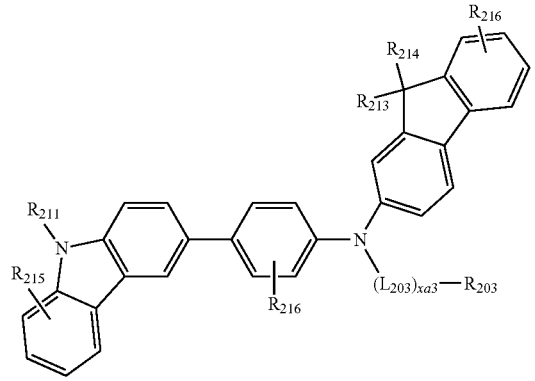

Formula 201A-1

The compound represented by Formula 202 may be represented by Formula 202A, but the compound is not limited thereto.

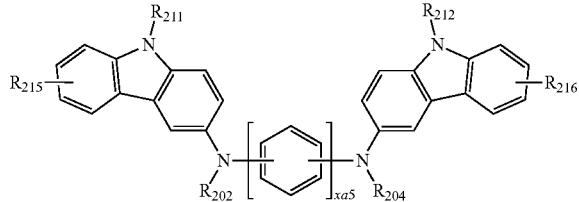

Formula 202A

In Formulae 201A, 201A-1, and 202A,

L$_{201}$ to L$_{203}$, xa1 to xa3, xa5, and R$_{202}$ to R$_{204}$ may be defined as described in connection with Formulae 201 and 203;

R$_{211}$ and R$_{212}$ may be defined the same as described in connection with R$_{203}$ in Formula 201; and R$_{213}$ to R$_{216}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic hetero-condensed polycyclic group.

The compound represented by Formula 201, and the compound represented by Formula 202 may include compounds HT1 to HT20, but the compounds are not limited thereto.

HT1

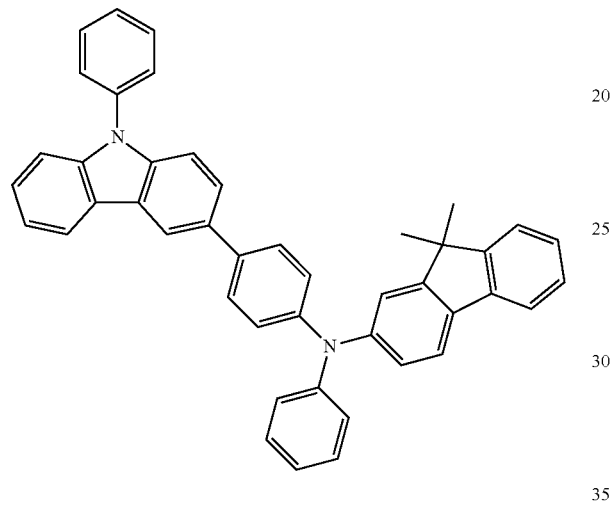

HT2

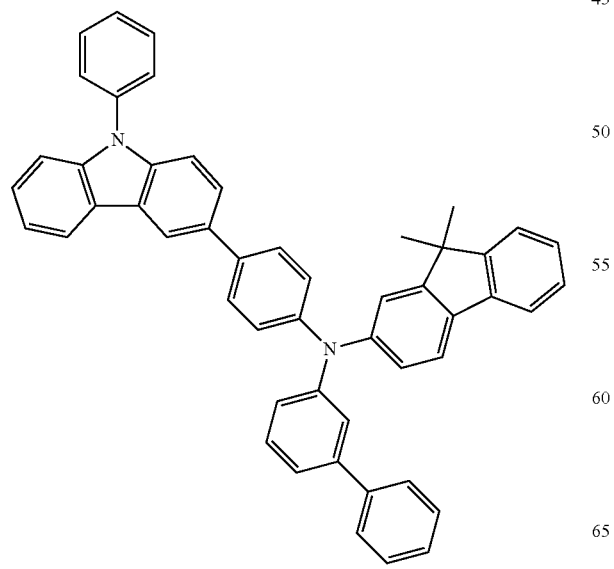

HT3

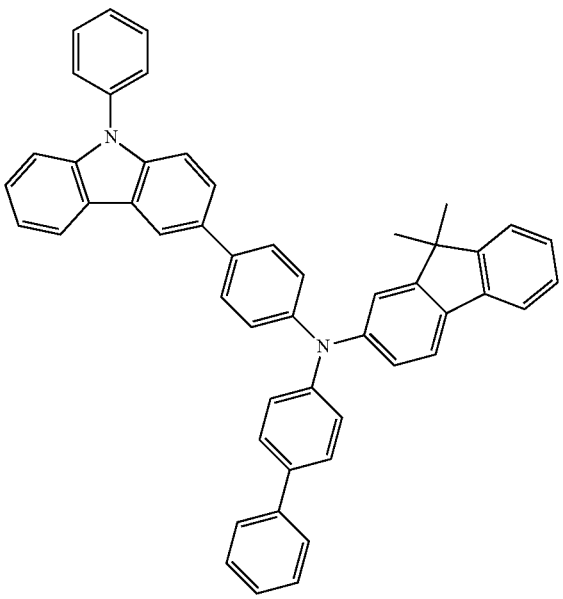

HT4

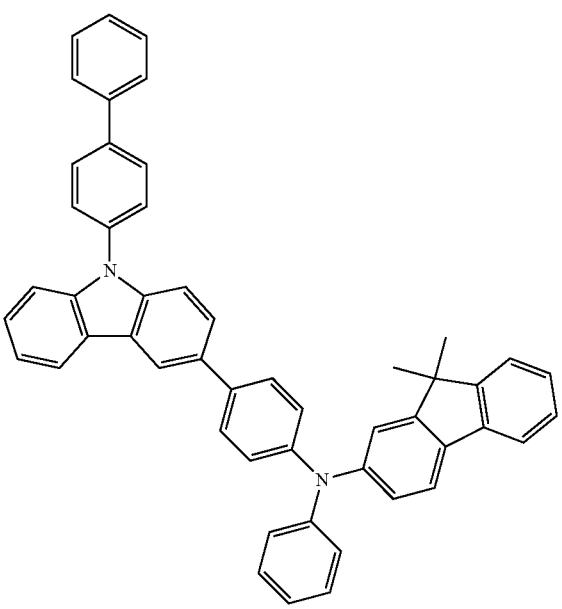

HT5
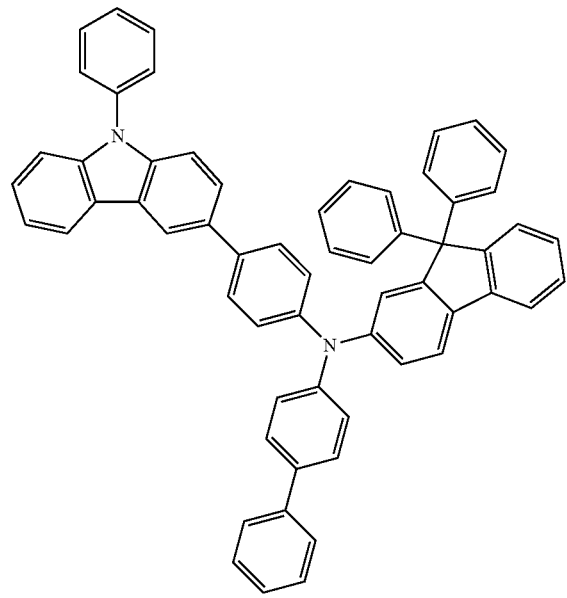
HT7
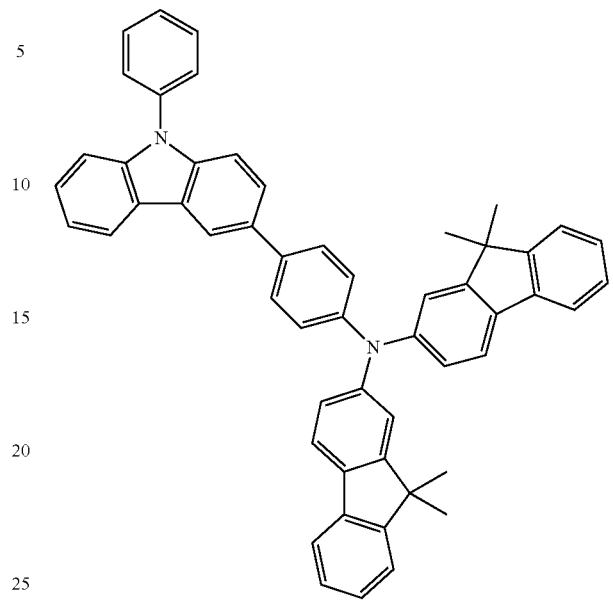
HT6
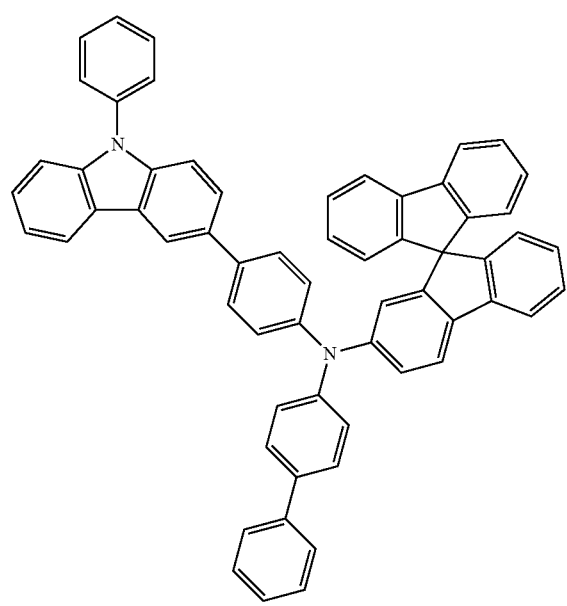
HT8
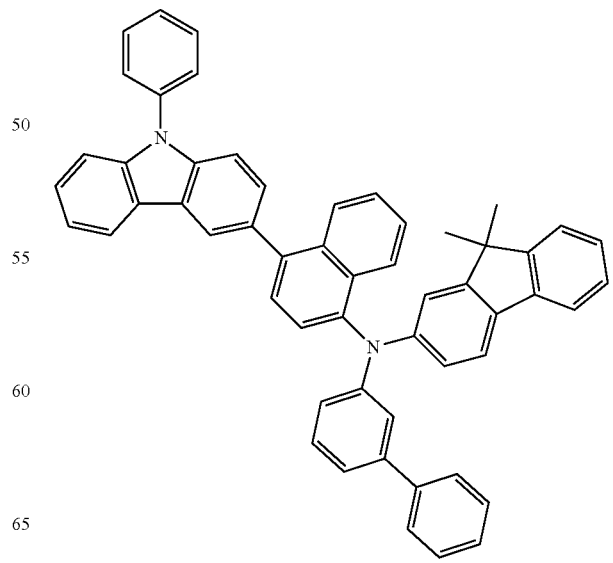

HT9
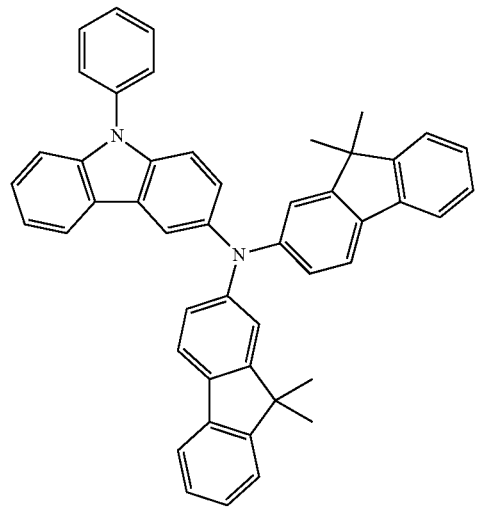
HT11
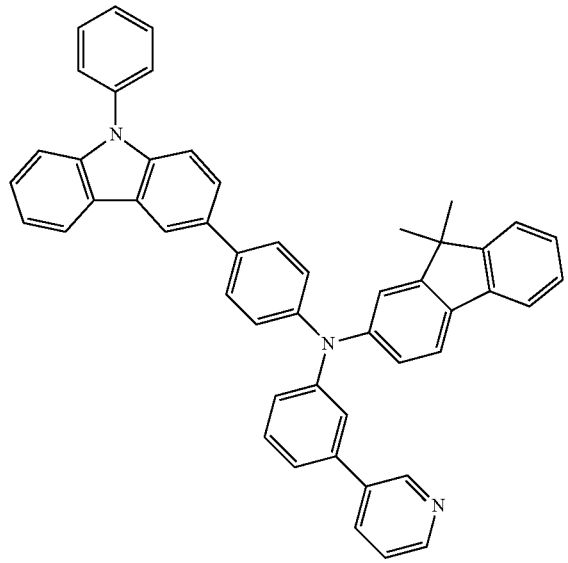
HT12
HT10
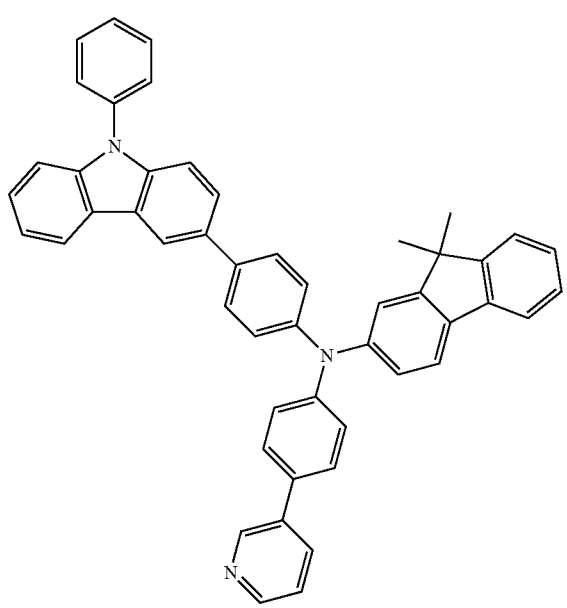
HT13
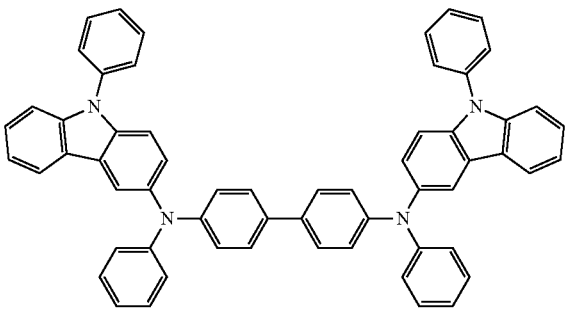

-continued

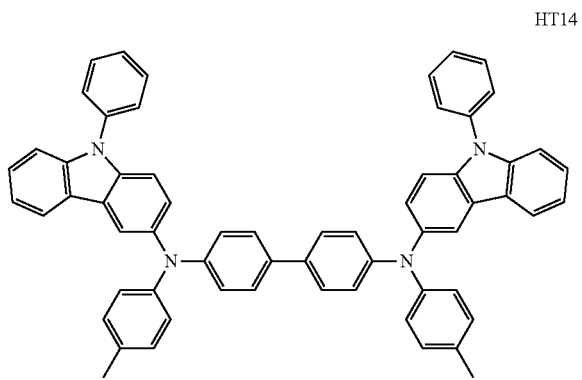
HT14

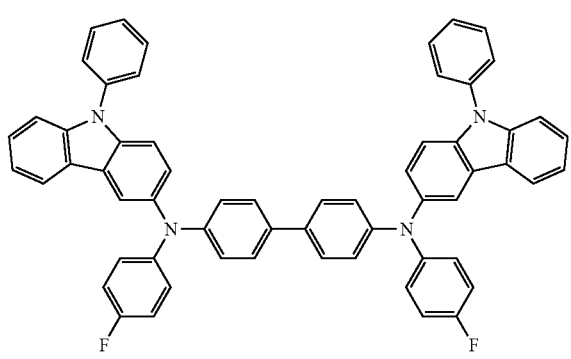
HT15

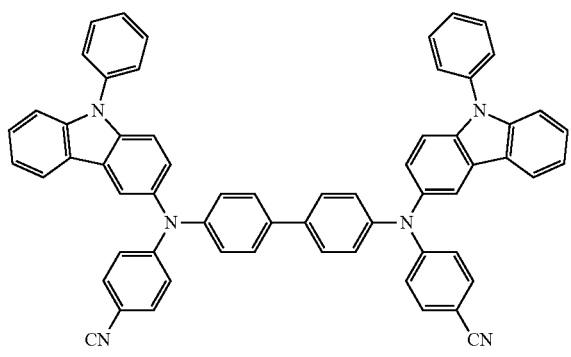
HT16

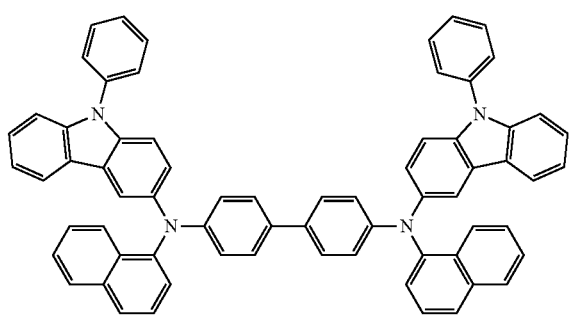
HT17

-continued

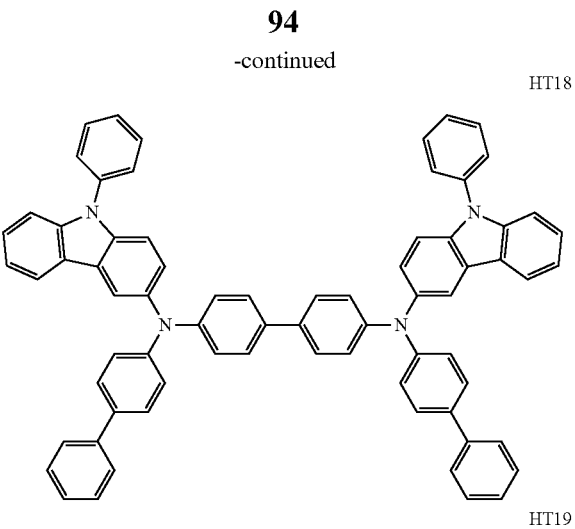
HT18

HT19

HT20

The thickness of the hole transport region may be from about 100 Å to about 10000 Å, and in some embodiments, from about 100 Å to about 1000 Å. When the hole transport region includes a HIL and a HTL, the thickness of the HIL may be from about 100 Å to about 10,000 Å, and in some embodiments, from about 100 Å to about 1,000 Å, and a thickness of the HTL may be from about 50 Å to about 2,000 Å, and in some embodiments, from about 100 Å to about 1,500 Å. When the thicknesses of the hole transport region, the HIL, and the HTL are within these ranges, suitable or satisfactory hole transport characteristics may be obtained without a substantial increase in driving voltage.

The hole transport region may further include a charge-generating material to improve conductivity, in addition to the materials as described above. The charge-generating material may be homogeneously or inhomogeneously dispersed in the hole transport region.

The charge-generating material may be, for example, a p-dopant. The p-dopant may be one selected from quinine derivatives, metal oxides, and compounds having a cyano group, but the p-dopant is not limited thereto. Non-limiting examples of the p-dopant include quinone derivatives such as tetracyanoquinonedimethane (TCNQ), 2,3,5,6-tetrafluoro-tetracyano-1,4-benzoquinonedimethane (F4-TCNQ), and the like; metal oxides such as tungsten oxide, molybdenum oxide, and the like; and Compound HT-D1 below.

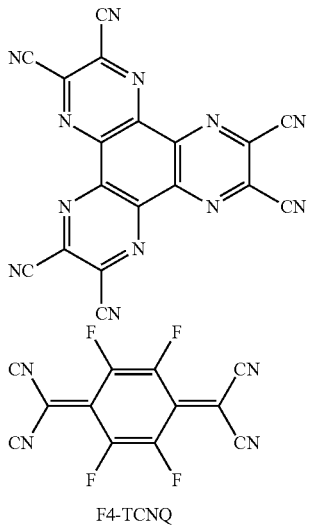

Compound HT-D1

F4-TCNQ

The hole transport region may further include at least one selected from a buffer layer and an EBL, in addition to the HIL and HTL described above. The buffer layer may compensate for an optical resonance distance of light according to a wavelength of the light emitted from the EML, and thus may improve light-emission efficiency. A material in the buffer layer may be any suitable material used in the hole transport region. The EBL may block migration of electrons from the electron transport region into the EML.

The EML may be formed on the first electrode 110 or the hole transport region by using any of a variety of suitable methods, for example, by using vacuum deposition, spin coating, casting, Langmuir-Blodgett (LB) deposition, inkjet printing, laser printing, laser induced thermal imaging (LITI), or the like. When the EML is formed using vacuum deposition or spin coating, the deposition and coating conditions for forming the EML may be similar to the above-described deposition and coating conditions for forming the HIL, and accordingly will not be repeated again here.

When the organic light-emitting device 10 is a full color organic light-emitting device, the EML may be patterned into a red emission layer, a green emission layer, and a blue emission layer to correspond to individual subpixels, respectively. In some embodiments, the EML may have a structure in which a red emission layer, a green emission layer and a blue emission layer are stacked upon one another, or a structure including a mixture of a red light-emitting material, a green light-emitting material, and a blue light-emitting material, and thus may emit white light.

The EML may include a host and a dopant. The host may include at least one of the condensed cyclic compound represented by Formula 1.

The dopant may include a phosphorescent dopant and/or a fluorescent dopant.

The phosphorescent dopant may include an organometallic complex represented by Formula 401.

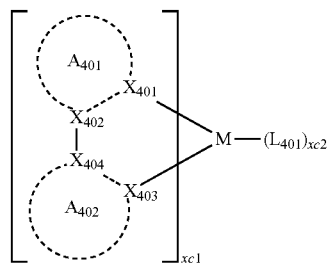

Formula 401

In Formula 401,

M may include iridium (Ir), platinum (Pt), osmium (Os), titanium (Ti), zirconium (Zr), hafnium (Hf), europium (Eu), terbium (Tb), or thulium (Tm);

$X_{401}$ to $X_{404}$ may be each independently a nitrogen or a carbon;

rings $A_{401}$ and $A_{402}$ may be each independently selected from a substituted or unsubstituted benzene, a substituted or unsubstituted naphthalene, a substituted or unsubstituted fluorene, a substituted or unsubstituted spiro-fluorene, a substituted or unsubstituted indene, a substituted or unsubstituted pyrrole, a substituted or unsubstituted thiophene, a substituted or unsubstituted furan, a substituted or unsubstituted imidazole, a substituted or unsubstituted pyrazole, a substituted or unsubstituted thiazole, a substituted or unsubstituted isothiazole, a substituted or unsubstituted oxazole, a substituted or unsubstituted isoxazole, a substituted or unsubstituted pyridine, a substituted or unsubstituted pyrazine, a substituted or unsubstituted pyrimidine, a substituted or unsubstituted pyridazine, a substituted or unsubstituted quinoline, a substituted or unsubstituted isoquinoline, a substituted or unsubstituted benzoquinoline, a substituted or unsubstituted quinoxaline, a substituted or unsubstituted quinazoline, a substituted or unsubstituted carbazole, a substituted or unsubstituted benzoimidazole, a substituted or unsubstituted benzofuran, a substituted or unsubstituted benzothiophene, a substituted or unsubstituted isobenzothiophene, a substituted or unsubstituted benzoxazole, a substituted or unsubstituted isobenzoxazole, a substituted or unsubstituted triazole, a substituted or unsubstituted oxadiazole, a substituted or unsubstituted triazine, a substituted or unsubstituted dibenzofuran, and a substituted or unsubstituted dibenzothiophene;

at least one substituent of the substituted benzene, the substituted naphthalene, the substituted fluorene, the substituted spiro-fluorene, the substituted indene, the substituted pyrrole, the substituted thiophene, the substituted furan, the substituted imidazole, the substituted pyrazole, the substituted thiazole, the substituted isothiazole, the substituted oxazole, the substituted isoxazole, the substituted pyridine, the substituted pyrazine, the substituted pyrimidine, the substituted pyridazine, the substituted quinoline, the substituted isoquinoline, the substituted benzoquinoline, the substituted quinoxaline, the substituted quinazoline, the substituted carbazole, the substituted benzoimidazole, the substituted benzofuran, the substituted benzothiophene, the substituted isobenzothiophene, the substituted benzoxazole, the substituted isobenzoxazole, the substituted triazole, the substituted oxadiazole, the substituted triazine, the substituted dibenzofuran, and the substituted dibenzothiophene may be selected from:

a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxyl group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{401}$)($Q_{402}$), —Si($Q_{403}$)($Q_{404}$)($Q_{405}$), and —B($Q_{406}$)($Q_{407}$), a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{411}$)($Q_{412}$), —Si($Q_{413}$)($Q_{414}$)($Q_{415}$), and —B($Q_{416}$)($Q_{417}$), and —N($Q_{421}$)($Q_{422}$), —Si($Q_{423}$)($Q_{424}$)($Q_{425}$), and —B($Q_{426}$)($Q_{427}$);

$L_{401}$ may be an organic ligand;

xc1 may be 1, 2, or 3; and xc2 may be 0, 1, 2, or 3, wherein $Q_{401}$ to $Q_{407}$, $Q_{411}$ to $Q_{417}$ and $Q_{421}$ to $Q_{427}$ may be each independently selected from a hydrogen, a $C_1$-$C_{60}$ alkyl group, a $C_2$-$C_{60}$ alkenyl group, a $C_6$-$C_{60}$ aryl group, and a $C_1$-$C_{60}$ heteroaryl group.

For example, in Formula 401, $L_{401}$ may be a monovalent, divalent, or trivalent organic ligand. For example, $L_{401}$ in Formula 401 may be selected from a halogen ligand (for example, Cl or F), a diketone ligand (for example, acetylacetonate, 1,3-diphenyl-1,3-propanedionate, 2,2,6,6-tetramethyl-3,5-heptanedionate, or hexafluoroacetonate), a carboxylic acid ligand (for example, picolinate, dimethyl-3-pyrazolecarboxylate, or benzoate), a carbon monoxide ligand, an isonitrile ligand, a cyano ligand, and a phosphorous ligand (for example, phosphine or phosphite). However, embodiments of the present disclosure are not limited thereto.

When $A_{401}$ in Formula 401 has at least two substituent groups, the at least two substituent groups of $A_{401}$ may be linked to each other to form a saturated or unsaturated ring.

When $A_{402}$ in Formula 401 has at least two substituents groups, the at least two substituent groups of $A_{402}$ may be linked to each other (e.g., combined together) to form a saturated or unsaturated ring.

When xc1 in Formula 401 is 2 or greater, a plurality of ligands

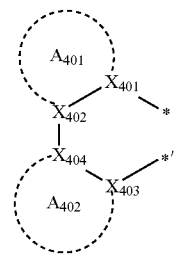

in Formula 401 may be identical to or different from each other. When xc1 in Formula 1 is 2 or greater, $A_{401}$ and $A_{402}$ may be linked to $A_{401}$ and $A_{402}$ of another adjacent ligand, respectively, directly or via a linking group (for example, a $C_1$-$C_5$ alkylene group, —N(R')— (where R' is a $C_1$-$C_{10}$ alkyl group or a $C_6$-$C_{20}$ aryl group), or C(=O)—).

The phosphorescent dopant may include at least one selected from Compounds PD1 to PD75, but the phosphorescent dopant is not limited thereto.

PD1

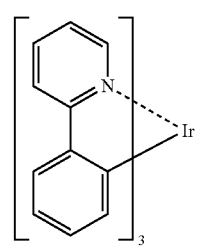

PD2

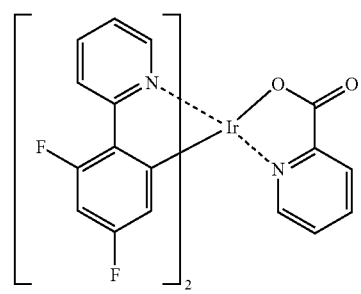

-continued
PD3
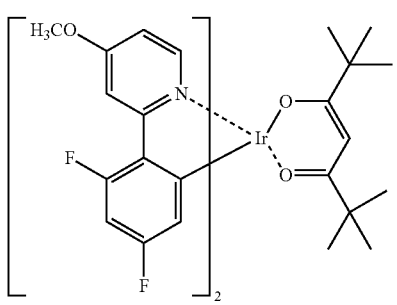
PD8
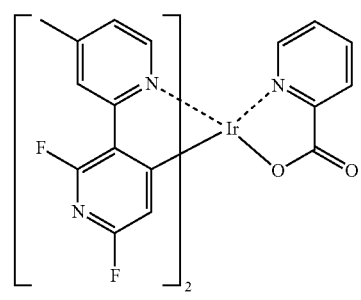
PD4
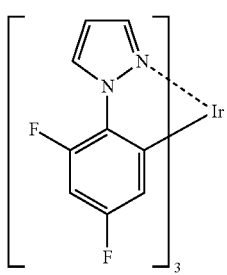
PD9
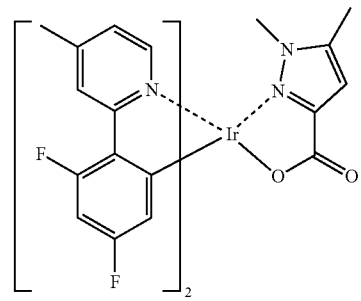
PD5
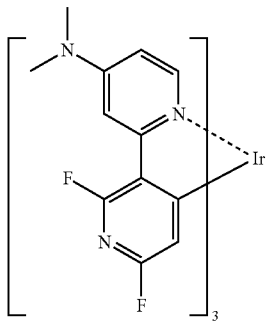
PD10
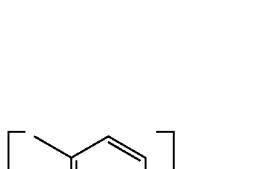
PD6
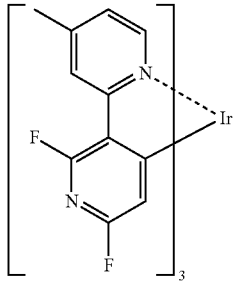
PD11
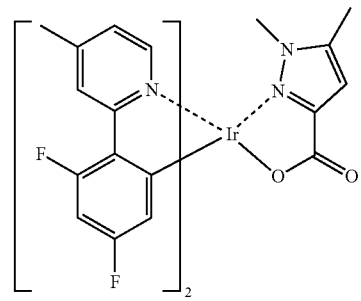
PD7
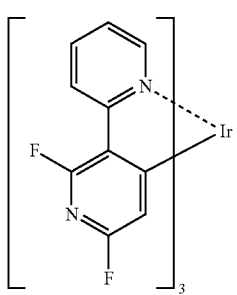
PD12
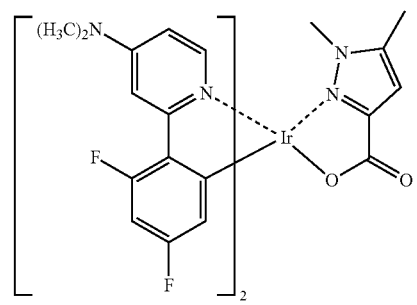

PD13 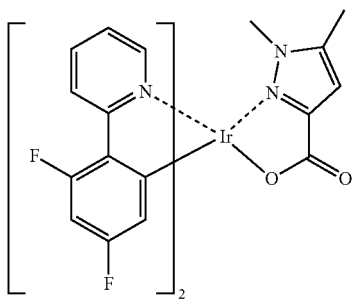
PD14 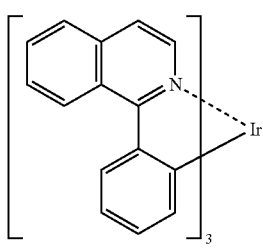
PD15 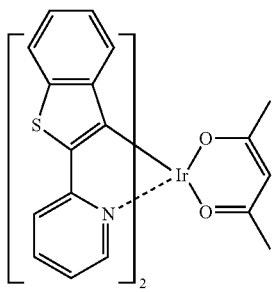
PD16 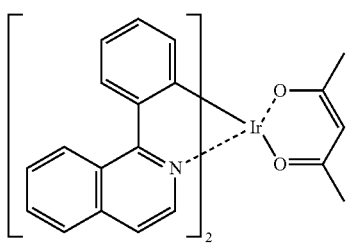
PD17 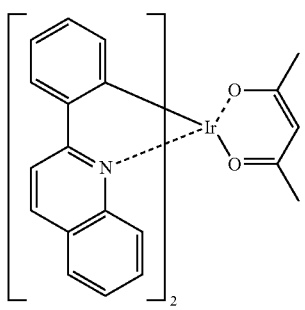
PD18 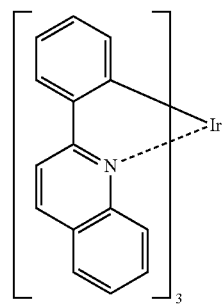
PD19 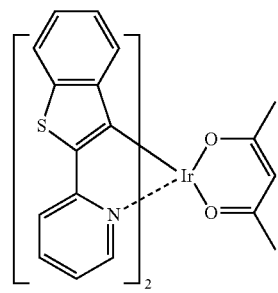
PD20 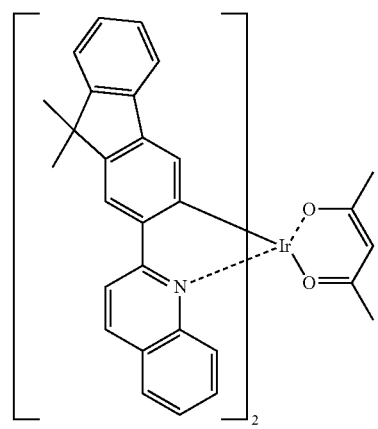
PD21 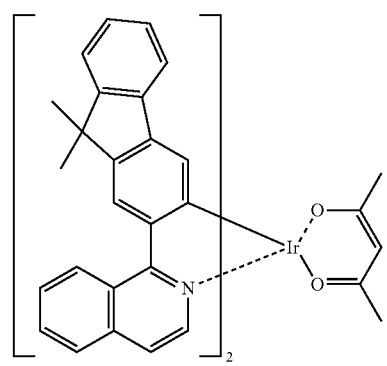
PD22 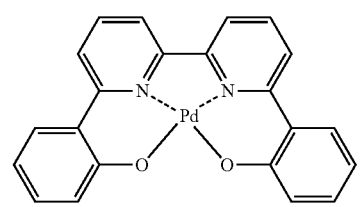

-continued
PD23
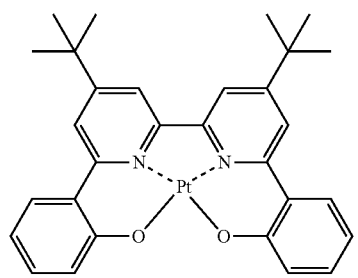
PD24
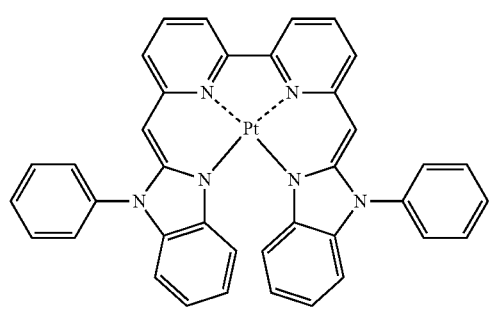
PD25
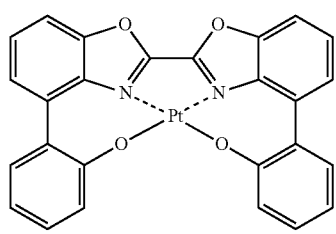
PD26
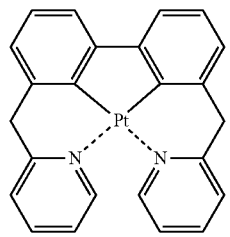
PD27
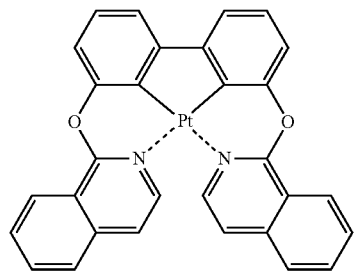
PD28
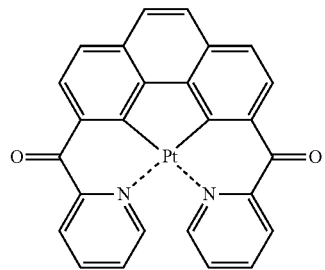
PD29
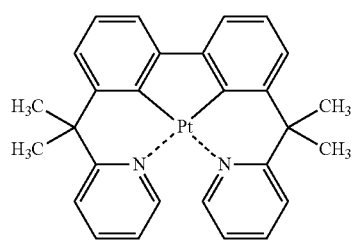
PD30
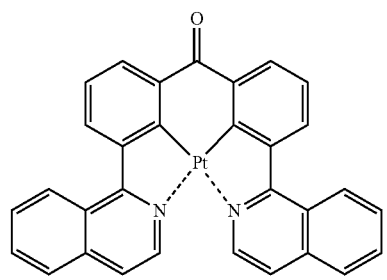
PD31
PD32
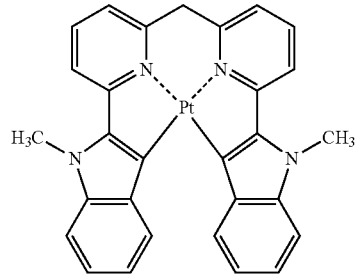
PD33
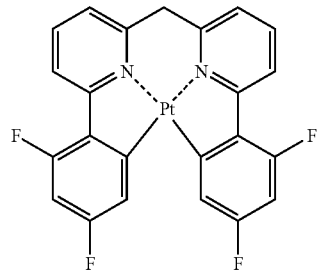

-continued
PD34
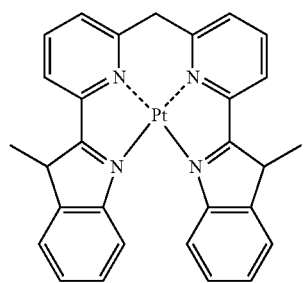
PD35
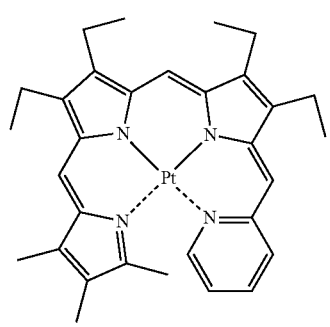
PD36
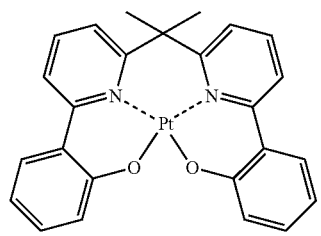
PD37
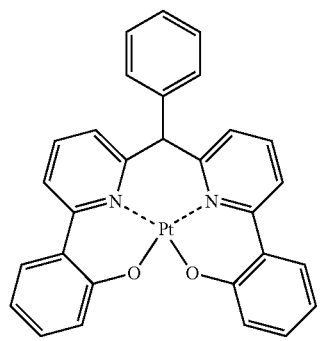
PD38
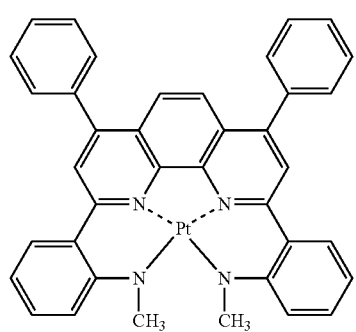
-continued
PD39
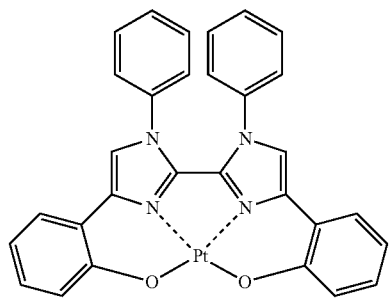
PD40
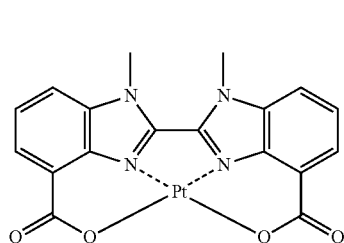
PD41
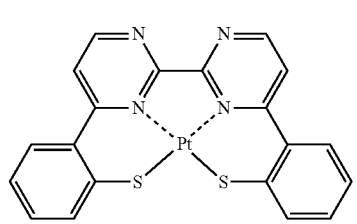
PD42
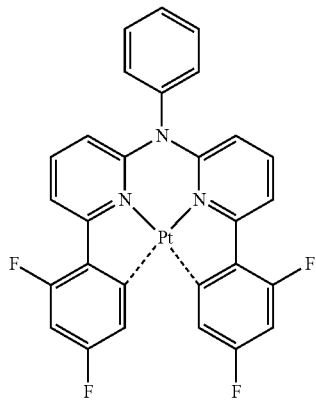
PD43
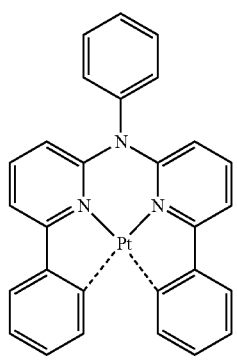

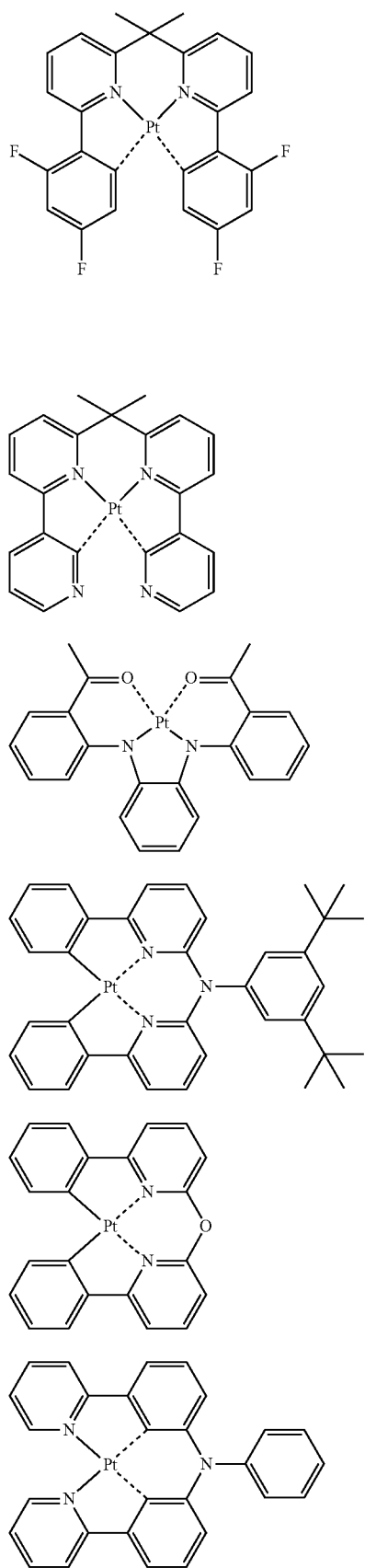
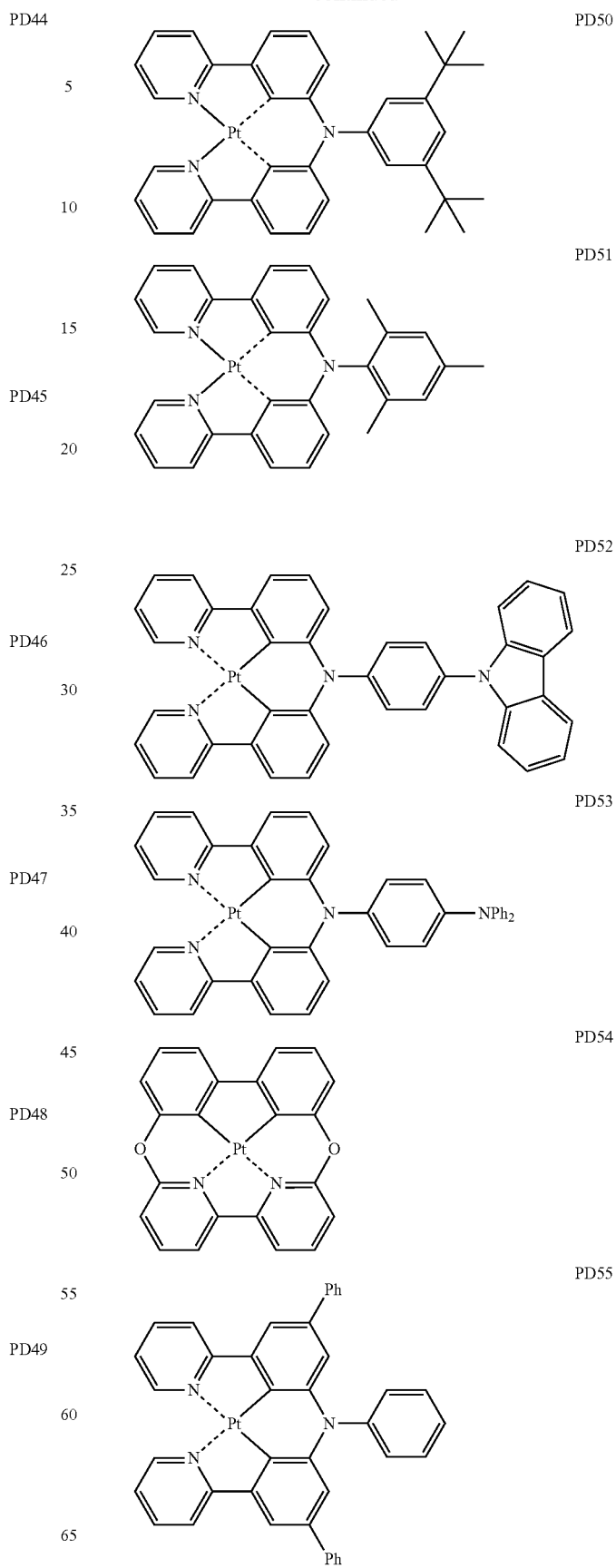

PD56 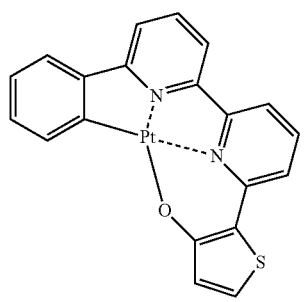
PD61 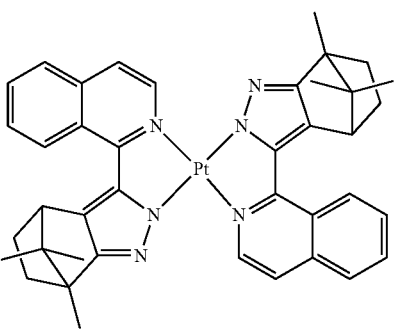
PD57 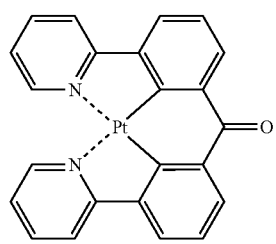
PD62 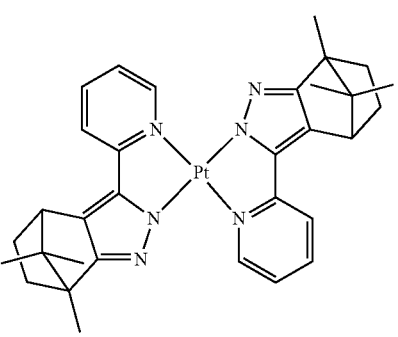
PD58 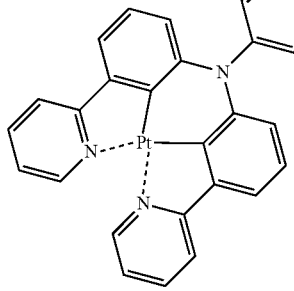
PD63 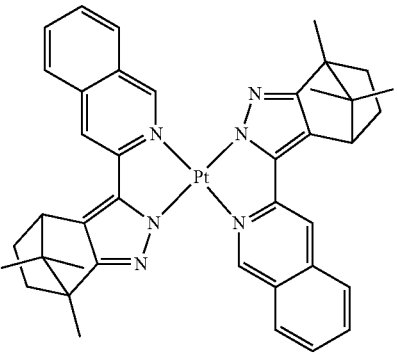
PD59 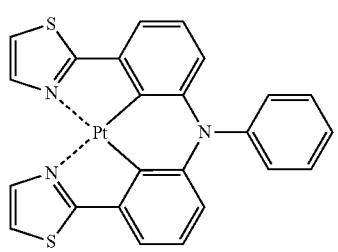
PD64 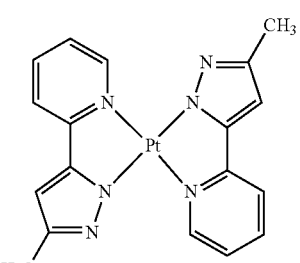
PD60 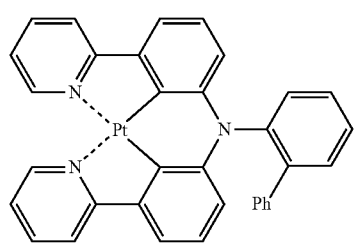
PD65 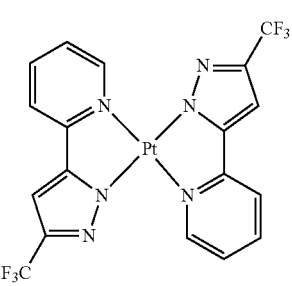

PD66 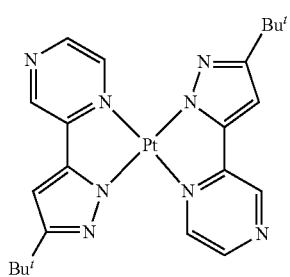
PD67 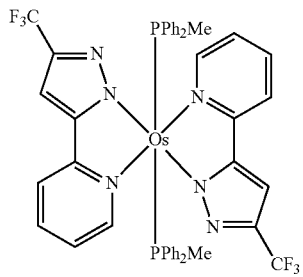
PD68
PD69
PD70 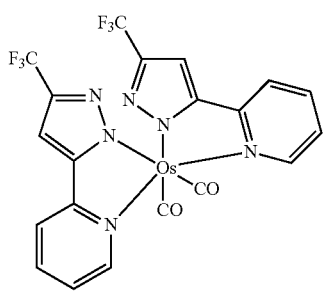
PD71 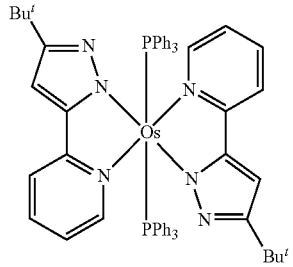
PD72
PD73 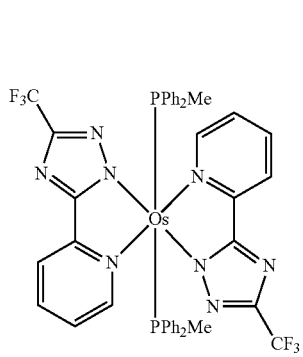
PD74 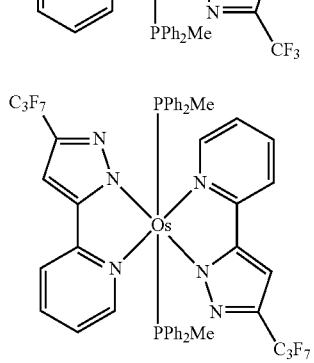
PD75 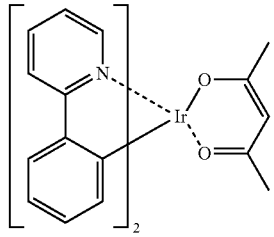
For example, the fluorescent dopant may include a compound represented by Formula 501.

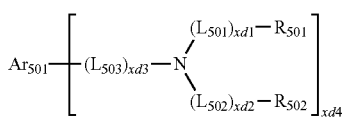

Formula 501

In Formula 501,

Ar$_{501}$ may be selected from:

a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene, a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{501}$)($Q_{502}$)($Q_{503}$), wherein $Q_{501}$ to $Q_{503}$ may be each independently selected from a hydrogen, $C_1$-$C_{60}$ alkyl group, a $C_2$-$C_{60}$ alkenyl group, a $C_6$-$C_{60}$ aryl group, and a $C_1$-$C_{60}$ heteroaryl group;

$L_{501}$ to $L_{503}$ may be defined the same as $L_{201}$ defined herein;

$R_{501}$ and $R_{502}$ may be each independently selected from:

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group, and a phenyl group, a naphthyl group, a fluorenyl group, spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group, each substituted with at least one selected from a phenyl group, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, and a dibenzofuranyl group, and a dibenzothiophenyl group;

xd1 to xd3 may be each independently selected from 0, 1, 2, and 3; and xd4 may be selected from 1, 2, 3, and 4.

For example, the fluorescent host may include at least one selected from Compounds FD1 to FD9.

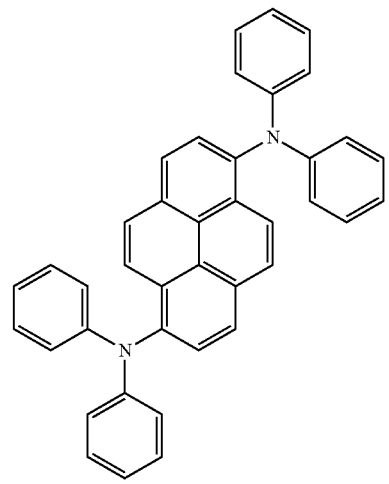

FD1

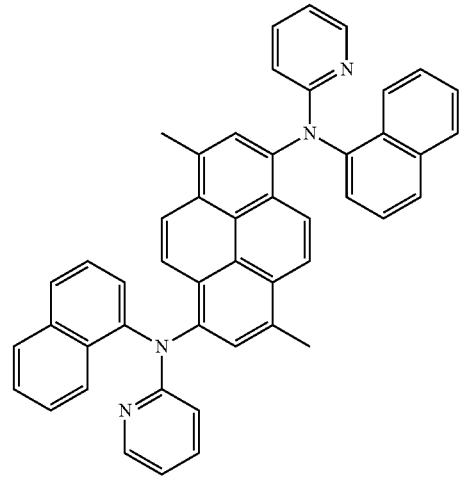

FD2

FD3 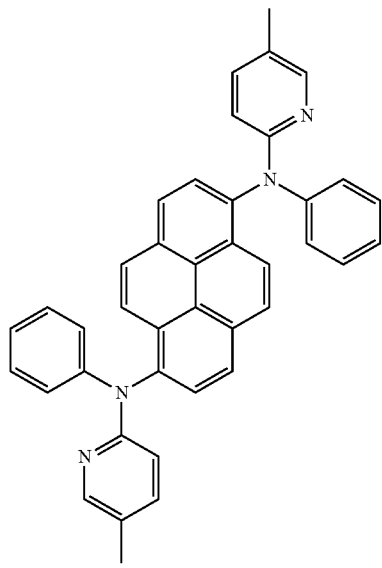
FD5 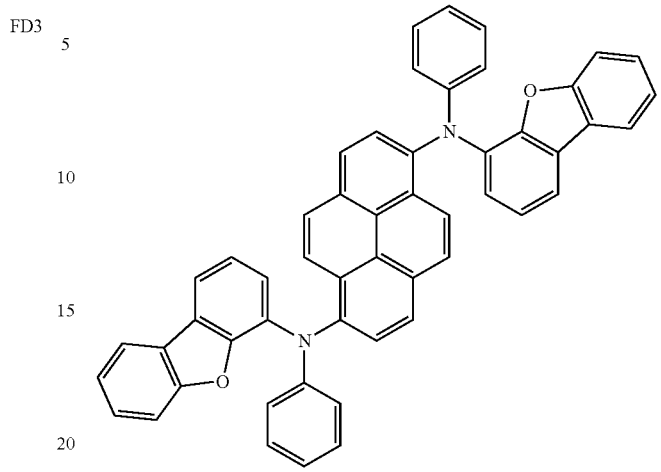
FD6 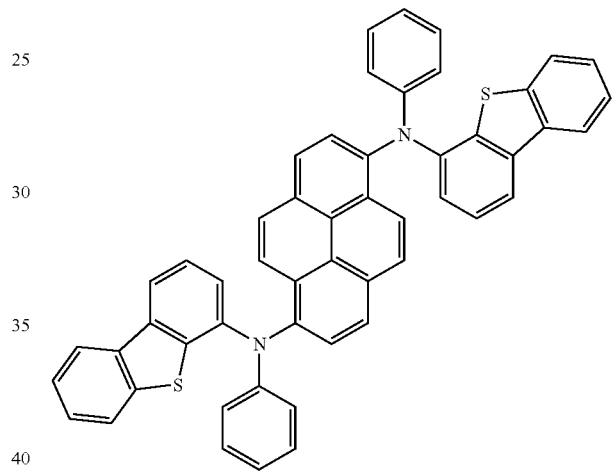
FD4 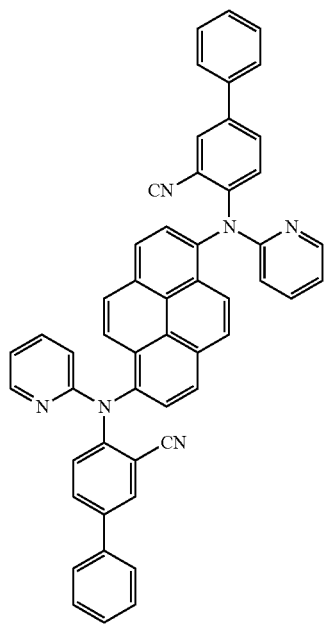
FD7 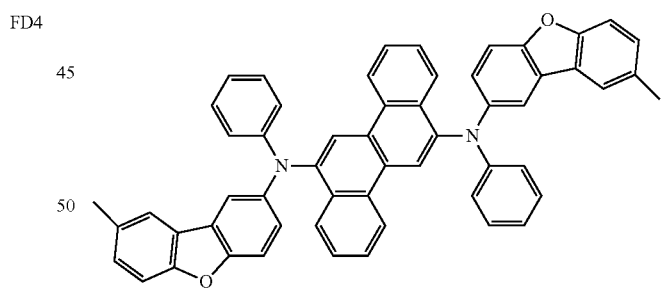
FD8 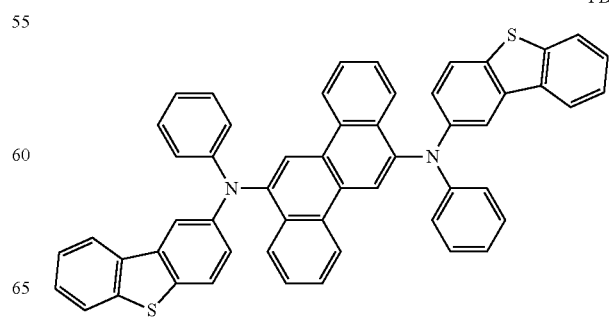

Compound FD9
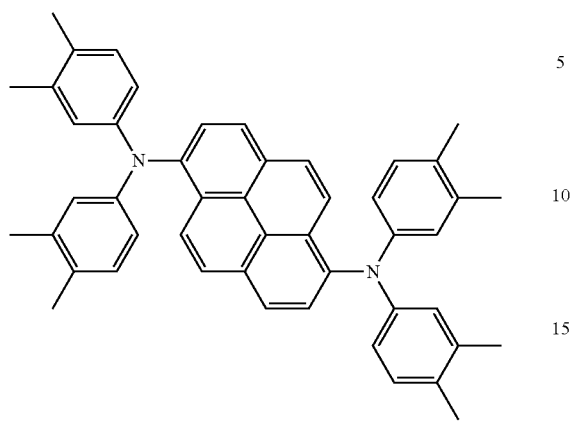
In some embodiments, the fluorescent dopant may be selected from the following compounds. However, embodiments of the fluorescent dopant are not limited thereto.
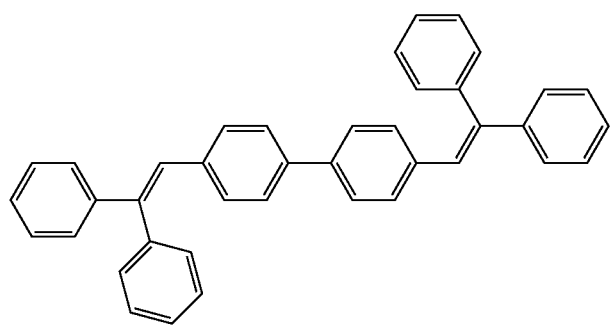
DPVBi
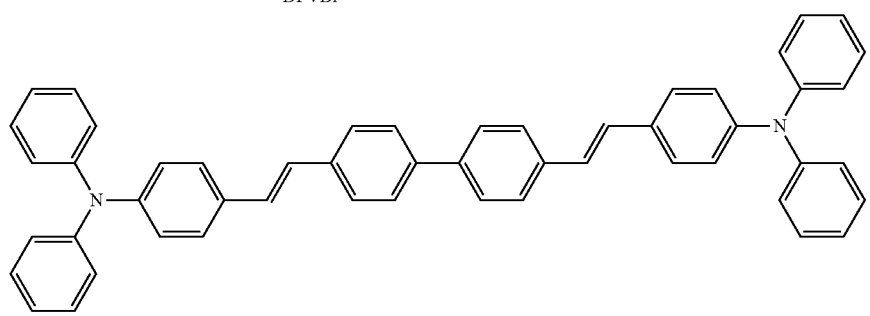
DPAVBi
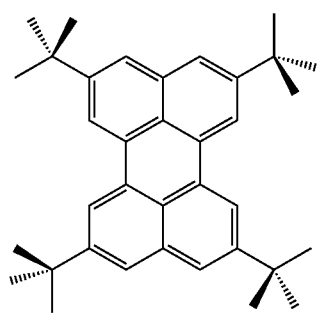
TBPe
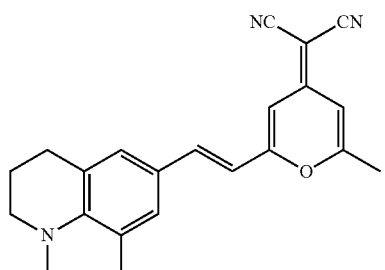
DCM
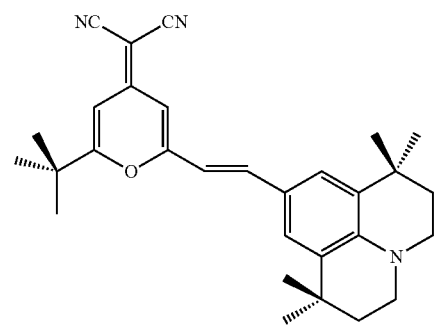
DCJTB

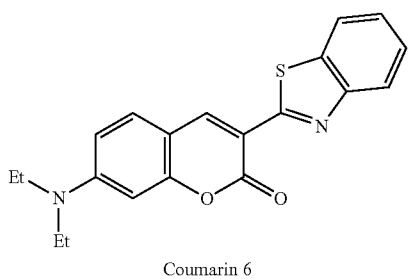

Coumarin 6

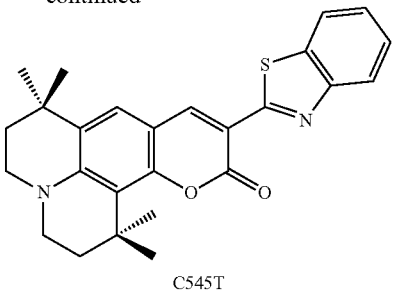

C545T

The amount of the dopant in the EML may be from about 0.01 parts to about 15 parts by weight based on 100 parts by weight of the host, but the amount is not limited to this range.

The thickness of the EML may be about 100 Å to about 1000 Å, and in some embodiments, may be from about 200 Å to about 600 Å. When the thickness of the EML is within these ranges, the organic light-emitting device may have good light emitting ability without a substantial increase in driving voltage.

Next, the electron transport region may be disposed on the EML.

The electron transport region may include at least one selected from a HBL, an ETL, and an EIL. However, embodiments of the present disclosure are not limited thereto.

In some embodiments, the electron transport region may have a structure including an ETL/EIL, or a HBL/ETL/EIL, wherein the layers forming a structure of the electron transport region may be sequentially stacked on the EML in the order stated above. However, embodiments of the present disclosure are not limited thereto.

In some embodiments, the organic layer 150 of the organic light-emitting device 10 may include the electron transport region between the EML and the second electrode 190.

When the electron transport region includes a HBL, the HBL may be formed on the EML by using any of a variety of suitable methods, for example, by using vacuum deposition, spin coating, casting, Langmuir-Blodgett (LB) deposition, inkjet printing, laser printing, laser induced thermal imaging (LITI), or the like. When the HBL is formed using vacuum deposition or spin coating, the deposition and coating conditions for forming the HBL may be similar to the above-described deposition and coating conditions for forming the HIL, and accordingly will not be repeated again here.

For example, the HBL may include at least one selected from BCP and Bphen. However, embodiments of the present disclosure are not limited thereto.

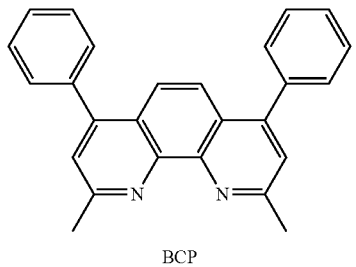

BCP

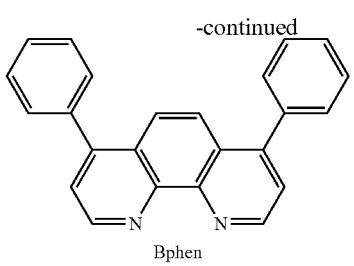

Bphen

The thickness of the HBL may be from about 20 Å to about 1,000 Å, and in some embodiments, from about 30 Å to about 300 Å. When the thickness of the HBL is within these ranges, the HBL may have improved hole blocking ability without a substantial increase in driving voltage.

The electron transport region may include an ETL. The ETL may be formed on the EML or the HBL by using any of a variety of suitable methods, for example, by using vacuum deposition, spin coating, casting, Langmuir-Blodgett (LB) deposition, inkjet printing, laser printing, laser induced thermal imaging (LITI), or the like. When the ETL is formed using vacuum deposition or spin coating, the deposition and coating conditions for forming the ETL may be similar to the above-described deposition and coating conditions for forming the HIL, and accordingly will not be repeated again here.

In some embodiments, the ETL may include at least one selected from a compound represented by Formula 601 and a compound represented by Formula 602.

$$Ar_{601}\text{-}[(L_{601})_{xe1}\text{-}E_{601}]_{xe2} \quad \text{Formula 601}$$

In Formula 601, $Ar_{601}$ may be selected from:

a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, naphthacene, a picene, a perylene, a pentaphene, and an indenoanthracene, and a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, naphthacene, a picene, a perylene, a pentaphene, and an indenoanthracene, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{301}$)($Q_{302}$)($Q_{303}$), wherein $Q_{301}$ to $Q_{303}$ may be each independently a hydrogen, a $C_1$-$C_{60}$ alkyl group, a $C_2$-$C_{60}$ alkenyl group, a $C_6$-$C_{60}$ aryl group, or a $C_1$-$C_{60}$ heteroaryl group;

$L_{601}$ may be defined the same as $L_{201}$ described herein;

$E_{601}$ may be selected from:

a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, and a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group;

xe1 may be selected from 0, 1, 2, and 3; and xe2 may be selected from 1, 2, 3, and 4.

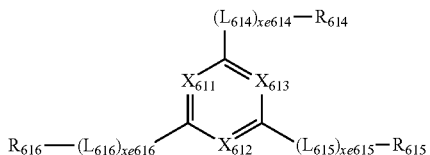

Formula 602

In Formula 602, $X_{611}$ may be N or C-($L_{611}$)$_{xe611}$-$R_{611}$; $X_{612}$ may be N or C-($L_{612}$)$_{xe612}$-$R_{612}$; $X_{613}$ may be N or C-($L_{613}$)$_{xe613}$-$R_{613}$; at least one of $X_{611}$ to $X_{613}$ may be N;

$L_{611}$ to $L_{616}$ may be each independently the same as $L_1$ described herein;

$R_{611}$ to $R_{616}$ may be each independently selected from:

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an azulenyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and xe611 to xe616 may be each independently selected from 0, 1, 2, and 3.

The compound represented by Formula 601 and the compound represented by Formula 602 may be each independently selected from Compounds ET1 to ET15.
ET1
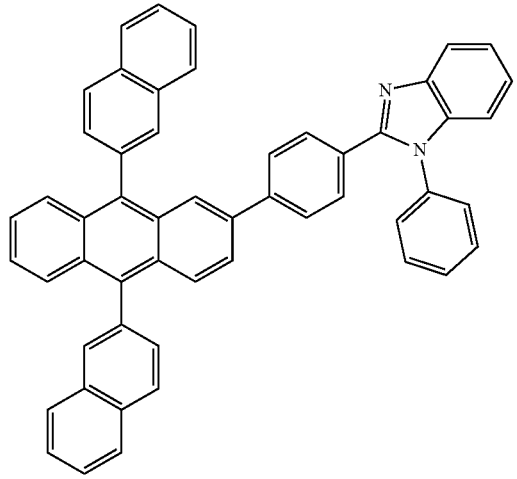
ET2
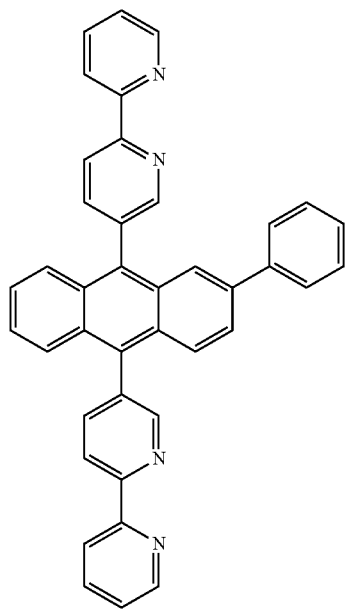
ET3
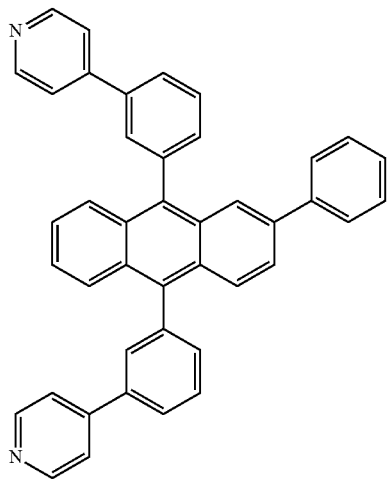
ET4
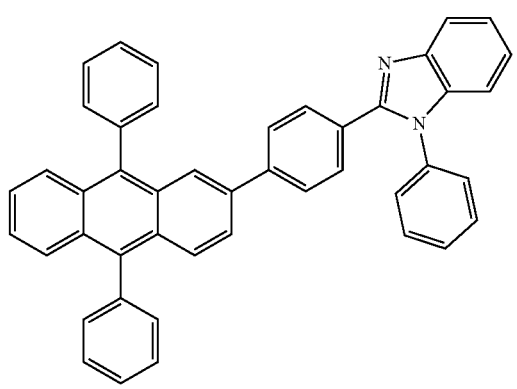
ET5
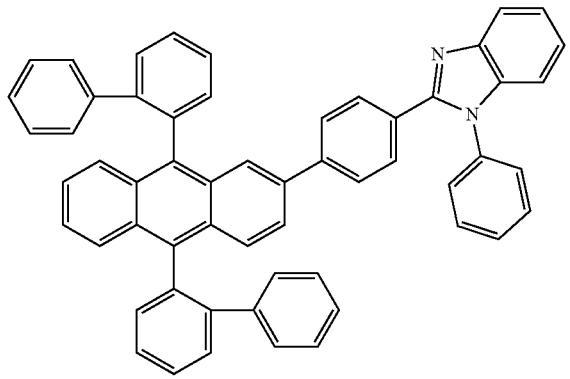

-continued
ET6
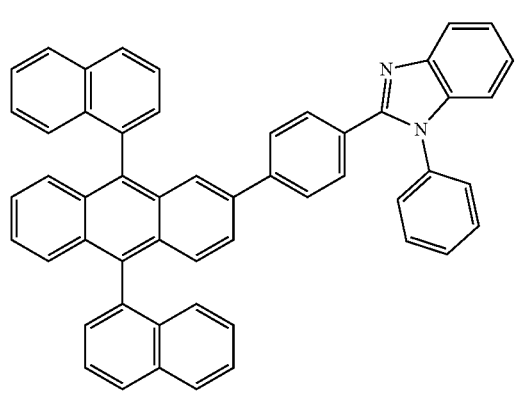
ET7
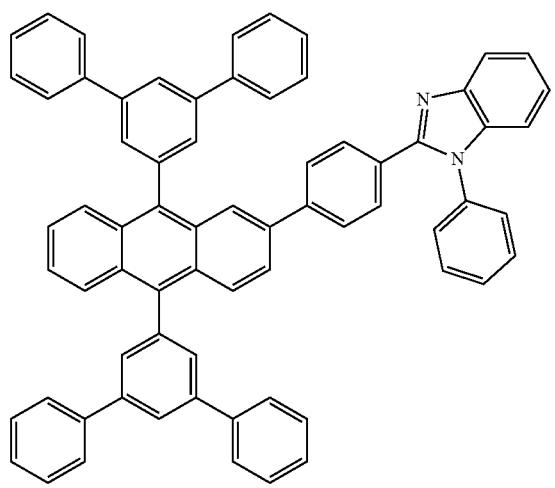
ET8
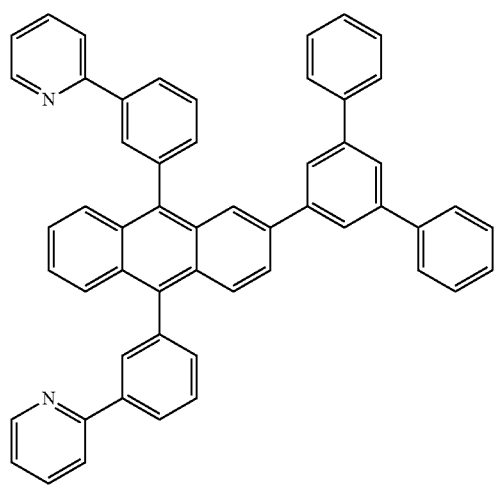
-continued
ET9
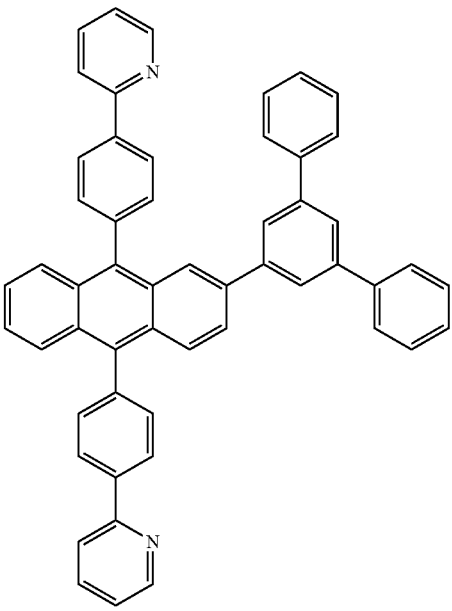
ET10
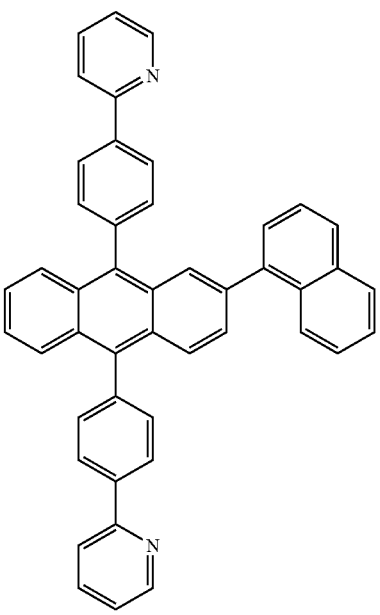

ET11
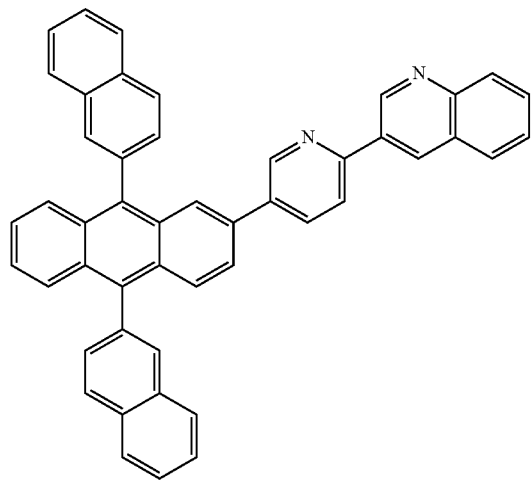
ET14
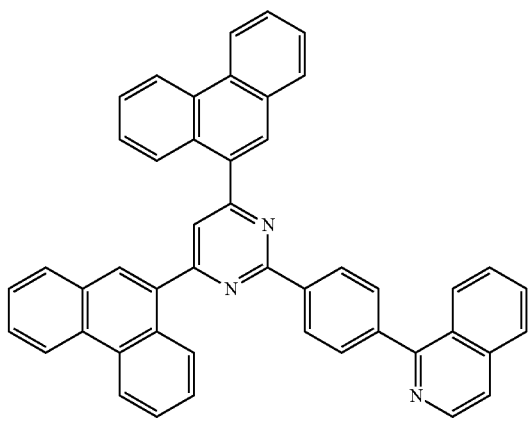
ET12
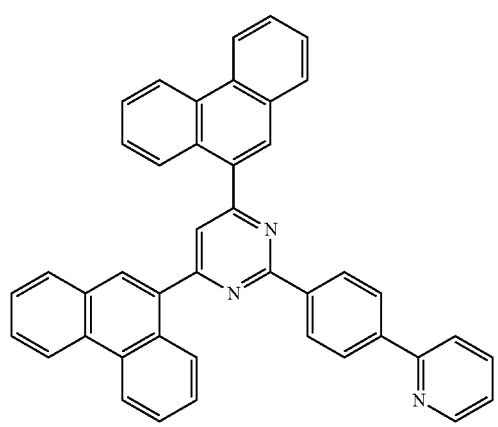
ET15
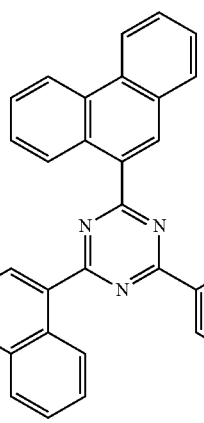
In some embodiments, the ETL may include at least one selected from BCP, Bphen, Alq$_3$, Balq, TAZ, and NTAZ.
ET13
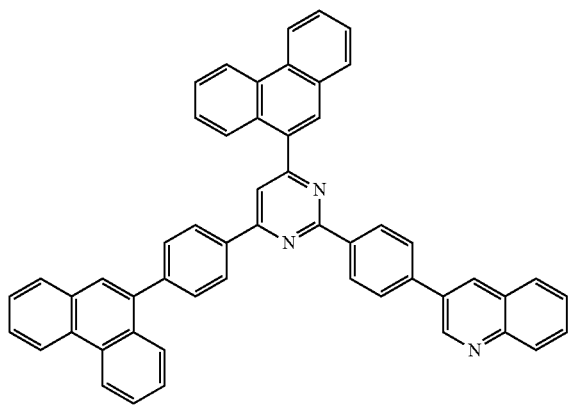
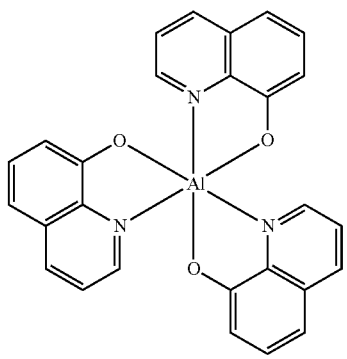
Alq$_3$

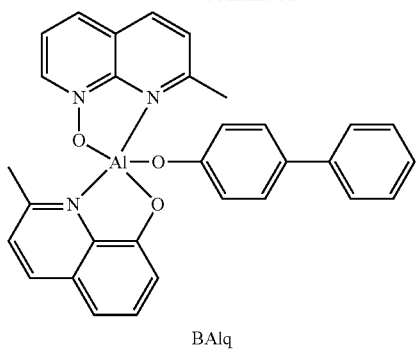

BAlq

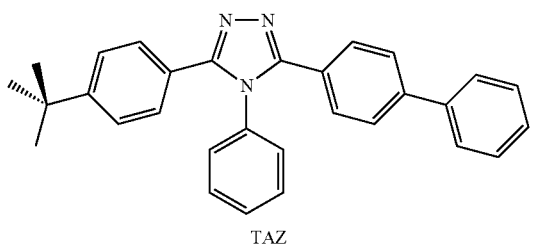

TAZ

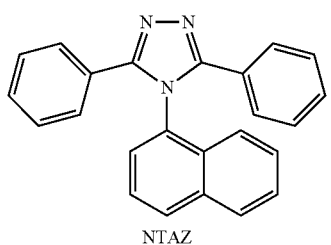

NTAZ

The thickness of the ETL may be from about 100 Å to about 1,000 Å, and in some embodiments, from about 150 Å to about 500 Å. When the thickness of the ETL is within these ranges, the organic light-emitting device may have suitable or satisfactory electron transporting ability without a substantial increase in driving voltage.

In some embodiments the ETL may further include a metal-containing material, in addition to the above-described materials.

The metal-containing material may include a lithium (Li) complex. Non-limiting examples of the Li complex include compound ET-D1 (lithium quinolate (LiQ)), and compound ET-D2.

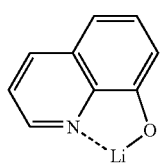 ET-D1

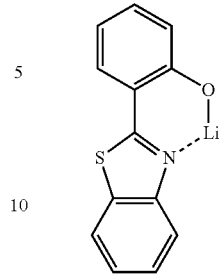 ET-D2

The electron transport region may include an EIL that may facilitate injection of electrons from the second electrode 190.

The EIL may be formed on the ETL by using any of a variety of suitable methods, for example, by using vacuum deposition, spin coating, casting, Langmuir-Blodgett (LB) deposition, inkjet printing, laser printing, laser induced thermal imaging (LITI), or the like. When the EIL is formed using vacuum deposition or spin coating, the deposition and coating conditions for forming the EIL may be similar to the above-described deposition and coating conditions for forming the HIL, and accordingly will not be repeated again here.

The EIL may include at least one selected from LiF, NaCl, CsF, $Li_2O$, BaO, and LiQ.

The thickness of the EIL may be from about 1 Å to about 100 Å, and in some embodiments, from about 3 Å to about 90 Å. When the thickness of the EIL is within these ranges, the EIL may have suitable or satisfactory electron injection ability without a substantial increase in driving voltage.

The second electrode 190 may be disposed on the organic layer 150, as described above. The second electrode 190 may be a cathode as an electron injecting electrode. A material for forming the second electrode 190 may be a metal, an alloy, an electrically conductive compound, which have a low-work function, or a mixture thereof. Non-limiting examples of materials for forming the second electrode 190 include lithium (Li), magnesium (Mg), aluminum (A), aluminum-lithium (Al—Li), calcium (Ca), magnesium-indium (Mg—In), and magnesium-silver (Mg—Ag). In some embodiments, a material for forming the second electrode 190 may be ITO or IZO. The second electrode 190 may be a semi-transmissive electrode or a transmissive electrode.

Figure 2:
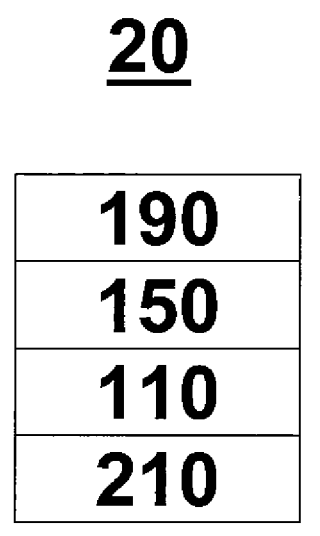
Figure 3:
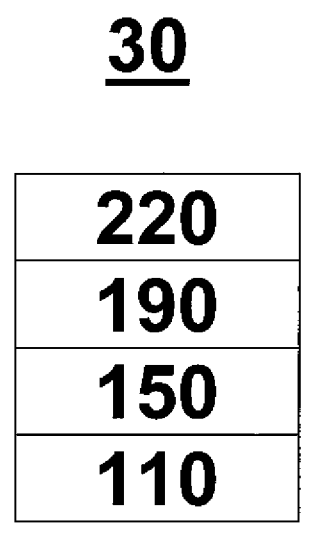
Figure 4:
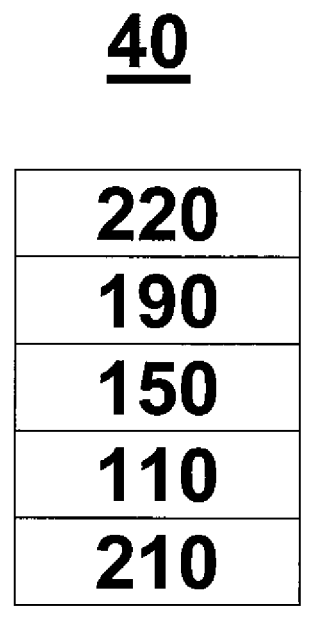

Referring to FIG. 2, an organic light-emitting device 20 according to an embodiment may have a stack structure in which a first capping layer 210, a first electrode 110, an organic layer 150, and a second electrode 190 are sequentially stacked upon one another in the stated order. Referring to FIG. 3, an organic light-emitting device 30 according to another embodiment may have a stack structure in which a first electrode 110, an organic layer 150, a second electrode 190, and a second capping layer 220 are sequentially stacked upon one another in the stated order. Referring to FIG. 4, an organic light-emitting device 40 may have a stack structure in which a first capping layer 210, a first electrode 110, an organic layer 150, a second electrode 190, and a second capping layer 220 are stacked upon one another in the stated order.

In FIGS. 2-4, the first electrode 110, the organic layer 150, and the second electrode 190 may be the same as those described above with reference to FIG. 1.

In the organic light-emitting devices 20 and 40, light generated in the emission layer of the organic layer 150 may be extracted outside the organic light-emitting device through the first electrode 110 as a semi-transmissive or transmissive electrode and the first capping layer 210. In the organic light-emitting devices 30 and 40, light generated in the emission layer of the organic layer 150 may be extracted outside the organic light-emitting device through the second electrode 190 as a semi-transmissive or transmissive electrode, and the second capping layer 220.

The first capping layer 210 and the second capping layer 220 may improve external emission efficiency based on the principle of constructive interference.

The first capping layer 210 of FIG. 2 and the second capping layer 220 of FIG. 3 may include the at least one of the condensed cyclic compound represented by Formula 1.

In the organic light-emitting device of FIG. 4, at least one selected from the first capping layer 210 and the second capping layer 220 may include the at least one of the condensed cyclic compound represented by Formula 1.

In some other embodiments, in the organic light-emitting devices 20, 30, and 40 of FIGS. 2-4, the organic layer 150 may not include the at least one of the condensed cyclic compound represented by Formula 1.

Although the organic light-emitting devices of FIGS. 1-4 are described above, embodiments of the present disclosure are not limited thereto.

As used herein, the term "a $C_1$-$C_{60}$ alkyl group" refers to a linear or branched aliphatic hydrocarbon monovalent group having 1 to 60 carbon atoms. Non-limiting examples of the $C_1$-$C_{60}$ alkyl group include a methyl group, an ethyl group, a propyl group, an isobutyl group, a sec-butyl group, a tert-butyl group, a pentyl group, an iso-amyl group, and a hexyl group. The term "a $C_1$-$C_{60}$ alkylene group," as used herein, refers to a divalent group having the same structure as the $C_1$-$C_{60}$ alkyl, except that the $C_1$-$C_{60}$ alkylene group is divalent instead of monovalent.

As used herein, the term "a $C_1$-$C_{60}$ alkoxy group" refers to a monovalent group represented by —$OA_{101}$ (where $A_{101}$ is a $C_1$-$C_{60}$ alkyl group as described above). Non-limiting examples of the $C_1$-$C_{60}$ alkoxy group include a methoxy group, an ethoxy group, and an isopropyloxy group.

As used herein, the term "a $C_2$-$C_{60}$ alkenyl group" refers to a hydrocarbon group including at least one carbon double bond in a main chain (e.g., in the middle) or terminal end of the $C_2$-$C_{60}$ alkyl group. Non-limiting examples of the $C_2$-$C_{60}$ alkenyl group include an ethenyl group, a propenyl group, and a butenyl group. The term "a $C_2$-$C_{60}$ alkenylene group," as used herein, refers to a divalent group having the same structure as the $C_2$-$C_{60}$ alkenyl group, except that the $C_2$-$C_{60}$ alkenylene group is divalent instead of monovalent.

As used herein, the term "a $C_2$-$C_{60}$ alkynyl group" refers to a hydrocarbon group including at least one carbon triple bond in a main chain (e.g., in the middle) or terminal end of the $C_2$-$C_{60}$ alkyl group. Non-limiting examples of the $C_2$-$C_{60}$ alkynyl group include an ethynyl group, and a propynyl group. The term "a $C_2$-$C_{60}$ alkynylene group," as used herein, refers to a divalent group having the same structure as the $C_2$-$C_{60}$ alkynyl group, except that the $C_2$-$C_{60}$ alkynylene group is divalent instead of monovalent.

As used herein, the term "a $C_3$-$C_{10}$ cycloalkyl group" refers to a monovalent, monocyclic hydrocarbon group having 3 to 10 carbon atoms. Non-limiting examples of the $C_3$-$C_{10}$ cycloalkyl group include a cyclopropyl group, a cyclobutyl group, a cyclopentyl group, a cyclohexyl group, and a cycloheptyl group. The term "a $C_3$-$C_{10}$ cycloalkylene group," as used herein, refers to a divalent group having the same structure as the $C_3$-$C_{10}$ cycloalkyl group, except that the $C_3$-$C_{10}$ cycloalkylene group is divalent instead of monovalent.

As used herein, the term "a $C_1$-$C_{10}$ heterocycloalkyl group" refers to a monovalent monocyclic group having 1 to 10 carbon atoms in which at least one hetero atom selected from N, O, P, and S is included as a ring-forming atom. Non-limiting examples of the $C_1$-$C_{10}$ heterocycloalkyl group include a tetrahydrofuranyl group, and a tetrahydrothiophenyl group. The term "a $C_1$-$C_{10}$ heterocycloalkylene group," as used herein, refers to a divalent group having the same structure as the $C_1$-$C_{10}$ heterocycloalkyl group, except that the $C_1$-$C_{10}$ heterocycloalkylene group is divalent instead of monovalent.

As used herein, the term "a $C_3$-$C_{10}$ cycloalkenyl group" refers to a monovalent monocyclic group having 3 to 10 carbon atoms that includes at least one double bond in the ring but does not have aromaticity (e.g., the ring is not aromatic). Non-limiting examples of the $C_3$-$C_{10}$ cycloalkenyl group include a cyclopentenyl group, a cyclohexenyl group, and a cycloheptenyl group. The term "a $C_3$-$C_{10}$ cycloalkenylene group," as used herein, refers to a divalent group having the same structure as the $C_3$-$C_{10}$ cycloalkenyl group, except that the $C_3$-$C_{10}$ cycloalkenylene group is divalent instead of monovalent.

As used herein, the term "a $C_1$-$C_{10}$ heterocycloalkenyl group" refers to a monovalent monocyclic group having 1 to 10 carbon atoms that includes at least one double bond in the ring and in which at least one hetero atom selected from N, O, Si, P, and S is included as a ring-forming atom. Non-limiting examples of the $C_1$-$C_{10}$ heterocycloalkenyl group include a 2,3-dihydrofuranyl group, and a 2,3-dihydrothiophenyl group. The term "a $C_1$-$C_{10}$ heterocycloalkenylene group," as used herein, refers to a divalent group having the same structure as the $C_1$-$C_{10}$ heterocycloalkenyl group, except that the $C_1$-$C_{10}$ heterocycloalkenylene group is divalent instead of monovalent.

As used herein, the term "a $C_6$-$C_{60}$ aryl group" refers to a monovalent, aromatic carbocyclic aromatic group having 6 to 60 carbon atoms, and a $C_6$-$C_{60}$ arylene group refers to a divalent, aromatic carbocyclic group having 6 to 60 carbon atoms. Non-limiting examples of the $C_6$-$C_{60}$ aryl group include a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group include at least two rings, the rings may be fused to each other (e.g., combined together).

As used herein, the term "a $C_1$-$C_{60}$ heteroaryl group" refers to a monovalent, aromatic carbocyclic aromatic group having 1 to 60 carbon atoms in which at least one hetero atom selected from N, O, Si, P, and S is included as a ring-forming atom. A $C_1$-$C_{60}$ heteroarylene group refers to a divalent, aromatic carbocyclic group having 1 to 60 carbon atoms in which at least one hetero atom selected from N, O, Si, P, and S is included as a ring-forming atom. Non-limiting examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl and the $C_1$-$C_{60}$ heteroarylene include at least two rings, the rings may be fused to each other (e.g., combined together).

As used herein, the term "a $C_6$-$C_{60}$ aryloxy group" refers to —$OA_{102}$ (where $A_{102}$ is a $C_6$-$C_{60}$ aryl group as described above), and a $C_6$-$C_{60}$ arylthio group refers to —$SA_{103}$ (where $A_{103}$ is a $C_6$-$C_{60}$ aryl group as described above).

As used herein, the term "a monovalent non-aromatic condensed polycyclic group" refers to a monovalent group having at least two rings condensed to each other (e.g., combined together), in which only carbon atoms (for example, 8 to 60 carbon atoms) are exclusively included as ring-forming atoms and the entire molecule has non-aromaticity (e.g., the entire molecule is non-aromatic). A non-limiting example of the monovalent non-aromatic condensed polycyclic group is a fluorenyl group. The term "a divalent non-aromatic condensed polycyclic group" refers to a divalent group having the same structure as the monovalent non-aromatic condensed polycyclic group, except that divalent non-aromatic condensed polycyclic group is divalent instead of monovalent.

As used herein, the term "a monovalent non-aromatic condensed heteropolycyclic group" refers to a monovalent group having at least two rings condensed to each other (e.g., combined together), in which carbon atoms (for example, 1 to 60 carbon atoms) and a hetero atom selected from N, O, Si, P, and S are as ring-forming atoms and the entire molecule has non-aromaticity (e.g., the entire molecule is non-aromatic). A non-limiting example of the monovalent non-aromatic condensed heteropolycyclic group is a carbazolyl group. As used herein, the term "a divalent non-aromatic condensed heteropolycyclic group" refers to a divalent group having the same structure as the monovalent non-aromatic condensed heteropolycyclic group, except that the divalent non-aromatic condensed heteropolycyclic group is divalent instead of monovalent.

As described herein, the at least one substituent of the substituted condensed polycyclic group including at least three carbocyclic groups condensed together, the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group, may be selected from:

a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group, a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxyl group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), and —B($Q_{16}$)($Q_{17}$), a $C_3$-$C_{10}$ cycloalkyl group, a $C_1$-$C_{60}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$), and —N($Q_{31}$)($Q_{32}$), —Si($Q_{33}$)($Q_{34}$)($Q_{35}$), and —B($Q_{36}$)($Q_{37}$), wherein $Q_1$ to $Q_7$, $Q_{11}$ to $Q_{17}$, $Q_{21}$ to $Q_{27}$, and $Q_{31}$ to $Q_{37}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

The abbreviation "Ph," as used herein, refers to phenyl (a phenyl group), the abbreviation "Me," as used herein, refers to methyl (a methyl group), the abbreviation "Et," as used herein, refers to ethyl, and the abbreviations "ter-Bu" and "Bu$^t$," as used herein, refer to tert-butyl.

One or more embodiments of the present disclosure, which include the condensed cyclic compound, and organic light-emitting devices including the same, will now be described in more detail with reference to the following examples. However, these examples are only for illustrative purposes and are not intended to limit the scope of the one or more embodiments of the present disclosure. In the following synthesis examples, the expression that "'B', instead of 'A', was used" means that the amounts of 'B' and 'A' were the same in equivalent amounts.

EXAMPLES

Synthesis Example 1

Synthesis of Compound 1

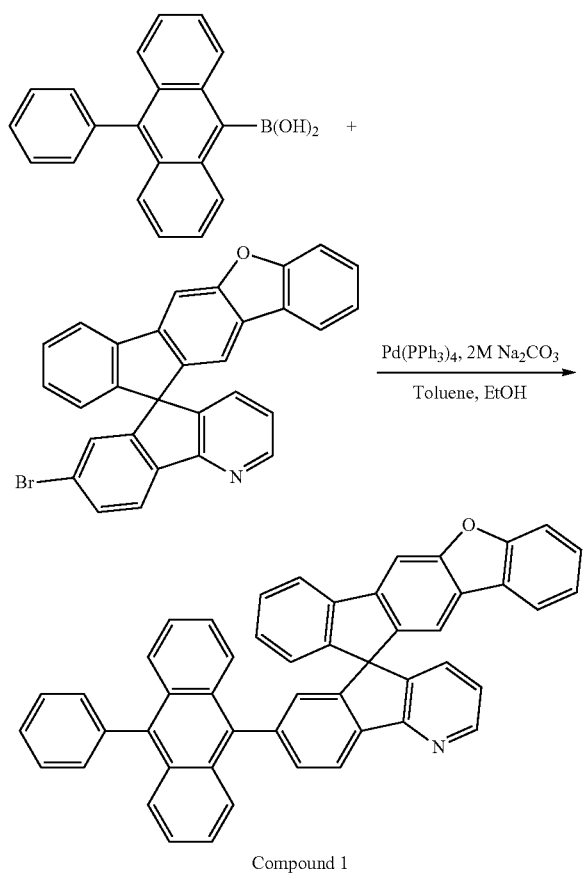

Compound 1

0.63 g (1 eq, 1.30 mmol) of 7'-bromospiro[fluoreno[3,2-b]benzofuran-11,5'-indeno[1,2-c]pyridine], 0.43 g (1.1 eq, 1.43 mmol) of 10-phenylanthracen-9-yl)boronic acid, and 0.06 g of (0.04 eq, 0.052 mmol) of tetrakis(triphenylphosphine)palladium(0) were put in a flask, dried under vacuum, and then purged with nitrogen gas. After 13 mL of toluene was added to the flask to dissolve the starting materials, 6.5 mL of ethanol and 6.5 mL (10 eq, 13.0 mmol) of a 2.0M sodium carbonate aqueous solution were added thereto and stirred under reflux at about 80° C. for about 3 hours. After termination of the reaction, the resulting reaction product was washed with distilled water, followed by extraction with ethyl acetate to obtain an organic phase. The obtained product was dried using magnesium sulfate, filtered using a Celite, and then purified using silica gel column chromatography to obtain Compound 1 (7'-(10-phenylanthracen-9-yl)spiro[fluoreno[3,2-b]benzofuran-11,5'-indeno[1,2-c]pyridine]) 0.67 g (Yield: 75%).

$^1$H NMR: 9.24 (1H), 8.06 (2H), 7.91 (6H), 7.73 (3H), 7.51 (5H), 7.40 (6H), 7.35 (3H), 7.24 (1H), 7.03 (2H), atmospheric-pressure chemical ionization mass spectrometry (APCI-MS) (m/z): 659 [M$^+$]

Synthesis Example 2

Synthesis of Compound 2

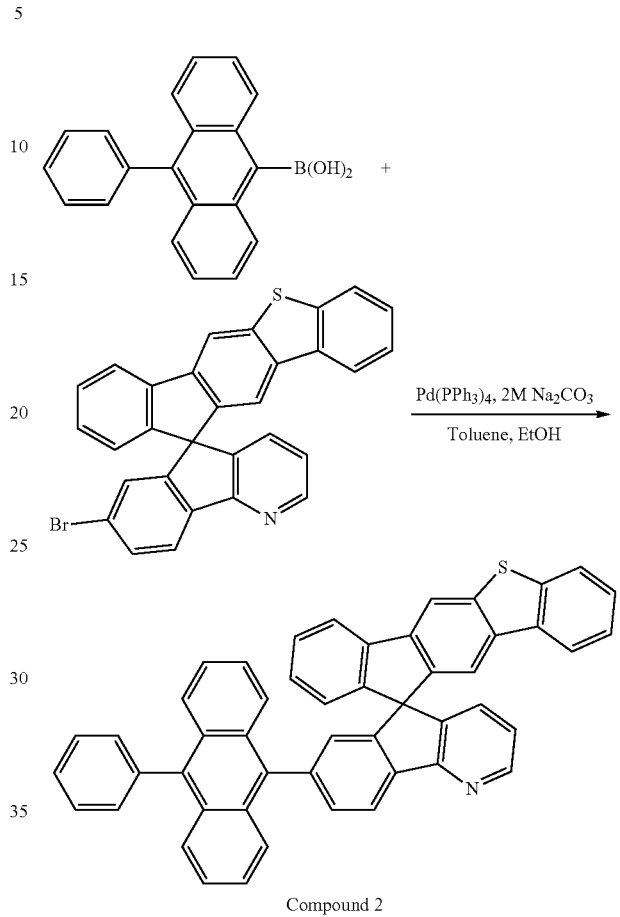

Compound 2

0.65 g (Yield: 70%) of Compound 2 (7'-(10-phenylanthracen-9-yl)spiro[benzo[b]fluoreno[2,3-d]thiophene-11,5'-indeno[1,2-c]pyridine]) was obtained in the same manner as described with respect to Synthesis Example 1, except that 7'-bromospiro[benzo[b]fluoreno[2,3-d]thiophene-11,5'-indeno[1,2-c]pyridine], instead of 7'-bromospiro[fluoreno[3,2-b]benzofuran-11,5'-indeno[1,2-c]pyridine], was used.

$^1$H NMR: 9.24 (1H), 8.45 (1H), 7.98 (2H), 9.91 (4H), 7.85 (1H), 7.73 (1H), 7.67 (1H), 7.51 (6H), 7.40 (5H), 7.24 (1H), 7.06 (2H), APCI-MS (m/z): 675 [M$^+$]

Synthesis Example 3

Synthesis of Compound 7

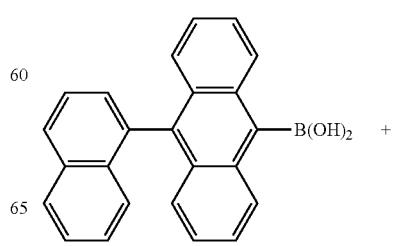

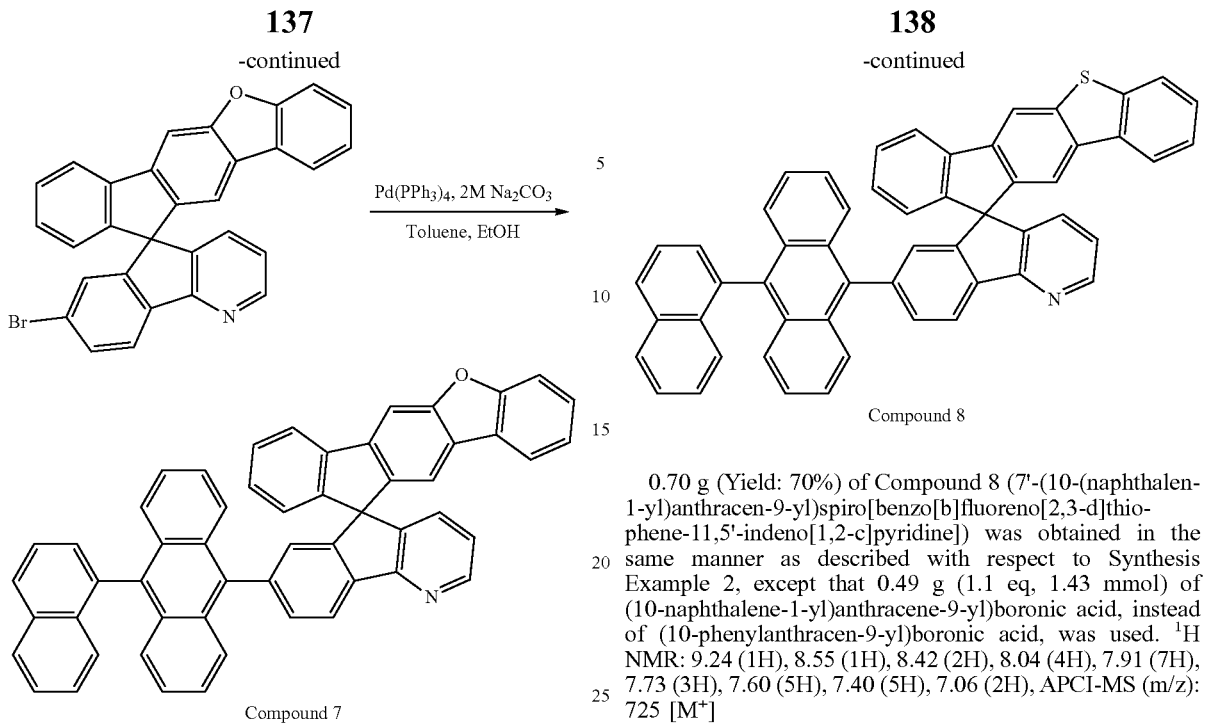

Compound 7

0.68 g (Yield: 70%) of Compound 7 (7'-(10-(naphthalen-1-yl)anthracen-9-yl)spiro[fluoreno[3,2-b]benzofuran-11,5'-indeno[1,2-c]pyridine]) was obtained in the same manner as described with respect to Synthesis Example 1, except that 0.49 g (1.1 eq, 1.43 mmol) of (10-naphthalene-1-yl)anthracene-9-yl)boronic acid, instead of (10-phenylanthracen-9-yl)boronic acid, was used.

$^1$H NMR: 9.24 (1H), 8.55 (1H), 8.42 (1H), 8.04 (4H), 7.91 (6H), 7.60 (7H), 7.40 (7H), 7.06 (2H), APCI-MS (m/z): 709 [M$^+$]

Synthesis Example 4

Synthesis of Compound 8

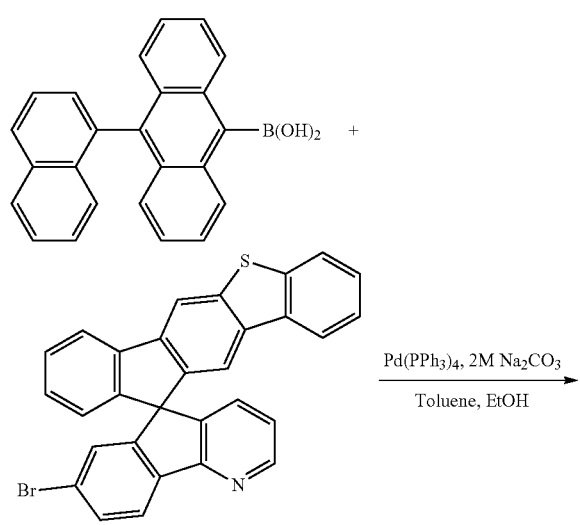

Compound 8

0.70 g (Yield: 70%) of Compound 8 (7'-(10-(naphthalen-1-yl)anthracen-9-yl)spiro[benzo[b]fluoreno[2,3-d]thiophene-11,5'-indeno[1,2-c]pyridine]) was obtained in the same manner as described with respect to Synthesis Example 2, except that 0.49 g (1.1 eq, 1.43 mmol) of (10-naphthalene-1-yl)anthracene-9-yl)boronic acid, instead of (10-phenylanthracen-9-yl)boronic acid, was used. $^1$H NMR: 9.24 (1H), 8.55 (1H), 8.42 (2H), 8.04 (4H), 7.91 (7H), 7.73 (3H), 7.60 (5H), 7.40 (5H), 7.06 (2H), APCI-MS (m/z): 725 [M$^+$]

Example 1

A 15 Ω/cm$^2$ ITO glass substrate (having a thickness of 1200 Å, available from Corning) was cut to a size of 50 mm×50 mm×0.7 mm and then sonicated in isopropyl alcohol and deionized water each for five minutes, and then cleaned by irradiation with ultraviolet rays for 30 minutes and exposure to ozone. The resulting glass substrate including an ITO anode was mounted into a vacuum deposition device.

2-TNATA was vacuum-deposited on the ITO anode of the glass substrate to form a hole injection layer (HIL) having a thickness of 600 Å, and 4,4'-bis[N-(1-naphthyl)-N-phenylamino]biphenyl (hereinafter, "NPB") was then vacuum-deposited on the HIL to form a hole transport layer (HTL) having a thickness of about 300 Å.

Compound 1 (as a host) and DPAVBi (as a dopant) were co-deposited on the HTL in a weight ratio of about 95:5 to form an emission layer (EML) having a thickness of about 20 nm.

Compound ET1 was deposited on the EML to form an electron transport layer (ETL) having a thickness of about 300 Å, and then LiF was deposited on the ETL to form an electron injection layer (EIL) having a thickness of about 10 Å. Aluminum (Al) was then vacuum-deposited on the EIL to form a cathode having a thickness of about 3000 Å, thereby completing the manufacture of an organic light-emitting device.

Examples 2 to 4 and Comparative Examples 1 to 4

Organic light-emitting devices were manufactured in the same manner as described with respect to Example 1, except that the compounds listed in Table 1, instead of Compound 1 of Example 1, were used, respectively, as a host to form the ETL.

Evaluation Example 1

Driving voltages, current densities, luminances, and efficiencies of the organic light-emitting devices of Examples 1 to 4 and Comparative Examples 1 to 4 were evaluated using a Keithley Source-Measure Unit (SMU 236) and a PR650 (Spectroscan) Source Measurement Unit (available from Photo Research, Inc.). The results are shown in Table 1.

TABLE 1

| Example | Host | Driving voltage (V) | Current density (mA/cm$^2$) | Luminance (cd/m$^2$) | Efficiency (cd/A) |
|---|---|---|---|---|---|
| Example 1 | Compound 1 | 3.5 | 10 | 531 | 5.31 |
| Example 2 | Compound 2 | 3.6 | 10 | 489 | 4.89 |
| Example 3 | Compound 7 | 3.5 | 10 | 487 | 4.87 |
| Example 4 | Compound 8 | 3.7 | 10 | 476 | 4.76 |
| Comparative Example 1 | Compound A | 4.6 | 10 | 311 | 3.11 |
| Comparative Example 2 | Compound B | 4.3 | 10 | 367 | 3.67 |
| Comparative Example 3 | Compound C | 4.2 | 10 | 416 | 4.16 |
| Comparative Example 4 | Compound D | 3.8 | 10 | 256 | 2.56 |

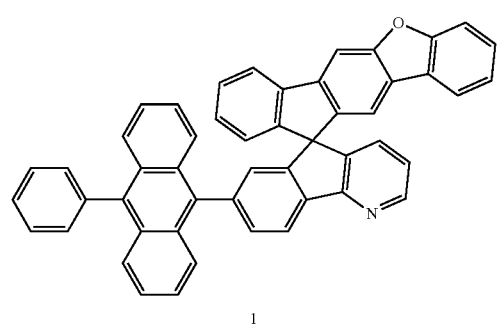 [SMILES: c1ccc(-c2c3ccccc3c(-c3ccc4c(c3)C3(c5ccccc5-c5cc6oc7ccccc7c6cc53)c3cccnc3-4)c3ccccc23)cc1]

1

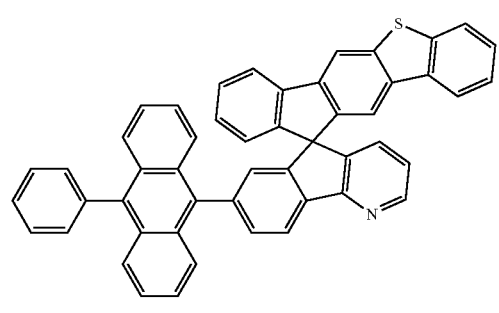

2

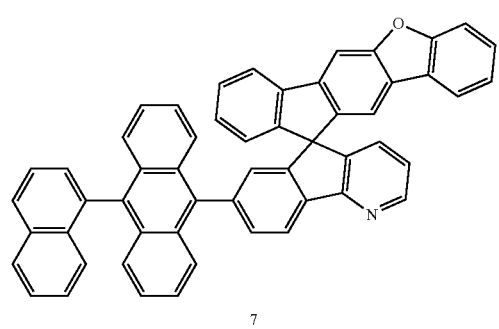 [SMILES: c1ccc2c(c1)-c1cc3oc4ccccc4c3cc1C21c2cc(-c3c4ccccc4c(-c4cccc5ccccc45)c4ccccc34)ccc2-c2ncccc21]

7

8

Compound A

Compound B

Compound C

Compound D

Referring to Table 1, the organic light-emitting devices of Examples 1 to 4 were found to have improved driving voltages, improved luminances, and improved efficiencies, as compared to those of the organic light-emitting devices of Comparative Examples 1 to 4.

As described above, according to one or more of the above embodiments of the present disclosure, an organic light-emitting device including a condensed cyclic compound represented by Formula 1 may have a low driving voltage, a high efficiency and a high luminance.

As used herein, the terms "substantially," "about," and similar terms are used as terms of approximation and not as terms of degree, and are intended to account for the inherent deviations in measured or calculated values that would be recognized by those of ordinary skill in the art. Also, any numerical range recited herein is intended to include all sub-ranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein, and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

It should be understood that the example embodiments described herein should be considered in a descriptive sense, and the present disclosure should not be limited thereto. Descriptions of features or aspects within each embodiment should typically be considered as available for other similar features or aspects in other embodiments.

While one or more embodiments of the present disclosure have been described with reference to the figures, it will be understood by those of ordinary skill in the art that various changes in form and details may be made therein without departing from the spirit and scope of the present invention as defined by the following claims, and equivalents thereof.

What is claimed is:

1. A condensed cyclic compound represented by one of Formulae 1A or 1C to 1E:

Formula 1A

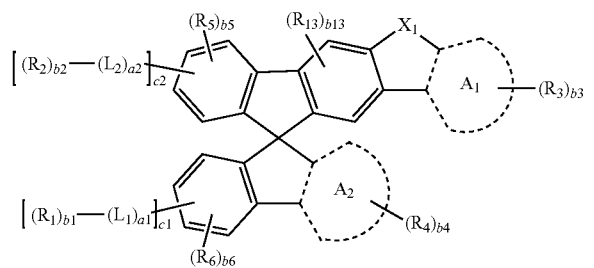

Formula 1C

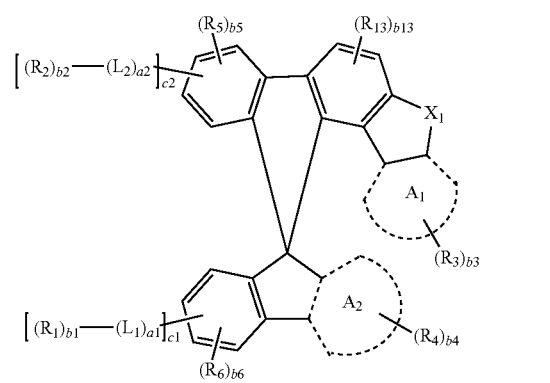

Formula 1D

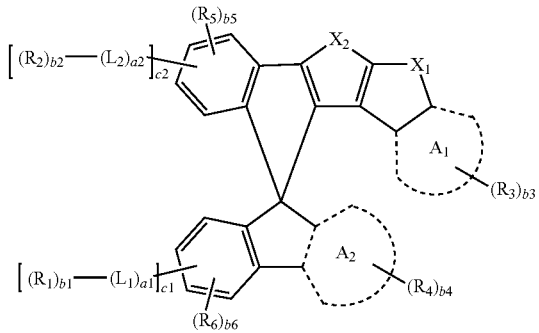

Formula 1E

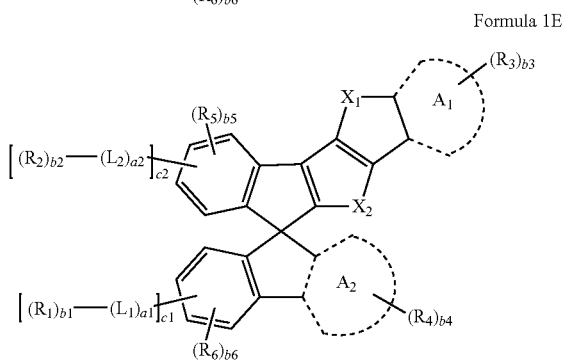

wherein, in Formulae 1A and 1C to 1E $A_1$ ring is selected from a benzene, a naphthalene, a pyridine, a pyrimidine, a pyrazine, a quinoline, an isoquinoline, a quinoxaline, a quinazoline, and a cinnoline;

$A_2$ ring is a pyridine;

$X_1$ is O, or S;

$X_2$ is N-[$(L_{12})_{a12}$-$(R_{12})_{b12}$], O, or S;

a1 and a2 are each independently an integer selected from 1 to 5, wherein, when a1 is 2 or greater, at least two $L_1$s are the same or different, and when a2 is 2 or greater, at least two $L_2$s are the same or different;

$L_{12}$ is selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group;

a12 is an integer selected from 0 to 5, wherein, when a12 is 2 or greater, at least two $L_{12}$s are the same or different;

$R_1$ and $R_2$ are each an unsubstituted or substituted $C_1$-$C_{60}$ heteroaromatic ring or an unsubstituted or substituted $C_6$-$C_{60}$ aromatic ring wherein the unsubstituted or substituted heteroaromatic ring and the unsubstituted or substituted aromatic ring are not substituted with an amino group;

$R_3$ to $R_6$ and $R_{12}$ to $R_{13}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), and —B($Q_6$)($Q_7$);

b1, b2, b5, b6, and b12 are each independently an integer selected from 0 to 4;

b3 is an integer selected from 0 to 6;

b4 is an integer selected from 0 to 3;

b13 is 0, 1, or 2;

c1 is an integer selected from 1 to 4;

c2 is an integer selected from 0 to 4;

at least one substituent of the substituted condensed polycyclic group including at least three carbocyclic groups condensed together, the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group is selected from:

a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group, a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), and —B($Q_{16}$)($Q_{17}$), a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$), and —N($Q_{31}$)($Q_{32}$), —Si($Q_{33}$)($Q_{34}$)($Q_{35}$), and —B($Q_{36}$)($Q_{37}$), wherein $Q_1$ to $Q_7$, $Q_{11}$ to $Q_{17}$, $Q_{21}$ to $Q_{27}$, and $Q_{31}$ to $Q_{37}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group, and wherein $L_1$ is selected from:

a phenalenylene group, a fluoranthenylene group, and a perylenylene group, and a phenalenylene group, a fluoranthenylene group, and a perylenylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, and —Si(Q$_{33}$)(Q$_{34}$)(Q$_{35}$), wherein Q$_{33}$ to Q$_{35}$ are each independently selected from a C$_1$-C$_{10}$ alkyl group, a C$_1$-C$_{10}$ alkoxy group, a phenyl group, and a naphthyl group, and wherein L$_2$ is selected from:
a phenalenylene group, an anthracenylene group, a fluoranthenylene group, and a perylenylene group, and
a phenalenylene group, an anthracenylene group, a fluoranthenylene group, and a perylenylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{20}$ alkyl group, a C$_1$-C$_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, and —Si(Q$_{33}$)(Q$_{34}$)(Q$_{35}$), wherein Q$_{33}$ to Q$_{35}$ are each independently selected from a C$_1$-C$_{10}$ alkyl group, a C$_1$-C$_{10}$ alkoxy group, a phenyl group, and a naphthyl group.

2. The condensed cyclic compound of claim 1, wherein the A$_1$ ring is selected from a benzene, a naphthalene, a pyridine, a quinoline, and an isoquinoline.

3. The condensed cyclic compound of claim 1, wherein L$_{12}$ are each independently selected from groups respectively represented by Formulae 3-1 to 3-41:

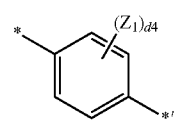

Formula 3-1

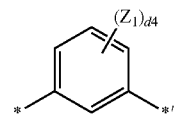

Formula 3-2

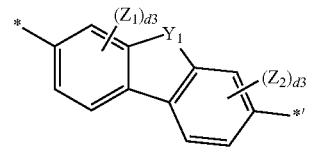

Formula 3-3

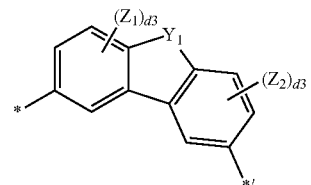

Formula 3-4

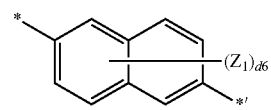

Formula 3-5

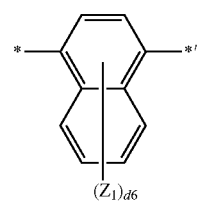

Formula 3-6

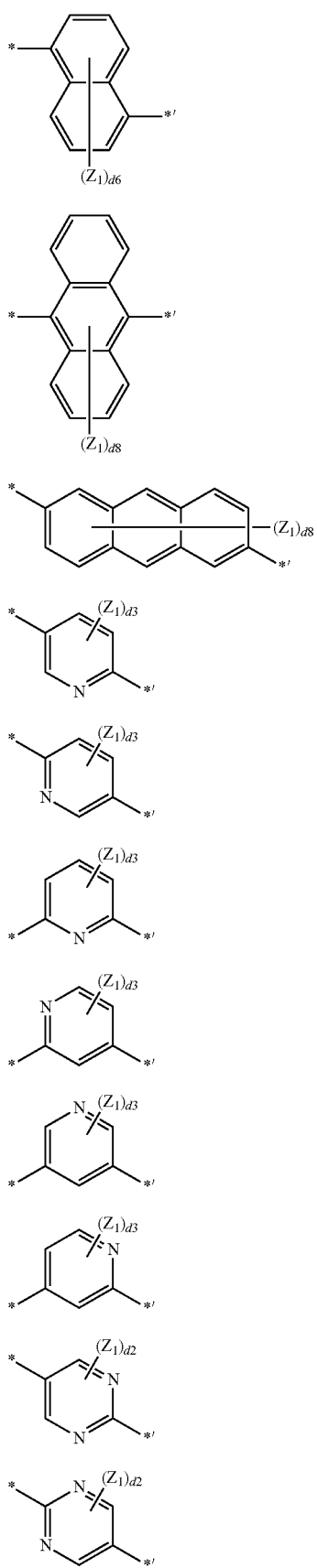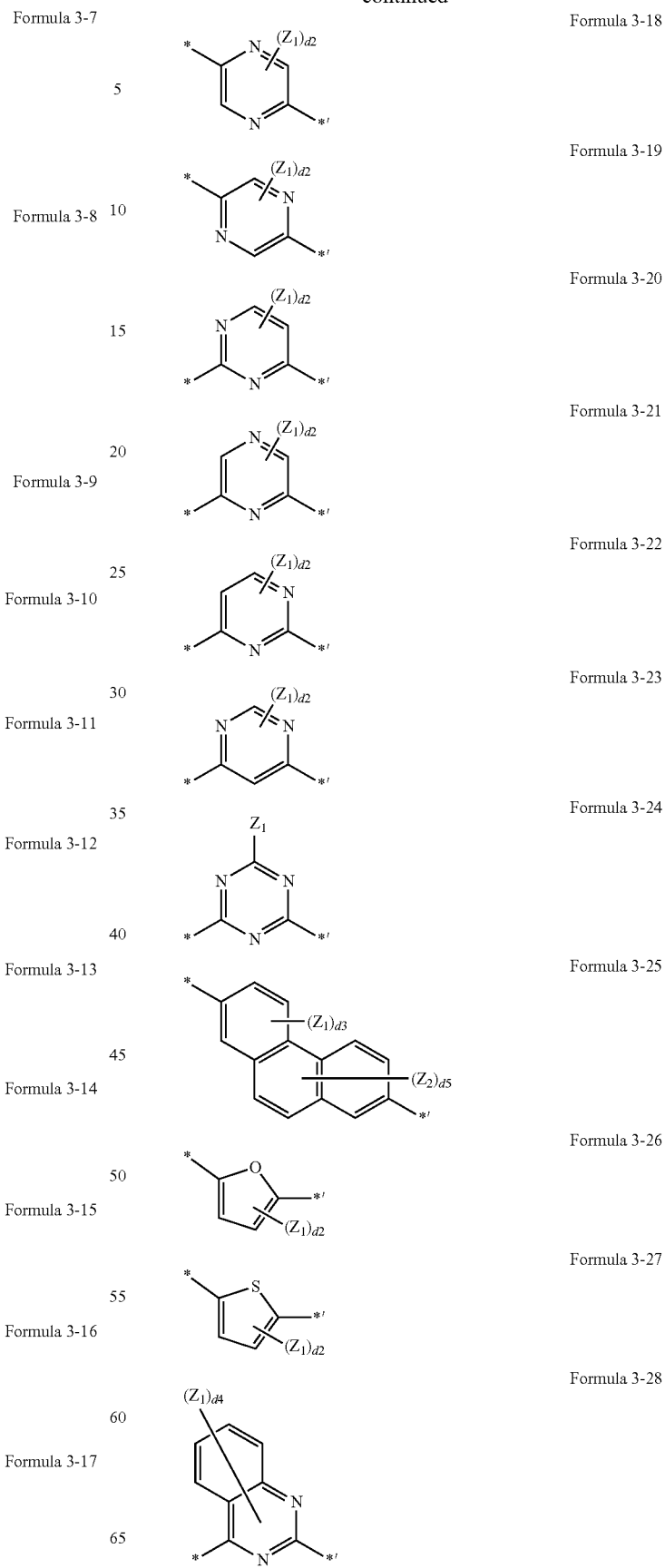

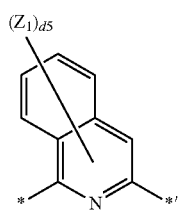
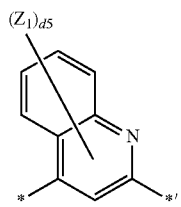
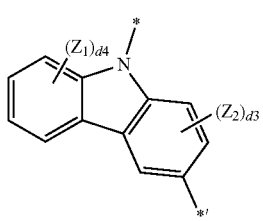
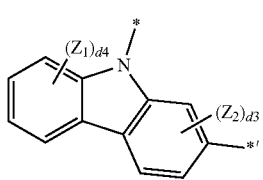
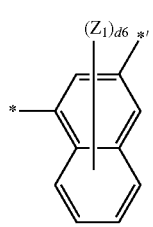
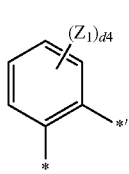
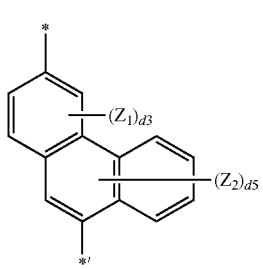
Formula 3-29
Formula 3-30
Formula 3-31
Formula 3-32
Formula 3-33
Formula 3-34
Formula 3-35
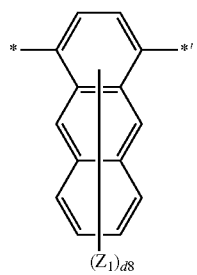
Formula 3-36
Formula 3-37
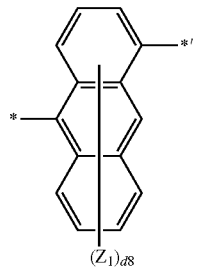
Formula 3-38
Formula 3-39
Formula 3-40

-continued

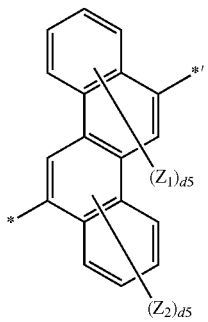

Formula 3-41 wherein, in Formulae 3-1 to 3-41, $Y_1$ is O, S, $C(Z_3)(Z_4)$, $N(Z_5)$, or $Si(Z_6)(Z_7)$;

$Z_1$ to $Z_7$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, and —$Si(Q_{33})(Q_{34})(Q_{35})$, wherein $Q_{33}$ to $Q_{35}$ are each independently selected from a $C_1$-$C_{10}$ alkyl group, a $C_1$-$C_{10}$ alkoxy group, a phenyl group, and a naphthyl group;

d2 is 1 or 2;
d3 is an integer selected from 1 to 3;
d4 is an integer selected from 1 to 4;
d5 is an integer selected from 1 to 5;
d6 is an integer selected from 1 to 6;
d8 is an integer selected from 1 to 8; and
* and *' are binding sites with an adjacent atom.

4. The condensed cyclic compound of claim 1, wherein $L_{12}$ is selected from groups respectively represented by Formulae 4-1 to 4-35:

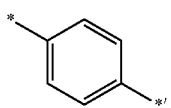

Formula 4-1

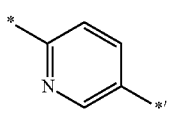

Formula 4-2

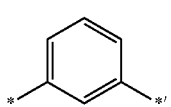

Formula 4-3

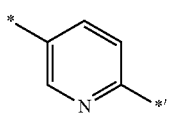

Formula 4-4

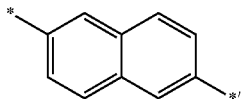

Formula 4-5

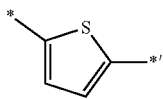

Formula 4-6

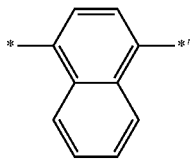

Formula 4-7

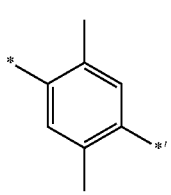

Formula 4-8

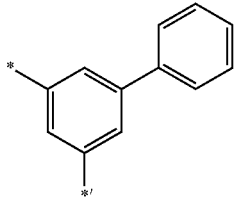

Formula 4-9

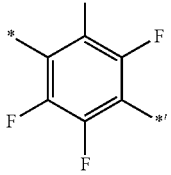

Formula 4-10

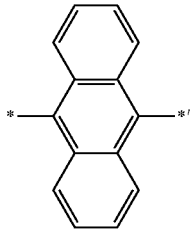

Formula 4-11

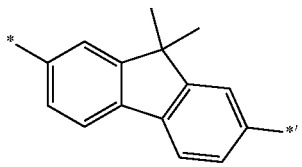

Formula 4-12

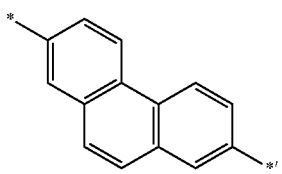

Formula 4-13

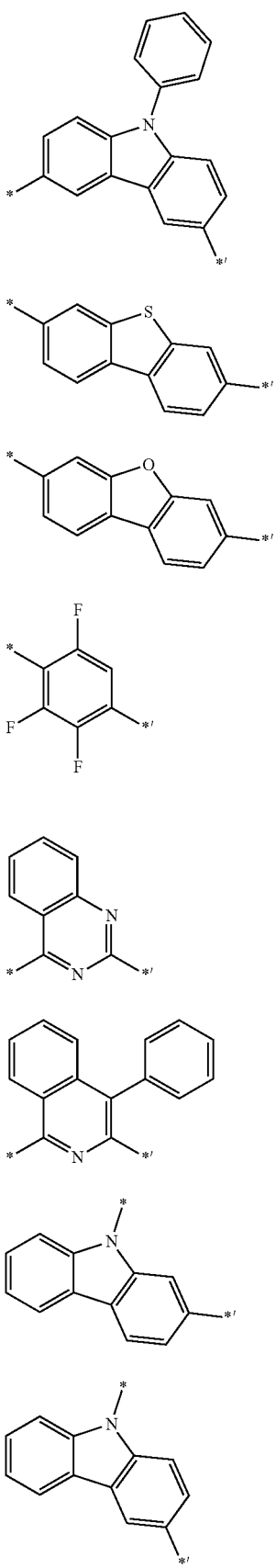
Formula 4-14
Formula 4-15
Formula 4-16
Formula 4-17
Formula 4-18
Formula 4-19
Formula 4-20
Formula 4-21
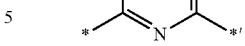
Formula 4-22
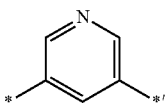
Formula 4-23
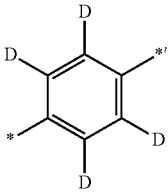
Formula 4-24
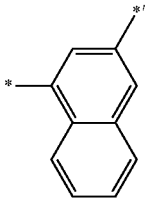
Formula 4-25
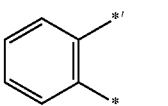
Formula 4-26
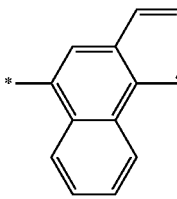
Formula 4-27
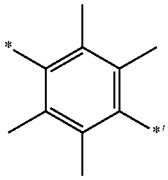
Formula 4-28
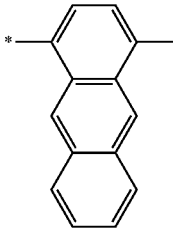
Formula 4-29
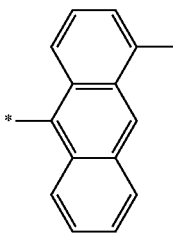
Formula 4-30

-continued

Formula 4-31
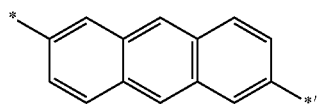

Formula 4-32
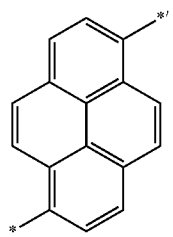

Formula 4-33
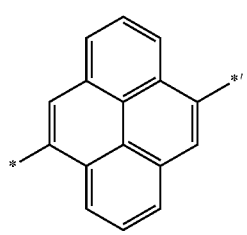

Formula 4-34
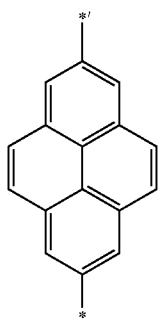

Formula 4-35
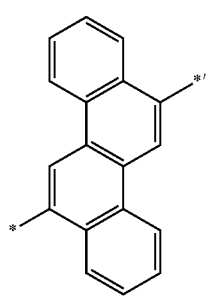

wherein, in Formulae 4-1 to 4-35, * and *' are binding sites with an adjacent atom.

5. The condensed cyclic compound of claim 1, wherein $R_3$ to $R_6$ and $R_{12}$ to $R_{13}$ are each independently selected from:

a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group, a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a dibenzosilolyl group, a thiadiazolyl group, an imidazopyridinyl group, and an imidazopyrimidinyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a dibenzosilolyl group, a thiadiazolyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group and —Si($Q_{33}$)($Q_{34}$)($Q_{35}$), and —Si($Q_3$)($Q_4$)($Q_5$), wherein $Q_3$ to $Q_5$ and $Q_{33}$ to $Q_{35}$ are each independently selected from a $C_1$-$C_{10}$ alkyl group, a $C_1$-$C_{10}$ alkoxy group, a phenyl group, and a naphthyl group.

6. The condensed cyclic compound of claim 1, wherein $R_3$ to $R_6$ and $R_{12}$ to $R_{13}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, groups respectively represented by Formulae 5-1 to 5-75, and —Si($Q_3$)($Q_4$)($Q_5$), wherein $Q_3$ to $Q_5$ are each independently selected from a $C_1$-$C_{10}$ alkyl group, a $C_1$-$C_{10}$ alkoxy group, a phenyl group, and a naphthyl group:

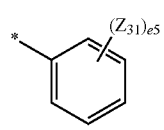

Formula 5-1

Formula 5-2

Formula 5-3

Formula 5-4

Formula 5-5

Formula 5-6

Formula 5-7

Formula 5-8

Formula 5-9

Formula 5-10

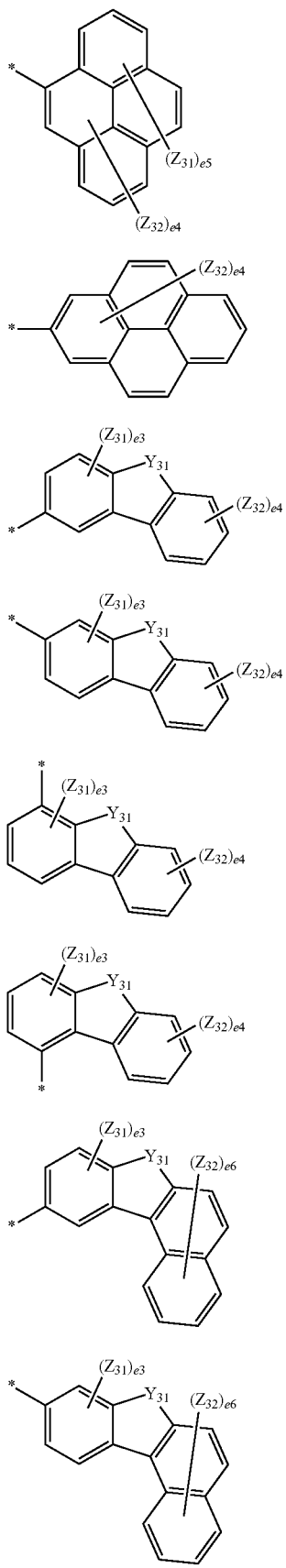
Formula 5-11
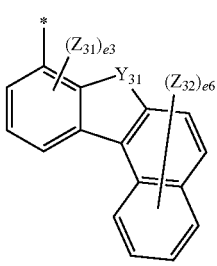
Formula 5-19
Formula 5-12
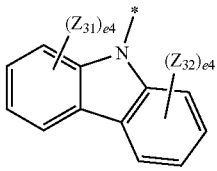
Formula 5-20
Formula 5-13
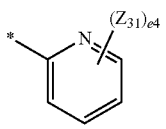
Formula 5-21
Formula 5-14
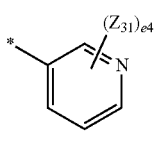
Formula 5-22
Formula 5-15
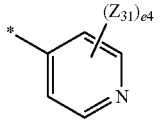
Formula 5-23
Formula 5-16
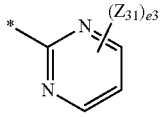
Formula 5-24
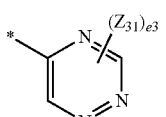
Formula 5-25
Formula 5-17
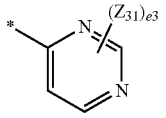
Formula 5-26
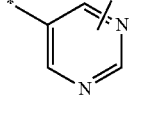
Formula 5-27
Formula 5-18
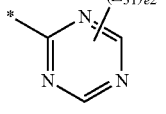
Formula 5-28

-continued
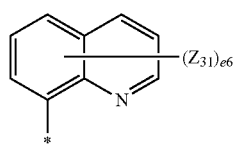
Formula 5-29
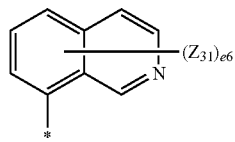
Formula 5-30
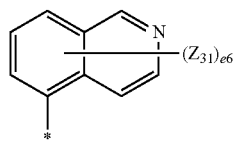
Formula 5-31
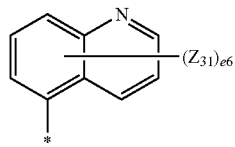
Formula 5-32
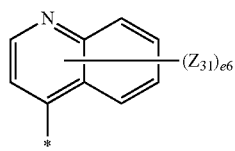
Formula 5-33
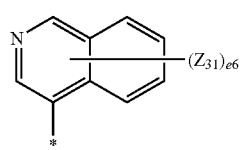
Formula 5-34
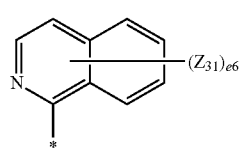
Formula 5-35
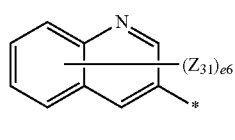
Formula 5-36
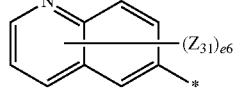
Formula 5-37
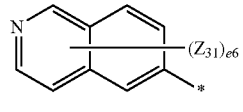
Formula 5-38
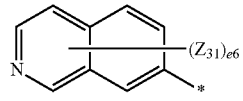
Formula 5-39
-continued
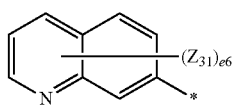
Formula 5-40
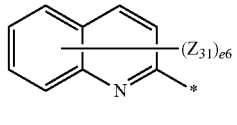
Formula 5-41
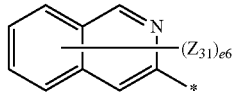
Formula 5-42
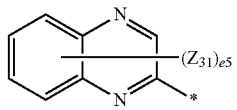
Formula 5-43
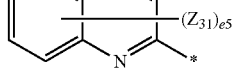
Formula 5-44
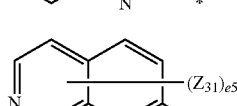
Formula 5-45
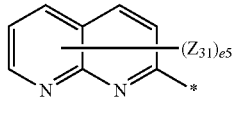
Formula 5-46
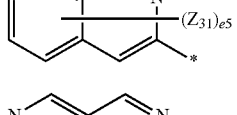
Formula 5-47
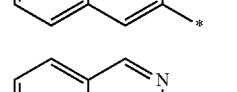
Formula 5-48
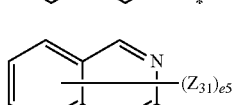
Formula 5-49
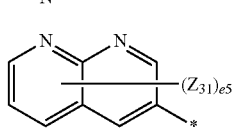
Formula 5-50
Formula 5-51
Formula 5-52
Formula 5-53

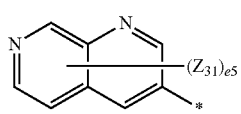 Formula 5-54
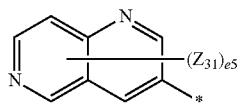 Formula 5-55
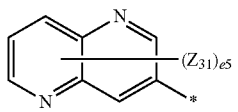 Formula 5-56
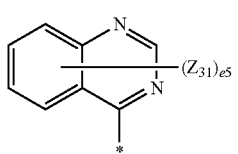 Formula 5-57
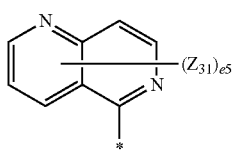 Formula 5-58
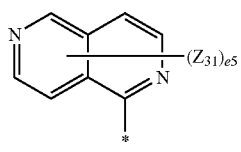 Formula 5-59
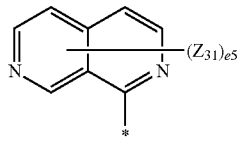 Formula 5-60
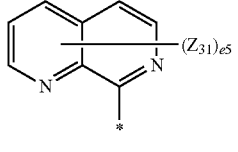 Formula 5-61
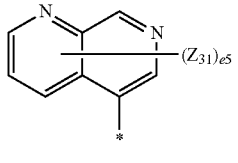 Formula 5-62
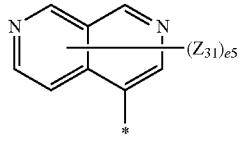 Formula 5-63
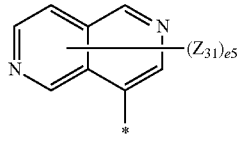 Formula 5-64
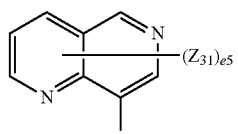 Formula 5-65
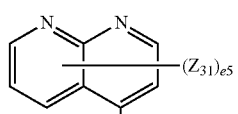 Formula 5-66
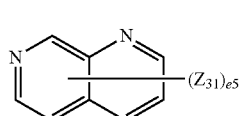 Formula 5-67
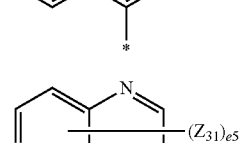 Formula 5-68
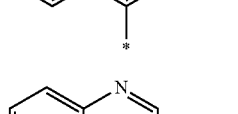 Formula 5-69
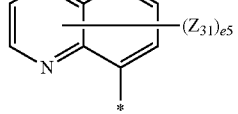 Formula 5-70
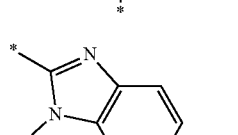 Formula 5-71
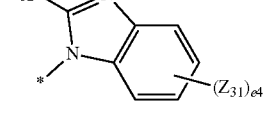 Formula 5-72
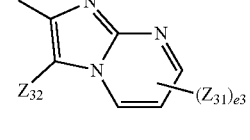 Formula 5-73
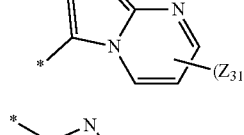 Formula 5-74
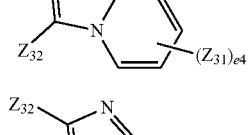 Formula 5-75
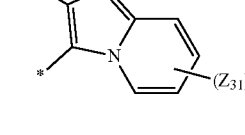

wherein, in Formulae 5-1 to 5-75, $Y_{31}$ is O, S, $C(Z_{33})(Z_{34})$, $N(Z_{35})$, or $Si(Z_{36})(Z_{37})$;

$Z_{31}$ to $Z_{37}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a biphenyl group, a terphenyl group, and —$Si(Q_{33})(Q_{34})(Q_{35})$, wherein $Q_{33}$ to $Q_{35}$ are each independently selected from a $C_1$-$C_{10}$ alkyl group, a $C_1$-$C_{10}$ alkoxy group, a phenyl group, and a naphthyl group;

e2 is an integer selected from 1 and 2;
e3 is an integer selected from 1 to 3;
e4 is an integer selected from 1 to 4;
e5 is an integer selected from 1 to 5;
e6 is an integer selected from 1 to 6;
e7 is an integer selected from 1 to 7;
e8 is an integer selected from 1 to 8;
e9 is an integer selected from 1 to 9; and
* is a binding site with an adjacent atom.

7. The condensed cyclic compound of claim 1, wherein $R_3$ to $R_6$, and $R_{13}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, and —$Si(Q_3)(Q_4)(Q_5)$; and $R_{12}$ is selected from groups respectively represented by Formulae 6-1 to 6-43, and groups respectively represented by Formulae 10-1 to 10-117, wherein $Q_3$ to $Q_5$ are each independently selected from a $C_1$-$C_{10}$ alkyl group, a $C_1$-$C_{10}$ alkoxy group, a phenyl group, and a naphthyl group:

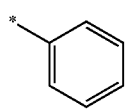

Formula 6-1

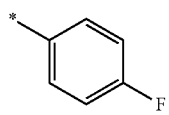

Formula 6-2

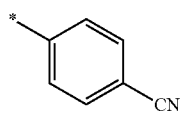

Formula 6-3

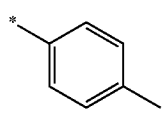

Formula 6-4

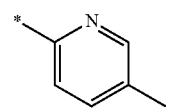

Formula 6-5

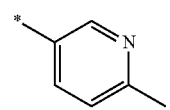

Formula 6-6

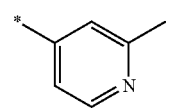

Formula 6-7

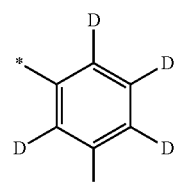

Formula 6-8

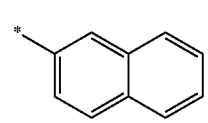

Formula 6-9

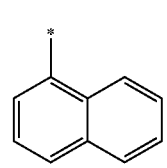

Formula 6-10

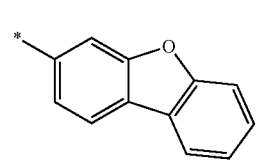

Formula 6-11

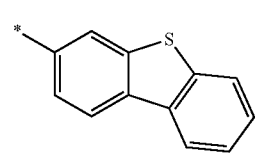

Formula 6-12

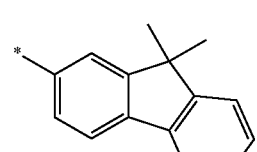

Formula 6-13

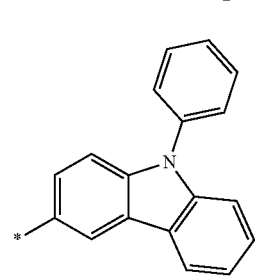

Formula 6-14

-continued
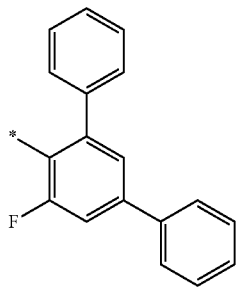
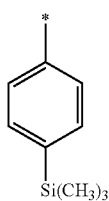
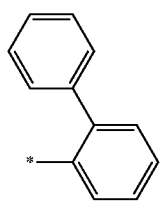
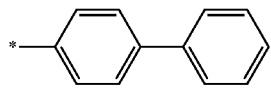
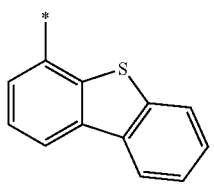
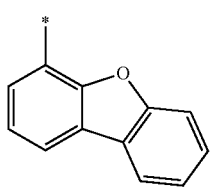
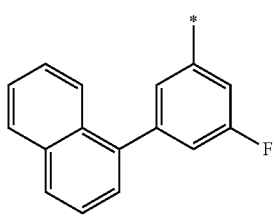
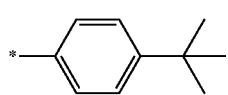
-continued
Formula 6-15
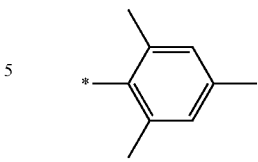
Formula 6-16
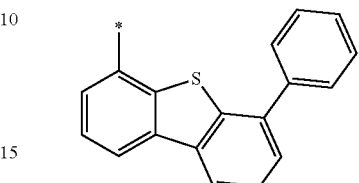
Formula 6-17
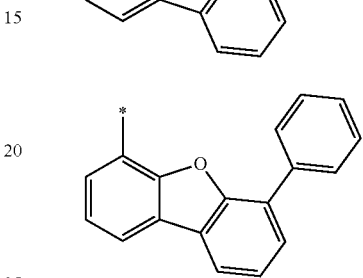
Formula 6-18
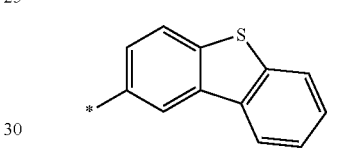
Formula 6-19
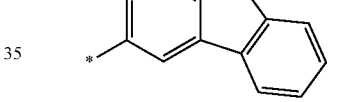
Formula 6-20
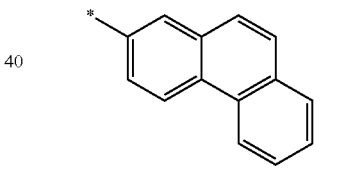
Formula 6-21
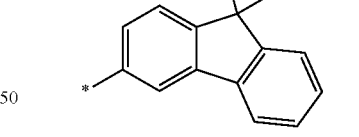
Formula 6-22
Formula 6-23
Formula 6-24
Formula 6-25
Formula 6-26
Formula 6-27
Formula 6-28
Formula 6-29
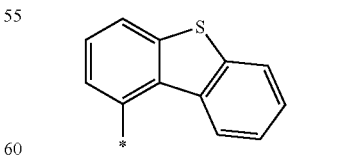
Formula 6-30
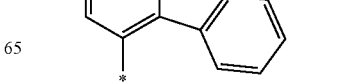
Formula 6-31

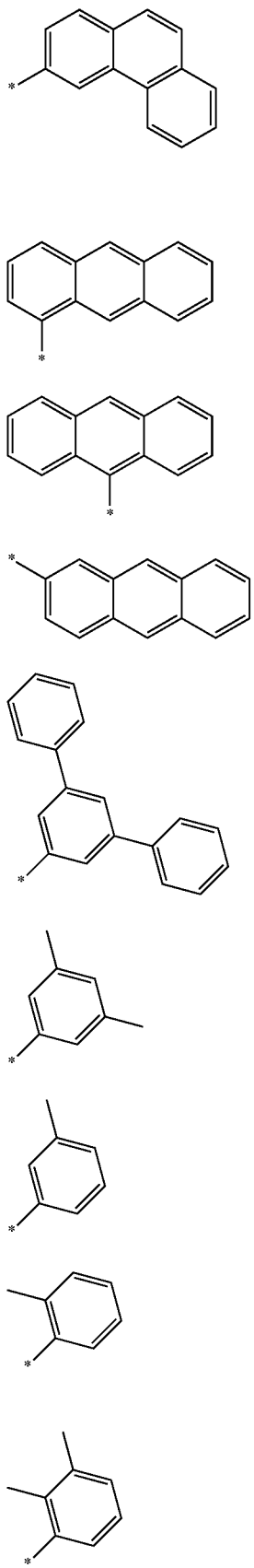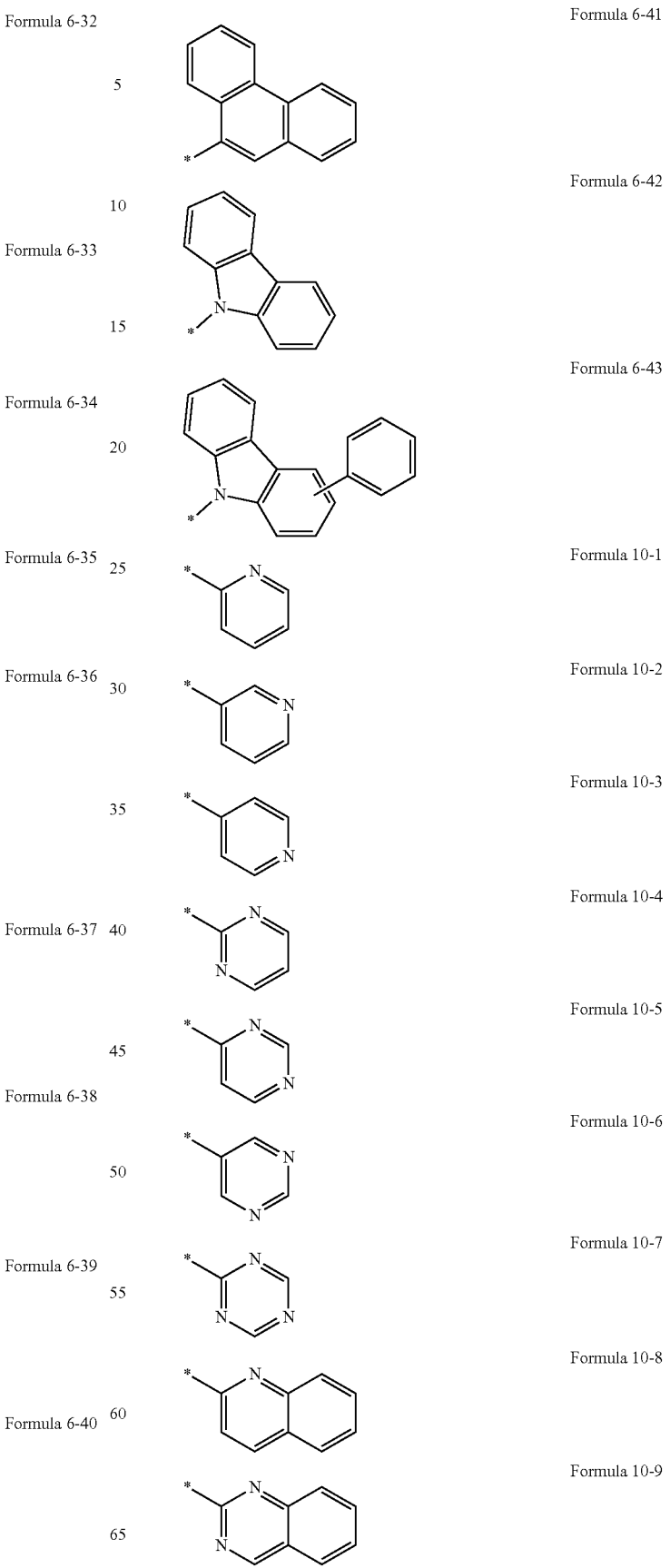

-continued
Formula 10-10
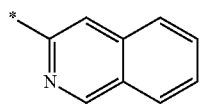
Formula 10-11
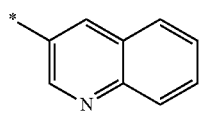
Formula 10-12
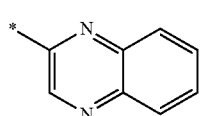
Formula 10-13
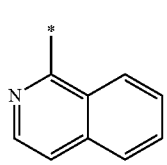
Formula 10-14
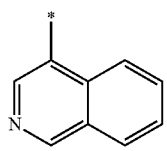
Formula 10-15
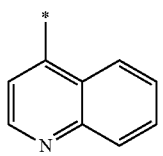
Formula 10-16
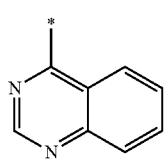
Formula 10-17
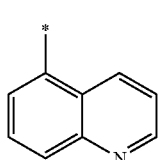
Formula 10-18
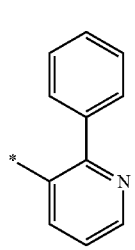
Formula 10-19
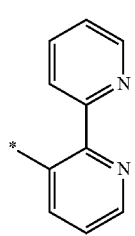
-continued
Formula 10-20
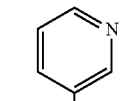
Formula 10-21
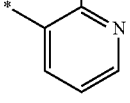
Formula 10-22
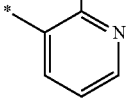
Formula 10-23
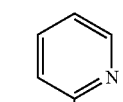
Formula 10-24
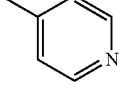
Formula 10-25
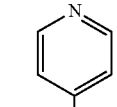
Formula 10-26
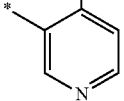

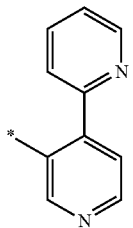
Formula 10-27
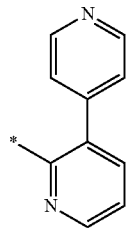
Formula 10-33
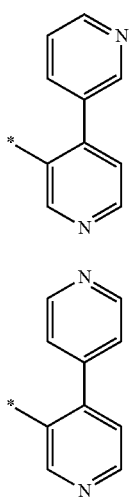
Formula 10-28
Formula 10-29
Formula 10-30
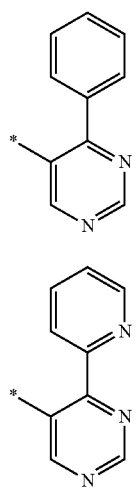
Formula 10-34
Formula 10-35
Formula 10-36
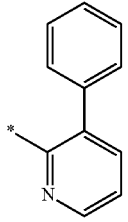
Formula 10-31
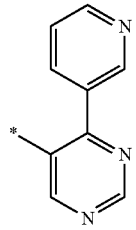
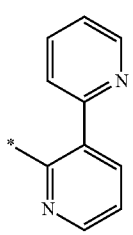
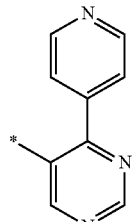
Formula 10-37
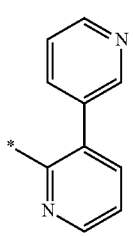
Formula 10-32
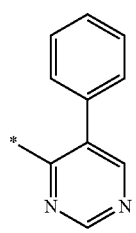
Formula 10-38

Formula 10-39
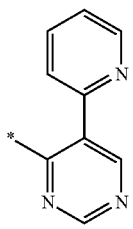
Formula 10-40
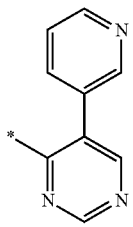
Formula 10-41
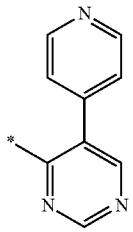
Formula 10-42
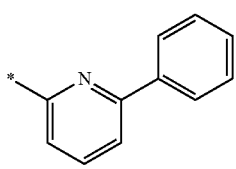
Formula 10-43
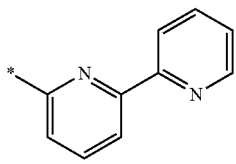
Formula 10-44
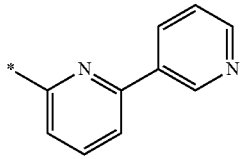
Formula 10-45
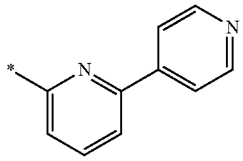
Formula 10-46
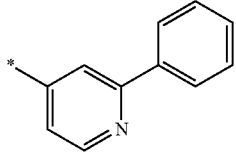
Formula 10-47
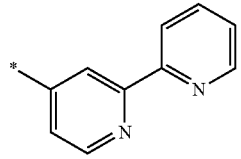
Formula 10-48
Formula 10-49
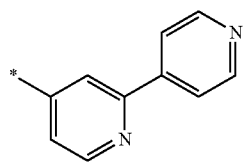
Formula 10-50
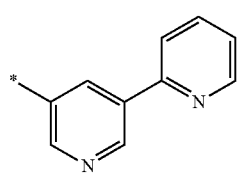
Formula 10-51
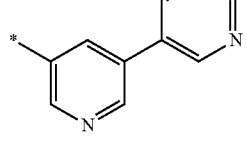
Formula 10-52
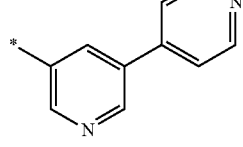
Formula 10-53
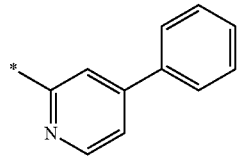
Formula 10-54
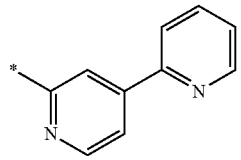
Formula 10-55

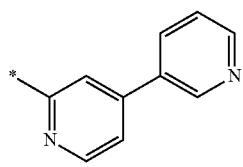
Formula 10-56
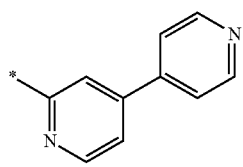
Formula 10-57
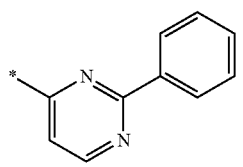
Formula 10-58
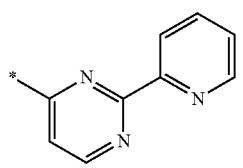
Formula 10-59
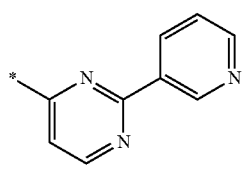
Formula 10-60
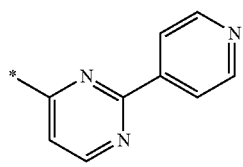
Formula 10-61
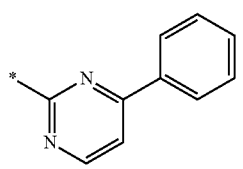
Formula 10-62
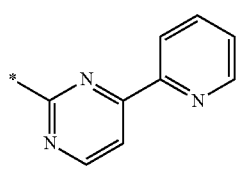
Formula 10-63
Formula 10-64
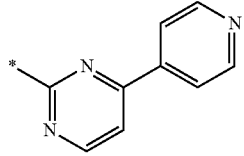
Formula 10-65
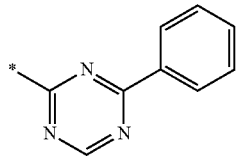
Formula 10-66
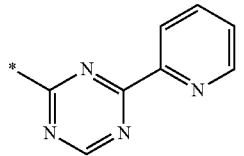
Formula 10-67
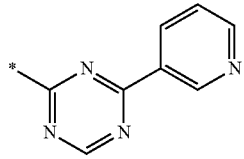
Formula 10-68
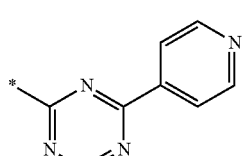
Formula 10-69
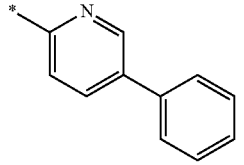
Formula 10-70
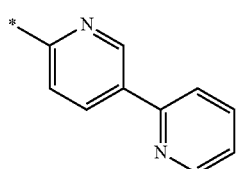
Formula 10-71
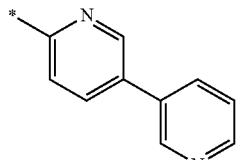
Formula 10-72
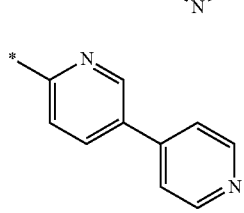
Formula 10-73

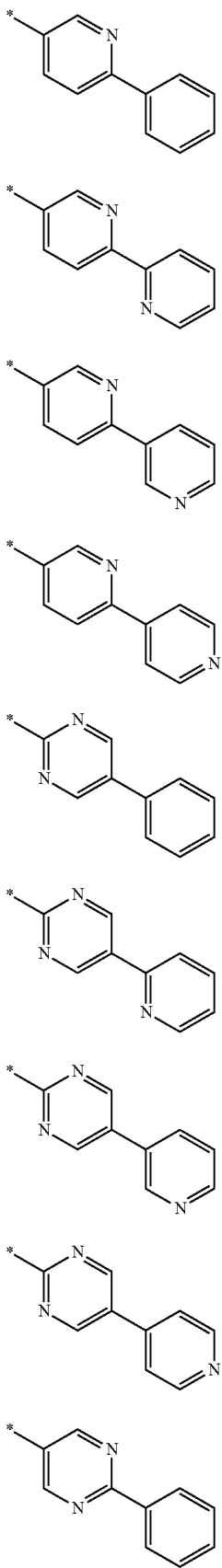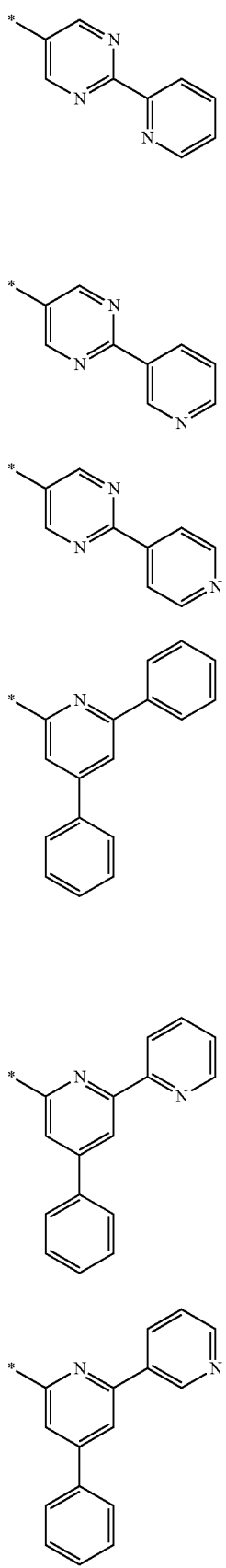
Formula 10-74
Formula 10-75
Formula 10-76
Formula 10-77
Formula 10-78
Formula 10-79
Formula 10-80
Formula 10-81
Formula 10-82
Formula 10-83
Formula 10-84
Formula 10-85
Formula 10-86
Formula 10-87
Formula 10-88

-continued
Formula 10-89
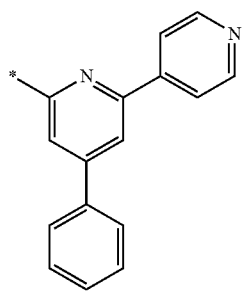
Formula 10-90
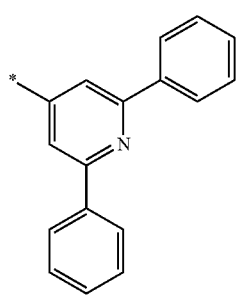
Formula 10-91
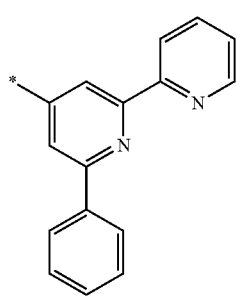
Formula 10-92
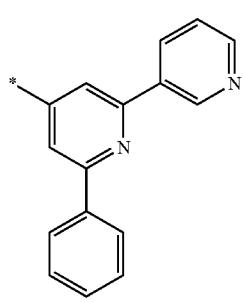
Formula 10-93
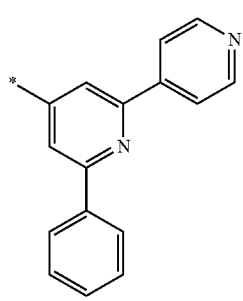
Formula 10-94
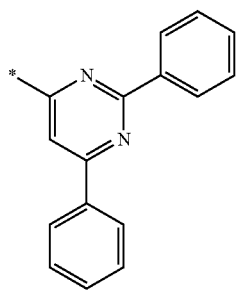
Formula 10-95
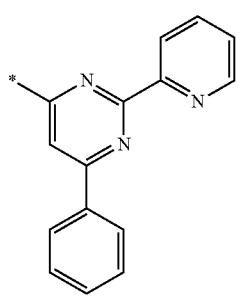
Formula 10-96
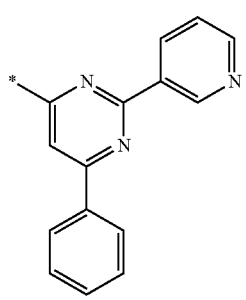
Formula 10-97
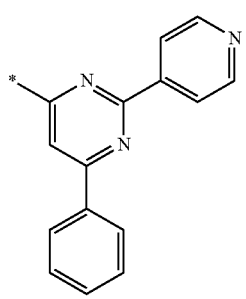
Formula 10-98
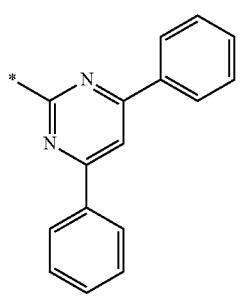

Formula 10-99
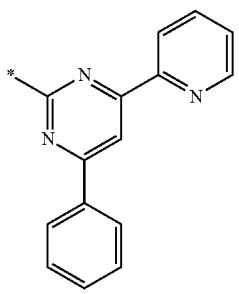
Formula 10-100
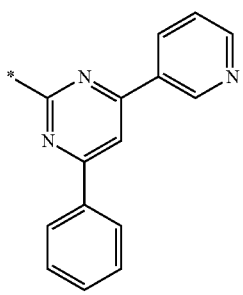
Formula 10-101
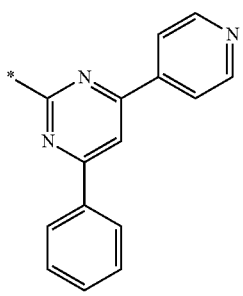
Formula 10-102
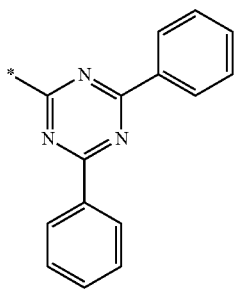
Formula 10-103
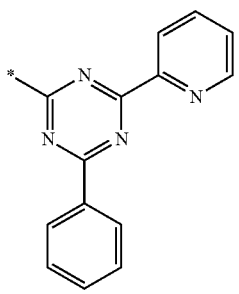
Formula 10-104
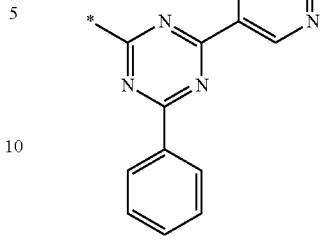
Formula 10-105
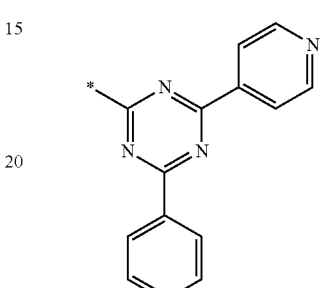
Formula 10-106
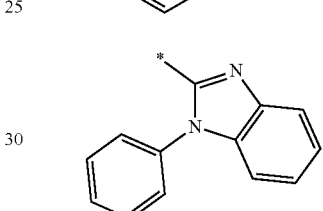
Formula 10-107
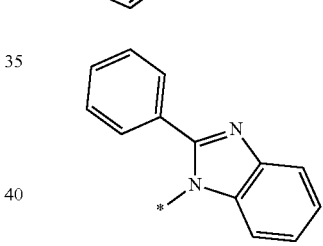
Formula 10-108
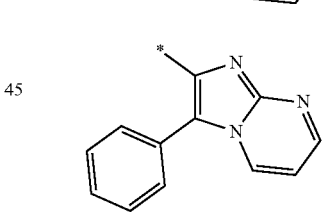
Formula 10-109
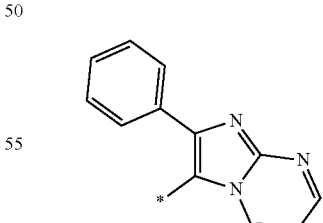
Formula 10-110
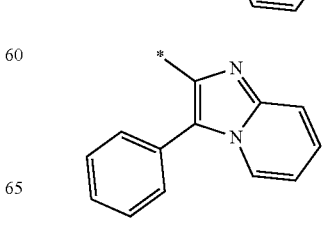

-continued

Formula 10-111
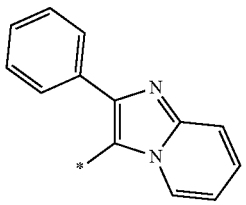

Formula 10-112
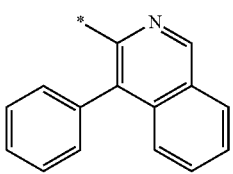

Formula 10-113
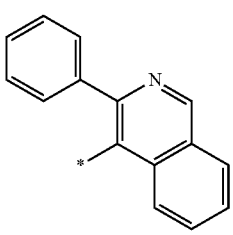

Formula 10-114
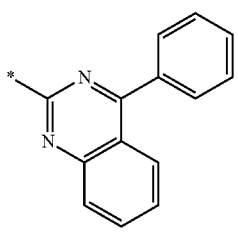

Formula 10-115
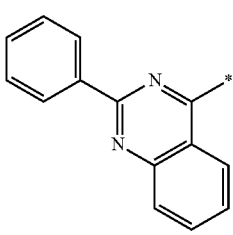

Formula 10-116
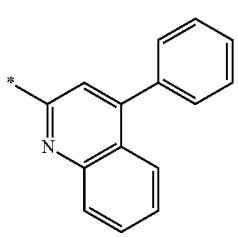

Formula 10-117
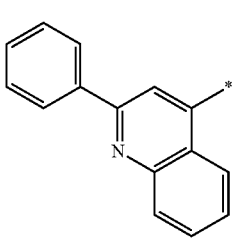

wherein, in Formulae 6-1 to 6-43 and Formulae 10-1 to 10-117, * is a binding site with an adjacent atom.

8. The condensed cyclic compound of claim 1, wherein c1 is 1, and c2 is 0; or c1 is 1, and c2 is 1.

9. The condensed cyclic compound of claim 1, wherein the condensed cyclic compound represented by one of Formulae 1A or 1C to 1E is a compound represented by one of Formulae 1(2) to 1(5), 1(8), and 1(21) to 1(24):

Formula 1(2)
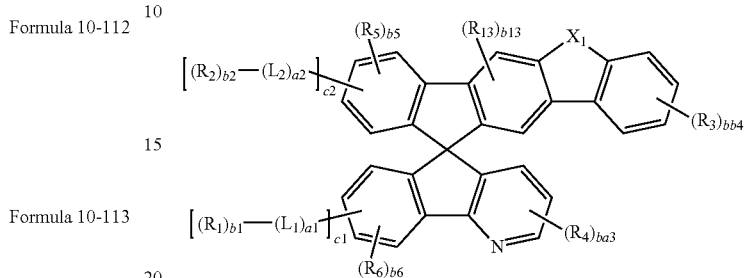

Formula 1(3)
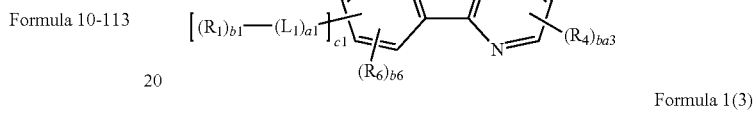

Formula 1(4)
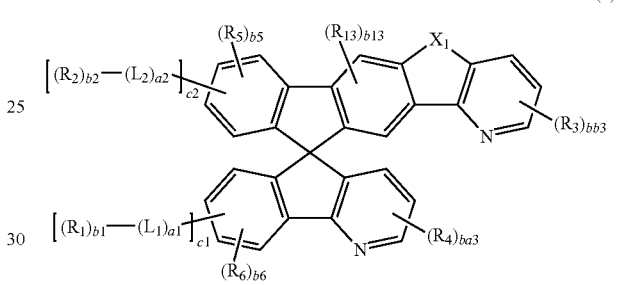

Formula 1(5)
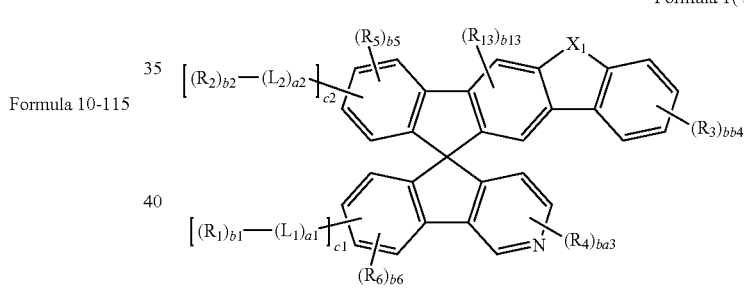

Formula 1(5)
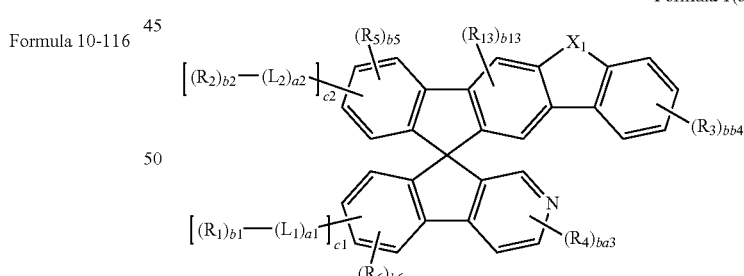

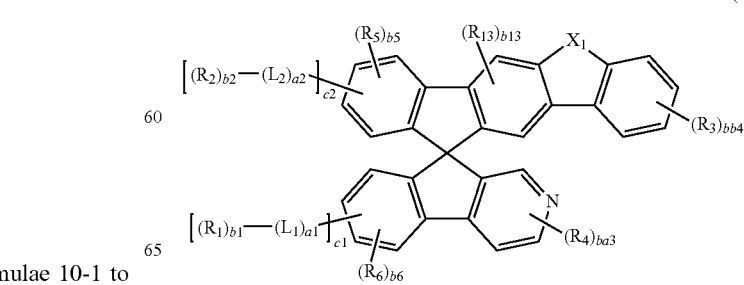

-continued

Formula 1(8)

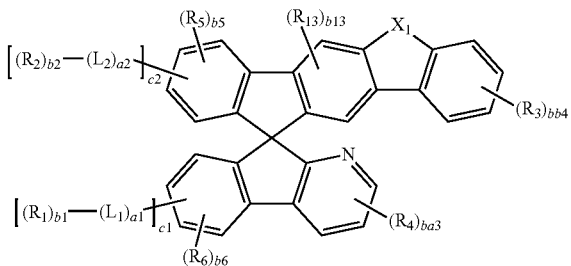

Formula 1(21)

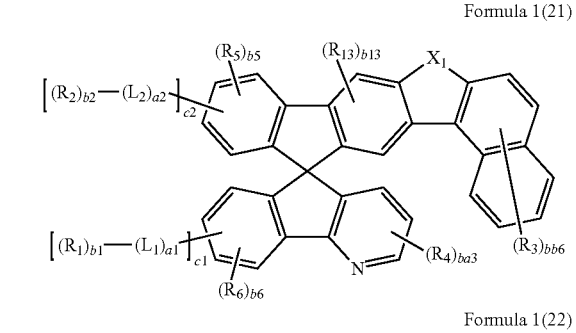

Formula 1(22)

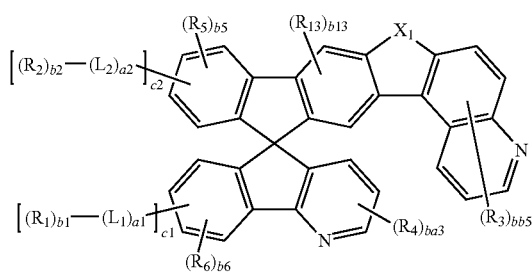

Formula 1(23)

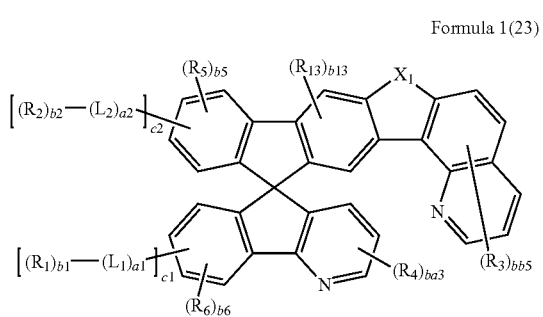

-continued

Formula 1(24)

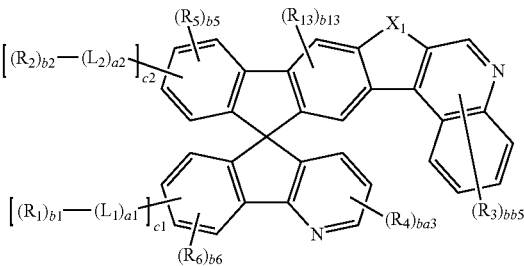

wherein, in Formulae 1(2) to 1(5), 1(8), and 1(21) to 1(24), $X_1$, $L_1$, $L_2$, a1, a2, $R_1$ to $R_6$, $R_{13}$, b1 to b6, b13, c1, and c2 are defined the same as those defined in claim 1;

ba3 and bb3 are each independently an integer selected from 0 to 3;

ba4 and bb4 are each independently an integer selected from 0 to 4;

ba5 and bb5 are each independently an integer selected from 0 to 5; and ba6 and bb6 are each independently an integer selected from 0 to 6.

10. An organic light-emitting device comprising: a first electrode; a second electrode facing the first electrode; and an organic layer between the first electrode and the second electrode and comprising an emission layer, wherein the organic layer comprises at least one of the condensed cyclic compound of claim 1.

11. The organic light-emitting device of claim 10, wherein the first electrode is an anode, the second electrode is a cathode, the organic layer comprises i) a hole transport region between the first electrode and the emission layer and comprising at least one selected from a hole injection layer, a hole transport layer, a buffer layer, and an electron blocking layer, and ii) an electron transport region between the emission layer and the second electrode and comprising at least one selected from a hole blocking layer, an electron transport layer, and an electron injection layer, and at least one selected from the hole transport region and the emission layer comprises the at least one of the condensed cyclic compound.

12. The organic light-emitting device of claim 10, wherein the emission layer comprises the at least one of the condensed cyclic compound.

13. The organic light-emitting device of claim 10, wherein the emission layer further comprises a fluorescent dopant.

* * * * *